US007892541B1

(12) United States Patent
Maihle et al.

(10) Patent No.: US 7,892,541 B1
(45) Date of Patent: Feb. 22, 2011

(54) SOLUBLE EPIDERMAL GROWTH FACTOR RECEPTOR ISOFORMS

(75) Inventors: Nita J. Maihle, New Haven, CT (US); Andre Baron, Lexington, KY (US); Jill Reiter, New Haven, CT (US)

(73) Assignee: Tumor Biology Investment Group, Inc., Lexington, KY (US)

( * ) Notice: Subject to any disclaimer, the term of this patent is extended or adjusted under 35 U.S.C. 154(b) by 0 days.

(21) Appl. No.: 12/206,445

(22) Filed: Sep. 8, 2008

Related U.S. Application Data

(63) Continuation-in-part of application No. 09/676,380, filed on Sep. 29, 2000.

(60) Provisional application No. 60/157,144, filed on Sep. 30, 1999.

(51) Int. Cl.
 *A61K 39/00* (2006.01)
(52) U.S. Cl. ............... 424/130.1; 530/350; 530/387.1; 530/387.3; 530/388.1; 530/389.1; 514/19.3
(58) Field of Classification Search ............... None
 See application file for complete search history.

(56) References Cited

U.S. PATENT DOCUMENTS

| | | | |
|---|---|---|---|
| 4,676,980 | A | 6/1987 | Segal et al. |
| 4,741,900 | A | 5/1988 | Alvarez et al. |
| 4,816,537 | A | 3/1989 | Boss et al. |
| 4,816,567 | A | 3/1989 | Cabilly et al. |
| 4,946,778 | A | 8/1990 | Ladner et al. |
| 5,183,884 | A | 2/1993 | Kraus |
| 5,252,348 | A | 10/1993 | Schreier et al. |
| 5,258,498 | A | 11/1993 | Huston et al. |
| 5,264,618 | A | 11/1993 | Felgner et al. |
| 5,459,127 | A | 10/1995 | Felgner et al. |
| 5,545,806 | A | 8/1996 | Lonberg et al. |
| 5,569,825 | A | 10/1996 | Lonberg et al. |
| 5,585,089 | A | 12/1996 | Queen et al. |
| 5,625,126 | A | 4/1997 | Lonberg et al. |
| 5,633,425 | A | 5/1997 | Lonberg et al. |
| 5,661,016 | A | 8/1997 | Lonberg et al. |
| 5,674,618 | A | 10/1997 | Lee et al. |
| 5,708,156 | A | 1/1998 | Ilekis |
| 5,766,625 | A | 6/1998 | Schreier et al. |
| 5,807,683 | A | 9/1998 | Brenner |
| 2003/0219842 | A1 | 11/2003 | Carney et al. |
| 2007/0042405 | A1 | 2/2007 | Lokshin |

FOREIGN PATENT DOCUMENTS

| | | |
|---|---|---|
| EP | 125023 | 11/1984 |
| EP | 173494 | 3/1986 |
| EP | 184187 | 6/1986 |
| EP | 171496 | 2/1989 |
| WO | 8601533 | 3/1986 |
| WO | 8702671 | 5/1987 |

OTHER PUBLICATIONS

Mayes et al., The EMBO Journal, 1984; 3: 531-537.*
Hennekens, C.H., and Buring, J.E. Screening in: S.L. Mayrent (ed.) Epidemiology in Medicine, pp. 327-347 (Ch. 13) Boston; Little, Brown, 1987.
Gatineau, M., et. al., Phase II combination of gefitinib and docetaxel for advanced or metastatic non-small cell lung cancer: clinical results and biological monitoring, Targeted Oncology, vol., 1, No. 3, Jul. 2006.
Kong, Y. et al., Elevated soluble epidermal growth factor recepter level in pituitary adenoma and carcinoma, Chin Med Sci J. Sep. 2004; 19(3): 199-202.
Li, S. et al., Structural basis for inhibition of the epidermal growth factor receptor by cetuximab., Cancer Cell, Apr. 2005; 7(4): 301-11.
Hudelist, G., et al., Serum EGFR levels and efficacy of trastuzumab-based therapy in patients with metastatic breast cancer., Eur J Cancer, Jan. 2006; 42(2); 186-92. Epub Dec. 2, 2005.
Müller, V., et al., Prognostic and predictive impact of soluble epidermal growth factor receptor (sEGFR) protein in the serum of patients treated with chemotherapy for metastatic breast cancer, Anticancer Res. Mar.-Apr. 2006; 26(2B): 1479-87.
Witzel I., et al., Clinical utility of determination of HER-2/neu and EGFR fragments in serum of patients with metastatic breast cancer, Int J Biol Markers. Jul.-Sep. 2006;21(3):131-40.
Sandri, MT, Serum EGFR and serum HER-2/neu are useful predictive and prognostic markers in metastatic breast cancer patients treated with metronomic chemotherapy, Cancer, Aug. 1, 2007; 110(3); 509-517.
Chudecka-Glaz, A, et al., Gonadotropin (LH, FSH) levels in serum and cyst fluid in epithelial tumors of the ovary, Arch Gynecol Obstet. Nov. 2004;270(3): 151-76. Epub Jul. 23, 2003.
Krämer, S., et al., Gonadotropin levels in ovarian cyst fluids: a predictor of malignancy?, Int J Biol Markers. Jul.-Sep. 1998; 13(3): 165-8.
Zampino, M.G., et al., Epidermal growth factor receptor serum (sEGFR) level may predict response in patients with EGFR positive advanced colorectal cancer treated with getfitinib?, Cancer, DOI 10.1007/s00280-008-0722-x, 2008.

(Continued)

*Primary Examiner*—Bridget E Bunner
*Assistant Examiner*—Christina Borgeest
(74) *Attorney, Agent, or Firm*—Cohen & Grigsby, P.C.

(57) ABSTRACT

Embodiments of the present invention relate to p110 soluble EGFR (p110 sEGFR) peptides and nucleic acid sequences. Antibodies, methods of detection, kits, and expression vectors for p110 sEGFR are disclosed. In addition, assays on biological samples for determining and evaluating risk assessment and cancer prevention, screening and early detection, diagnosis, prognosis, theragnosis, monitoring of responsiveness to treatment, and monitoring of disease progression, recurrence, or metastasis of a cancer, are disclosed. In examples, a lower p110 sEGFR concentration adjusted for demographical and physiological variables and other biomarkers is associated with cancer. Therapeutics and methods of treating a cancer related to p110 sEGFR also are embodied herein.

10 Claims, 23 Drawing Sheets

OTHER PUBLICATIONS

Gregorc, V., et al., Effects of Gefitinib on Serum Epidermal Growth Factor Receptor and HER2 in Patients with Advanced Non-Small Cell Lung Cancer, Clinical Cancer Research, 6006 vol. 10, 6006-6012, Sep. 2004.
Linkov, F., et al., Early Detection of Head and Neck Cancer: Development of a Novel Screening Tool Using Multiplexed Immunobead-Based Biomarker Profiling, Cancer Epidemiol Biomarkers Prev 2007; 16(1). Jan. 1, 2007.
Lafky, J., et al., Clinical implications of the ErbB/epidermal growth factor (EGF) receptor family and its ligands in ovarian cancer, Science Direct, Biochimica et Biophysica Acta 1785 (2008) 232-265.
Baron, A., et al., A Preliminary Study of Serum Concentrations of Soluble Epidermal Growth Factor Receptor (sErbB1), Gonadotropins, and Steroid Hormones in Healthy Men and Women, Cancer Epidemiology Biomarkers & Prevention vol. 10, 1175-1185, Nov. 2001.
Adelman et al., In Vitro Mutagenesis (DNA 2:183, 1983).
Felgner et al., Lipofection: a highly efficient, lipid-mediated DNA-transfection procedure Annals N.Y. Acad. Sci. 772:126-139, 1995).
Arnon et al., "Monoclonal Antibodies for Immunotargeting of Drugs in Cancer Therapy", in Monoclonal Antibodies and Cancer Therapy, Reisfeld et al. (eds.), pp. 243-256 (Alan R. Liss, Inc. 1985).
Ausubel et al., Current Protocols in Molecular Biology, John Wiley & Sons, NY (1994).
Baron et al., Serum sErbB1 and Epidermal Growth Factor Levels As Tumor Biomarkers in Women with Stage III or IV Epithelial Ovarian Cancer1 J. Immunol. Methods, 219, 23 (1998).
Baron, A.T., et al., Cancer Epidemiol Biomarkers Prev, 14: 306-18, 2005.
Beidler et al., 1988, J. Immunol. 141:4053-4060.
Better et al., 1988, Science 240:1041-1043.
Bird, 1988, Science 242:42342.
Boussif et al., PNAS 92:7297-7301, 1995.
Chen et al, Requirement for intrinsic protein tyrosine kinase in the immediate and late actions of the EGF receptor. Nature, 32, 820 (1987).
Cole et al., 1985, Monoclonal Antibodies and Cancer Therapy, Alan R. Liss, Inc., pp. 77-96.
Coussens et al., Tyrosine kinase receptor with extensive homology to EGF receptor shares chromosomal location with neu oncogene. Science, 230, 1132 (1988).
Cunningham and Wells, High-Resolution Epitope Mapping of hGH-Receptor Interactions by Alanine-Scanning Mutagenesis (Science 244:1081-1085, 1989).
Curiel et al. 1992 Am. J. Respir. Cell Mol. Biol. 6:247-52.
Das et al., Endocrinology 134,971 (1994).
Felgner et al., Lipofection: a highly efficient, lipid-mediated DNA-transfection procedure PNAS 84:7413-7417, 1987.
Flickinger et al., Mol. Cell, Biol., 12, 883 (1992).
Goeddel et al., Synthesis of human fibroblast interferon by *E. coil* Nucleic Acids Res., 8, 4057 (1980).
Hellstrom et al., "Antibodies for Drug Delivery", in Controlled Drug Delivery (2nd Ed.), Robinson et al. (eds.), pp. 623-653 (Marcel Dekker, Inc. 1987).
Hendler et al, Proc. Am. Soc. Clin. Oncol., 8, 223 (1989).
Hennekens, C. H. and Buring (1987). Screening. Epidemiology in Medicine. S.L. Mayrent. Boston : Little, Brown: 327-47 (Chapter 13) Boston: Little, Brown.
Huang, L., L. O. Gainkam, et al. (2008) Mol Imaging Biol 10(3): 167-75.
Hunts et al., Cell Mol. Genet., 11, 477 (1988).
Huston et al., 1988, Proc. Natl. Acad. Sci, USA 85:5879-5883.
Huston et al., Methods in Enzymology 203:46-88 (1991).
Hyrup et al, Bioorganic & Medicinal Chemistry, 4:523, 1996.
Ilekis et al., Mol. Reprod. Devel., 41, 149 (1995).
Inouye & Inouye, 1985, Nucleic Acids Res. 13:3101-3109.
Izant J. G. and Weintraub H., (Cell, 36: 100.7-1015, 1984).
Jones et al., 1986, Nature 321:552-525.
Kohler, 1980, Proc. Nat'l Acad. Sci. USA 77:2197.
Kohler and Milstein, 1975, Nature 256:495-497.
Kozbor et al., 1983, Immunology Today 4:72.
Kutmeier et al. (1994, BioTechniques 17:242).
Lam, 1997, Anticancer Drug Des. 12:145; U.S. Appl. No, 5,738,996.
Lax et al., Cell Regul. 2,337 (1991).
Leitzel et al., J. Clin. Oncol., 13, 1129 (1995).
Liu et al., 1987, J. Immunol. 139:3521-3526.
Liu et al., 1987, Proc. Nati. Acad. Sci, USA 84:3439-3443.
Lonberg and Huszar Human antibodies from transgenic mice (1995, Int, Rev. Immunol. 13:65-93).
Maihle et al. Proc. Nat'l Acad. Sci, USA, 88, 1825 (1991).
Maihle et al., Mol. Cell. Biol., 8, 4868 (1988).
Maniatis, T., Fritsch, E. F. & Sambrook, J. (1982).Molecular Cloning, A Laboratory Manual. Cold Spring Harbor Laboratory, Cold Spring Harbor, New York.
McKenzie, Biochim. Biophys, Acta, 1072, 193 (1991).
Meden et al., Anticancer Res., 17, 757 (1997).
Merlino et al., Mol. Cell. Biol., 5, 1722 (1985).
Morrison, 1985, Science 229:1202-1207.
Moscovici et al., Continuous Tissue Culture Cell Line Derived From Chemically Induced Tumors of Japanese Quails vol. 1, Issue 1 May 1977.
Neal et al., Cancer, 65, 1619 (1990).
Neuberger et al., 1984, Nature 312:604-608.
Nishimura et al., 1987, Canc. Res. 47:999-1005.
Oi et al., 1986, Bio/Techniques 4:214.
Partanen et al., J. Occup. Med., 36, 1324 (1994).
Plowman et al., Proc. Nat'l. Acad. Sci. USA, 90, 1746 (1993).
Plowman, et al., Proc. Nat'l. Acad. Sci. USA 87, 4905 (1990).
Proudfoot, 1986, Nature 322:52; Kohler, 1980, Proc. Natl. Acad. Sci. USA 77:2197.
Reiter and Maihle, Nucl. Acids Res., 24, 4050 (1996).
Rosenberg et al. (Nature, 313:703-706, 1985).
Salomon DS, Brandt R, Ciardiello F, et al. Epidermal growth factor-related peptides and their receptors in human malignancies. Crit Rev Oncol Hematol.1995;19:183-232.
Sambrook et al. (2001, Molecular Cloning, A Laboratory Manual, 3d Ed., Cold Spring Harbor Laboratory, Cold Spring Harbor, N. Y.).
Scambia et al., J. Clin. Oncol., 10, 529 (1992).
Schlegel et al., Int. J. Cancer, 56, 72 (1994).
Shaw et al., 1988, J. Natl. Cancer Inst. 80:1553-1559.
Shu et al., PNAS 90:7995-7999 (1993).
Skerra et al., Science 240:1038-1040 (1988).
Stein and Cohen (Cancer Res. 48:2659, 1988).
Stewart et al., Solid Phase Peptide Synthesis, W.H. Freeman Co., San Francisco (1969).
Suresh et al., Methods in Enzymology, 1986, 121:210.
Takeda et al., 1985, Nature 314:452-454.
Tijink, B. M., T. Laeremans, et al. (2008) Mol Cancer Ther 7(8): 2288-2297).
Ullrich et al., Nature, 309, 418 (1984).
Van der Krol et al. (Bio Techniques 6:958, 1988).
Van Heeke & Schuster, 1989, J. Biol. Chem. 24:5503-5509.
Veale et al., Cancer Res., 49, 1313 (1989).
Verhoeyan et al. (1998) Science 239:1534.
Viera et al., Meth. Enzymol., 153, 3 (1987).
Ward et al., 1989, Nature 334:544-54.
Waterfield et al., J. Cell. Biochem., 20, 149 (1989).
Witters et al., Clin. Cancer Res., 1, 551 (1995).
Wood et al., 1985. Nature 314:446-449.
Xu et al., Proc, Nat'l. Acad. Sci, 81, 7308 (1984).
Yamauchi et al., J. Clin. Oncol., 15, 2518 (1997).
Zhen et al., Biochemistry 42, 5478 (2003).
Baron, A., et al., Monoclonal antibodies specific for peptide epitopes of the Epidermal Growth Factor Receptor's extracellular domain, Hybridoma, vol. 16, No. 3, pp. 259-271, 1997.
Pollack, A., Cancer Test for Women Raises Hope, and Concern, The New York Times, Aug. 25, 2008.
Zhong, L., Efficient Identification and Use of Tumor-Associated Antibodies as Markers of Non-small Cell Lung Cancer, Chest. 2004;125:105S-106S.).
Hamer, P.J., et al., Levels of Serum EGFr in Cancer Patients, Oncogene Science, 2002.
Marx III, J., et al., Serum EGFR in metastatic breast cancer patients, Proc Am Soc Clin Oncol 21: 2002 (abstr 1743).

Carney, W., et al., Normal Levels of Serum EGFr and Decreases in Several Cancers, Abstract #240, OncogeneScience, 2002.

Lafky, J., et al., Soluble Epidermal Growth Factor Receptor Acridinium-Linked Immunosorbent Assay, Methods in Molecular Biology vol. 327: Epidermal Growth Factor: Methods and Protocols, 2005.

Reiter, J., et al., A 1.8 kb alternative transcript from the human epidermal growth factor receptor gene encodes a truncated form of the receptor, 4050-4056, Nucleic Acids Research, 1996, vol. 24, No. 20.

Christensen, T., et al., Generation and Characterization of Polyclonal Antibodies Specific for Human p110 sEGFR, Hybridoma and Hybridomics. vol. 21, No. 3, 2002.

Kimbler, K.D., et al., Soluble Epidermal Growth Factor Receptor (sEGFR/sErbB1) and Gonadotropic Hormones As a Test for Epithelial Ovarian Cancer, Abstract #28 2008.

Perez, E.A., et al., A randomized phase II study of sequential docetaxel and doxorubicin/cyclophosphamide in patients with metastatic breast cancer, Annals of Oncology 13:1225-1235, 2002.

Lemos-González, Y., Alteration of the serum levels of the epidermal growth factor receptor and its ligands in patients with non-small cell lung cancer and head and neck carcinoma, British Journal of Cancer (2007) 96, 1569-1578.

Gatineau, M.P., et al., Soluble epidermal growth factor receptor (EGFR) and HER-2 monitoring in a Phase II combination of gefitinib (ZD1839) and docetaxel for non-small-cell lung cancer (NSCLC), Journal of Clinical Oncology, 2004 ASCO Annual Meeting Proceedings (Post-Meeting Edition). vol. 22, No. 14S (Jul. 15 Supplement), 2004: 7090.

Baron, A., et al., Soluble Epidermal Growth Factor Receptor (SEGFR) and Cancer Antigen 125 (CA125) as Screening and Diagnostic Tests for Epithelial Ovarian Cancer, Cancer Epidemiol Biomarkers Prev 2005; 14(2). Feb. 2005.

Baron, A., et al., Serum sErbB1 and Epidermal Growth Factor Levels As Tumor Biomarkers in Women with Stage III or IV Epithelial Ovarian Cancer, Cancer Epidemiology Biomarkers & Prevention vol. 8, 129-137, Feb. 1999.

Baron, A., et al., Soluble Epidermal Growth Factor Receptor (SEGFR/sErbB1) as a Potential Risk, Screening, and Diagnostic Serum Biomarker of Epithelial Ovarian Cancer, Cancer Epidemiology Biomarkers & Prevention vol. 12, 103-113, Feb. 2003.

* cited by examiner p60 sErbB1
- encoded by 1.8 kb transcript
- mature product = 60 kDa
- contains 381 amino acids
  - unique a.a.: Leu and Ser
- calculated mw = 45 kDa
  - minus signal peptide = 42 kDa p110 sErbB1
- encoded by 3.0 kb transcript
- mature product = 110 kDa
- contains 681 amino acids
  - 78 unique a.a.
- calculated mw = 77 kDa
  - minus signal peptide = 75 kDa

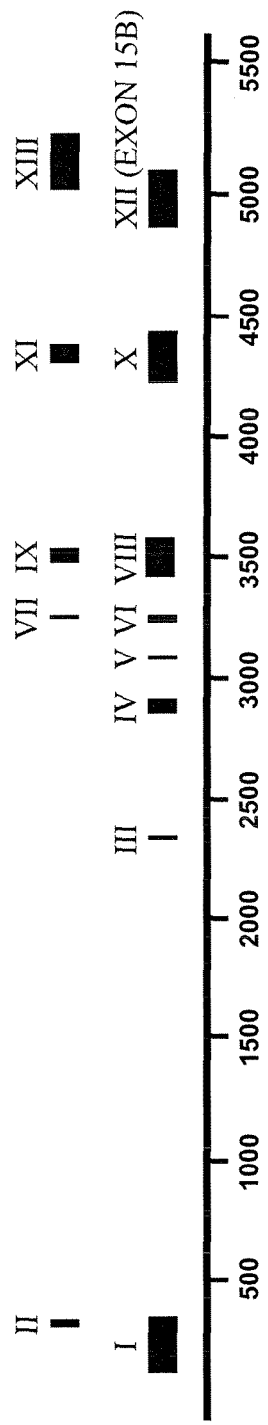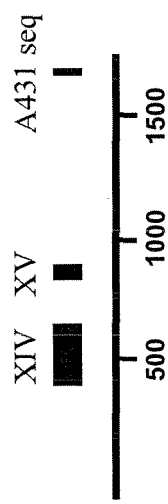
FIGURE 3

| Seq ID | Alternative Exons (coding sequence only) | IVS # | Amino Acids | Translated Peptides |
|---|---|---|---|---|
| Exon 15 | cag GGACCAGACAACTGTATCCAGTGTGCCCACTACATTGACGGCCCCACTG CGTCAAGACCTGCCCGGCCAGGAGTCATGGGAGAAAACAACACCCTGGTCTGGAAG TACGCAGAGCGCCGGCCATGTGCCACCTGTGCCATCCAAACTGCACCTACGG | NA | 53 | GPDNCIQCAHYIDGPHCVKTCP AGVMGENNTLVWKYADAGHVCH LCHPNCTYG |
| I | cag CCATGCCAGTAGCAACTTGCTTGTGAGCAGGCCTCAGTGCTGCAGTGGAATG ACTCTGCCATGCACCGTGTCCCCGGCCGGCCTGTGTCTGCAATGCTGCACAT CACAACAGGAGGGTAGGGGACAAAAGAGCACAGGTCCTGGCAGCTGACAGT CTCCAGGGGCTTTTGCGTTTCTCTCCAGATTTCTAAGGTTAACATGGGGATTAG CTGTTTTGCAATGA | 139-364 | 74 | HASSNLLVSRPQCSGNDSAMHR VPGRACVVQCCTSQQEGRGTKE HRSWQLPQSPGAFAFLSRFLRL TWGLAVLQ* |
| II | cag ATTTCTAAGGTTAACATGGGGATTAGCTGTTTTGCAATGA | 325-364 | 12 | FLRLTWGLAVLQ* |
| III | tag GAAAACAATCATATAA | 2342-2357 | 4 | KTII* |
| IV | tag ATGTGCATCAGTATCTCTGCATCAATATCTCTATATCAGTATCTCTGTGT CAGTGAGCATATGTTGCTGGGCTTAG | 2857-2932 | 24 | CASVSLHQYLYISISVSVSICC WA* |
| V | cag CTCCTAA | 3086-3092 | 1 | S* |
| VI | tag TATGTGTGATTACATTCCTGATTCTGAGCCTTTTTAG | 3229-3265 | 11 | MCDYIPDSEPF* |
| VII | tag ATAG | 3266-3269 | 0 | * |
| VIII | gag TATTTATGACGTGCACAACATTCCTGAATATATTGTCTCTCCATTTCTC AGATGGGATGTATTGCCTTCTCCATTTCTATTGTTAAAGAAACACTTACAGGGG TTTCTTTAACAACTTGTGAACAGCAGCATCAGAGCCCAGACTACAGCATAAGCA GCTGCTGA | 3422-3587 | 54 | IYDVHNIPEYIVSLISQMGCIA FSISIVKETLTGVSLTTCEQQH QSPDYSISSC* |
| IX | cag ATGGGATGTATTGCCTTCTCCATTTCTATTGTTAAAGAAACACTTACAGG GGTTTCTTTAA | 3474-3534 | 19 | WDVLPSFLLLKKHLQGFL* |
| X | cag AGTTACCGAGGGCCTCATCAGCGTCAGCAGAGCCCTCGCCTTCTGACG CTCTCACATCCTTCTCCTCCTGCAGCCCCGTCTGCAGTCTCCTGTCCTTGTCAGCTT CTCTCAAGGGTCAACTGGTCTACCTTCCCTACAGTGTCTGTCACAGTTCTTG TTAGCAATCCCTATGGTTGCCCAAAAGCATTTTCAGAGCCTGCATAA | 4233-4437 | 67 | VTEGLISVSRSPSPSDALTSFS PAAPSCHCPCPASLQGSTGLPF PTSLQLLVSNPYGCPKAFSEP A* |
| XI | cag CCCCGTCCTGCCACTGTCTCCTTGTCCAGCTTCTCTTCAAGGGTCAACTGGT CTAACCTTTCCCTACAAGTCTGTCACAGTTCTTGTTAG | 4307-4394 | 28 | PVLPLSLSSFSSRVNWSTFPYK SVTASC* |
| XII (Exon 15B) | cag GCCAGAAATGAGAGTCTCAAAGCCATGTTATTCTGCCTTTTTAAACTAT CATCCGTAATCAAAGTAATGATGACGCTGTTCCCACCAGAGCGGGAGCCTCAG CTGCTCAGGAGTCATGCTTAGGATGGATGATCCTCCTTCTCTTCTGCCGTCAGAGTTC AGCTGGGTTGGGGTGGAATGCAGCAGCCACCTCTGGCCTTCTGCATCCTGTGA TCATCACGGCCTCCTCCTGCCACTGA | 4870-5107 | 78 | PGNESLKAMLFCLFKLSSCNQS NDGSVSHQSGSPAAQESCLGWI PSLLPSEFQLGWGGCSHLHAWP SASVIITASSCH* |
| XIII | cag AGTTTCAGCTGGGTTGGGGTGGATGCAGCCACCTCCATGCCTGCCTTCT GCATCTGTGATCATCACGGCCTCCTCCTGCCACTGAGCCTCATGCCTTCACGTG TCTGTTCCCCCGCTTTCTTTTCTGCCACCCTGCACTGGGCCGCCAGGTTC CCAATAGTATCCTACCCATTTCCTTCCTTCCACTCCCTTTGCCAGTGCCTCTCA CCCCAACTAGTAGCTAA | 5022-5250 | 75 | VSAGLGWMQPPPCLAFCICDHH GLLPLSLMPSRVCSPRFSFLP PLHVGRQVPKSILPISFLPLPL PVPLTPTSS* |
| Exon 16 | cag ATGCACTGGGCCAGGTCTTGAAGGCTGTCCAACGAATGG | NA | 13 | CTGPGLEGCPTNG |

FIGURE 4

| Seq ID | Alternative Exons (coding sequence only) | IVS # | Amino Acids | Translated Peptides |
|---|---|---|---|---|
| XIV | cag ACACACTGCCCAGCAAAGGCAAAAGGGCTTCCTTCAACATCAGCTCTGGC CAGTTTGCCAGAGCAAAGCCCTGAGAAAAGCAAGGTTGAAAAGTCTTATTCAAA CTCACCAGGAAAGAGTGGTGTTACTCTCGATGGCGTCTAGCCAGGAATCATGA ATTATACACCGAGCACCTGTTTGCCATTTTGGATGTTTCCAAACATGAACCAAA CTTCCAGGCCCCTCTGCCATCTCTGGTAA | 444-684 | 79 | HTAQQRQKGFLQHQLWPVCQSK ALRKARLKSLIQTHQERVVLLS MASSQESWNYTPSTCLPFWMFP NMNQTSRPLCHLW* |
| XV | cag TGAGCTGCTAGGACACCCAGCAGAACTTCCCCACTCCACACTGCAATCTC AGGGATCTTAG | 849-909 | 19 | ELLGHPAELPHSTLQSQGS* |
| A431 seq | tag AAGCTACATAGTGTCTCACTTTCCAAGATCATTCTACAAGATGTCAGTGC ACTGA | 1633-1687 | 17 | SYIVSHFPRSFYKMSVH* |
| Exon 17 | cag GCCTAAGATCCCGTCCATCGCCACTGGGATGGTGGGGGCCCTCCTCTTGC TGCTGGTGGTGGCCCTGGGGATCGGCCTCTTCATGCGAAGGCGCCACATCGTTC GGAAGCGCACGCTGCGCGAGGCTGCTGCAGGAGAGGAG | NA | 47 | PKIPSIATGMVGALLLLVVAL GIGLFMRRHIVRKRTLRRLLQ ERE |

FIGURE 4, continued

SEQUENCE LISTING

<160> NUMBER OF SEQ ID NOS: 54

<210> SEQ ID NO 1
<211> LENGTH: 705
<212> TYPE: PRT
<213> ORGANISM: Homo sapiens

<400> SEQUENCE: 1

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
        50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
                100                 105                 110

Tyr Glu Asn Ser Tyr Ala Leu Ala Val Leu Ser Asn Tyr Asp Ala Asn
            115                 120                 125
```

```
Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
530                 535                 540

Glu Pro Arg Glu Phe Val Glu Asn Ser Glu Cys Ile Gln Cys His Pro
```

```
            545                 550                 555                 560
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
                580                 585                 590
Lys Thr Cys Pro Ala Gly Val Met Gly Glu Asn Asn Thr Leu Val Trp
                595                 600                 605
Lys Tyr Ala Asp Ala Gly His Val Cys His Leu Cys His Pro Asn Cys
                610                 615                 620
Thr Tyr Gly Pro Gly Asn Glu Ser Leu Lys Ala Met Leu Phe Cys Leu
625                 630                 635                 640
Phe Lys Leu Ser Ser Cys Asn Gln Ser Asn Asp Gly Ser Val Ser His
                645                 650                 655
Gln Ser Gly Ser Pro Ala Ala Gln Glu Ser Cys Leu Gly Trp Ile Pro
                660                 665                 670
Ser Leu Leu Pro Ser Glu Phe Gln Leu Gly Trp Gly Gly Cys Ser His
                675                 680                 685
Leu His Ala Trp Pro Ser Ala Ser Val Ile Ile Thr Ala Ser Ser Cys
                690                 695                 700
His
705

<210> SEQ ID NO 2
<211> LENGTH: 2851
<212> TYPE: DNA
<213> ORGANISM: Homo sapiens

<400> SEQUENCE: 2
cccggcgcag cgcggccgca gcagcctccg ccccccgcac ggtgtgagcg cccgccgcgg      60
ccgaggcggc cggagtcccg agctagcccc ggcggccgcc gccgcccaga ccggacgaca     120
ggccacctcg tcggcgtccg cccgagtccc cgcctcgccg ccaacgccac aaccaccgcg     180
cacggccccc tgactccgtc cagtattgat cgggagagcc ggagcgagct cttcggggag     240
cagcgatgcg accctccggg acggccgggg cagcgctcct ggcgctgctg gctgcgctct     300
gcccggcgag tcgggctctg gaggaaaaga agtttgccca aggcacgagt aacaagctca     360
cgcagttggg cacttttgaa gatcattttc tcagcctcca gaggatgttc aataactgtg     420
aggtggtcct tgggaatttg aaattacct atgtgcagag gaattatgat ctttccttct     480
taaagaccat ccaggaggtg gctggttatg tcctcattgc cctcaacaca gtggagcgaa     540
ttcctttgga aaacctgcag atcatcagag gaaatatgta ctacgaaaat tcctatgcct     600
tagcagtctt atctaactat gatgcaaata aaaccggact gaaggagctg cccatgagaa     660
atttacagga atcctgcat ggcgccgtgc ggttcagcaa caaccctgcc ctgtgcaatg     720
tggagagcat ccagtggcgg acatagtca gcagtgactt tctcagcaac atgtcgatgg     780
acttccagaa ccacctgggc agctgccaaa agtgtgatcc aagctgtccc aatgggagct     840 gctgggggtgc aggagaggag aactgccaga aactgaccaa atcatctgt gcccagcagt     900 gctccgggcg ctgccgtggc aagtccccca gtgactgctg ccacaaccag tgtgctgcag     960
gctgcacagg ccccgggag agcgactgcc tggtctgccg caattccga gacgaagcca    1020 cgtgcaagga cacctgcccc ccactcatgc tctacaaccc caccgtac cagatggatg    1080 tgaaccccga gggcaaatac agctttggtg ccacctgcgt gaagaagtgt ccccgtaatt    1140
atgtggtgac agatcacggc tcgtgcgtcc gagcctgtgg ggccgacagc tatgagatgg    1200
```

```
aggaagacgg cgtccgcaag tgtaagaagt gcgaagggcc ttgccgcaaa gtgtgtaacg    1260
gaataggtat tggtgaattt aaagactcac tctccataaa tgctacgaat attaaacact    1320
tcaaaaactg cacctccatc agtggcgatc tccacatcct gccggtggca tttaggggtg    1380
actccttcac acatactcct cctctggatc cacaggaact ggatattctg aaaaccgtaa    1440
aggaaatcac agggtttttg ctgattcagg cttggcctga aacaggacg gacctccatg     1500 cctttgagaa cctagaaatc atacgcggca ggaccaagca acatggtcag ttttctcttg    1560
cagtcgtcag cctgaacata acatccttgg gattacgctc cctcaaggag ataagtgatg    1620
gagatgtgat aatttcagga acaaaaatt tgtgctatgc aaatacaata aactggaaaa     1680
aactgtttgg gacctccggt cagaaaacca aaattataag caacagaggt gaaaacagct    1740
gcaaggccac aggccaggtc tgccatgcct tgtgctcccc cgagggctgc tggggcccgg    1800
agcccaggga ctgcgtctct tgccggaatg tcagccgagg cagggaatgc gtggacaagt    1860
gcaaccttct ggagggtgag ccaagggagt ttgtggagaa ctctgagtgc atacagtgcc    1920
acccagagtg cctgcctcag gccatgaaca tcacctgcac aggacgggga ccagacaact    1980
gtatccagtg tgcccactac attgacggcc cccactgcgt caagacctgc ccggcaggag    2040
tcatgggaga aaacaacacc ctggtctgga agtacgcaga cgccggccat gtgtgccacc    2100
tgtgccatcc aaactgcacc tacgggccag gaaatgagag tctcaaagcc atgttattct    2160 gccttttaa actatcatcc tgtaatcaaa gtaatgatgg cagcgtgtcc caccagagcg      2220
ggagcccagc tgctcaggag tcatgcttag gatggatccc ttctcttctg ccgtcagagt    2280
ttcagctggg ttggggtgga tgcagccacc tccatgcctg gccttctgca tctgtgatca    2340
tcacggcctc ctcctgccac tgagcctcat gccttcacgt gtctgttccc cccgcttttc    2400
ctttctgcca cccctgcacg tgggccgcca ggttcccaag agtatcctac ccatttcctt    2460
ccttccactc cctttgccag tgcctctcac cccaactagt agctaaccat cacccccagg    2520
actgacctct tcctcctcgc tgccagatga ttgttcaaag cacagaattt gtcagaaacc    2580
tgcagggact ccatgctgcc agccttctcc gtaattagca tggccccagt ccatgcttct    2640
agccttggtt ccttctgccc ctctgtttga aattctagag ccagctgtgg gacaattatc    2700
tgtgtcaaaa gccagatgtg aaaacatctc aataacaaac tggctgcttt gttcaatgct    2760
agaacaacgc ctgtcacaga gtagaaactc aaaaatattt gctgagtgaa tgaacaaatg    2820
aataaatgca taataaataa ttaaccacca a                                   2851
```

<210> SEQ ID NO 3
<211> LENGTH: 641
<212> TYPE: PRT
<213> ORGANISM: Homo sapiens

<400> SEQUENCE: 3

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

```
Thr Ile Gln Glu Val Ala Gly Tyr Val Leu Ile Ala Leu Asn Thr Val
                85                  90                  95
Glu Arg Ile Pro Leu Glu Asn Leu Gln Ile Ile Arg Gly Asn Met Tyr
            100                 105                 110
Tyr Glu Asn Ser Tyr Ala Leu Ala Val Leu Ser Asn Tyr Asp Ala Asn
        115                 120                 125
Lys Thr Gly Leu Lys Glu Leu Pro Met Arg Asn Leu Gln Glu Ile Leu
    130                 135                 140
His Gly Ala Val Arg Phe Ser Asn Asn Pro Ala Leu Cys Asn Val Glu
145                 150                 155                 160
Ser Ile Gln Trp Arg Asp Ile Val Ser Ser Asp Phe Leu Ser Asn Met
                165                 170                 175
Ser Met Asp Phe Gln Asn His Leu Gly Ser Cys Gln Lys Cys Asp Pro
            180                 185                 190
Ser Cys Pro Asn Gly Ser Cys Trp Gly Ala Gly Glu Glu Asn Cys Gln
        195                 200                 205
Lys Leu Thr Lys Ile Ile Cys Ala Gln Gln Cys Ser Gly Arg Cys Arg
    210                 215                 220
Gly Lys Ser Pro Ser Asp Cys Cys His Asn Gln Cys Ala Ala Gly Cys
225                 230                 235                 240
Thr Gly Pro Arg Glu Ser Asp Cys Leu Val Cys Arg Lys Phe Arg Asp
                245                 250                 255
Glu Ala Thr Cys Lys Asp Thr Cys Pro Pro Leu Met Leu Tyr Asn Pro
            260                 265                 270
Thr Thr Tyr Gln Met Asp Val Asn Pro Glu Gly Lys Tyr Ser Phe Gly
        275                 280                 285
Ala Thr Cys Val Lys Lys Cys Pro Arg Asn Tyr Val Val Thr Asp His
    290                 295                 300
Gly Ser Cys Val Arg Ala Cys Gly Ala Asp Ser Tyr Glu Met Glu Glu
305                 310                 315                 320
Asp Gly Val Arg Lys Cys Lys Lys Cys Glu Gly Pro Cys Arg Lys Val
                325                 330                 335
Cys Asn Gly Ile Gly Ile Gly Glu Phe Lys Asp Ser Leu Ser Ile Asn
            340                 345                 350
Ala Thr Asn Ile Lys His Phe Lys Asn Cys Thr Ser Ile Ser Gly Asp
        355                 360                 365
Leu His Ile Leu Pro Val Ala Phe Arg Gly Asp Ser Phe Thr His Thr
    370                 375                 380
Pro Pro Leu Asp Pro Gln Glu Leu Asp Ile Leu Lys Thr Val Lys Glu
385                 390                 395                 400
Ile Thr Gly Phe Leu Leu Ile Gln Ala Trp Pro Glu Asn Arg Thr Asp
                405                 410                 415
Leu His Ala Phe Glu Asn Leu Glu Ile Ile Arg Gly Arg Thr Lys Gln
            420                 425                 430
His Gly Gln Phe Ser Leu Ala Val Val Ser Leu Asn Ile Thr Ser Leu
        435                 440                 445
Gly Leu Arg Ser Leu Lys Glu Ile Ser Asp Gly Asp Val Ile Ile Ser
    450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
                485                 490                 495
```

```
Asn Ser Cys Lys Ala Thr Gly Gln Val Cys His Ala Leu Cys Ser Pro
            500                 505                 510
Glu Gly Cys Trp Gly Pro Glu Pro Arg Asp Cys Val Ser Cys Arg Asn
        515                 520                 525
Val Ser Arg Gly Arg Glu Cys Val Asp Lys Cys Asn Leu Leu Glu Gly
    530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
            580                 585                 590
Lys Thr Cys Pro Ala Gly Val Met Gly Glu Asn Asn Thr Leu Val Trp
        595                 600                 605
Lys Tyr Ala Asp Ala Gly His Val Cys His Leu Cys His Pro Asn Cys
    610                 615                 620
Thr Tyr Gly Pro Gly Asn Glu Ser Leu Lys Ala Met Leu Phe Cys Leu
625                 630                 635                 640
Phe

<210> SEQ ID NO 4
<211> LENGTH: 705
<212> TYPE: PRT
<213> ORGANISM: Homo sapiens

<400> SEQUENCE: 4

Met Arg Pro Ser Gly Thr Ala Gly Ala Ala Leu Leu Ala Leu Leu Ala
1               5                   10                  15
Ala Leu Cys Pro Ala Ser Arg Ala Leu Glu Glu Lys Lys Val Cys Gln
            20                  25                  30
Gly Thr Ser Asn Lys Leu Thr Gln Leu Gly Thr Phe Glu Asp His Phe
        35                  40                  45
Leu Ser Leu Gln Arg Met Phe Asn Asn Cys Glu Val Val Leu Gly Asn
    50                  55                  60
Leu Glu Ile Thr Tyr Val Gln Arg Asn Tyr Asp Leu Ser Phe Leu Lys
65                  70                  75                  80
Thr Ile Gln Glu Val Ala Gly Tyr Val Leu Ile Ala Leu Asn Thr Val
                85                  90                  95
Glu Arg Ile Pro Leu Glu Asn Leu Gln Ile Ile Arg Gly Asn Met Tyr
            100                 105                 110
Tyr Glu Asn Ser Tyr Ala Leu Ala Val Leu Ser Asn Tyr Asp Ala Asn
        115                 120                 125
Lys Thr Gly Leu Lys Glu Leu Pro Met Arg Asn Leu Gln Glu Ile Leu
    130                 135                 140
His Gly Ala Val Arg Phe Ser Asn Asn Pro Ala Leu Cys Asn Val Glu
145                 150                 155                 160
Ser Ile Gln Trp Arg Asp Ile Val Ser Ser Asp Phe Leu Ser Asn Met
                165                 170                 175
Ser Met Asp Phe Gln Asn His Leu Gly Ser Cys Gln Lys Cys Asp Pro
            180                 185                 190
Ser Cys Pro Asn Gly Ser Cys Trp Gly Ala Gly Glu Glu Asn Cys Gln
        195                 200                 205
Lys Leu Thr Lys Ile Ile Cys Ala Gln Gln Cys Ser Gly Arg Cys Arg
    210                 215                 220
```

-continued

```
Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
            245                 250                 255

Glu Ala Thr Cys Lys Asp Thr Cys Pro Pro Leu Met Leu Tyr Asn Pro
                260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
                340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
                420                 425                 430

His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
            515                 520                 525

Val Ser Arg Gly Arg Glu Cys Val Asp Lys Cys Asn Leu Leu Glu Gly
            530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
            595                 600                 605

Lys Tyr Ala Asp Ala Gly His Val Cys His Leu Cys His Pro Asn Cys
        610                 615                 620

Thr Tyr Gly Pro Gly Asn Glu Ser Leu Lys Ala Met Leu Phe Cys Leu
625                 630                 635                 640

Phe Lys Leu Ser Ser Cys Asn Gln Ser Asn Asp Gly Ser Val Ser His
```

-continued

```
                645                 650                 655
Arg Ser Gly Ser Pro Ala Ala Gln Glu Ser Cys Leu Gly Trp Ile Pro
        660                 665                 670

Ser Leu Leu Pro Ser Glu Phe Gln Leu Gly Trp Gly Gly Cys Ser His
        675                 680                 685

Leu His Ala Trp Pro Ser Ala Ser Val Ile Ile Thr Ala Ser Ser Cys
        690                 695                 700

His
705

<210> SEQ ID NO 5
<211> LENGTH: 705
<212> TYPE: PRT
<213> ORGANISM: Homo sapiens

<400> SEQUENCE: 5

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300
```

-continued

```
Gly Ser Cys Val Arg Ala Cys Gly Ala Asp Ser Tyr Glu Met Glu Glu
305                 310                 315                 320

Asp Gly Val Arg Lys Cys Lys Cys Glu Gly Pro Cys Arg Lys Val
            325                 330                 335

Cys Asn Gly Ile Gly Ile Gly Glu Phe Lys Asp Ser Leu Ser Ile Asn
                340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Pro Gly Asn Glu Ser Leu Lys Ala Met Leu Phe Cys Leu
625                 630                 635                 640

Phe Lys Leu Ser Ser Cys Asn Gln Ser Asn Asp Gly Ser Val Ser His
                645                 650                 655

Gln Ser Gly Ser Leu Ala Ala Gln Glu Ser Cys Leu Gly Trp Ile Pro
            660                 665                 670

Ser Leu Leu Pro Ser Glu Phe Gln Leu Gly Trp Gly Cys Ser His
        675                 680                 685

Leu His Ala Trp Pro Ser Ala Ser Val Ile Ile Thr Ala Ser Ser Cys
    690                 695                 700

His
705
```

<210> SEQ ID NO 6
<211> LENGTH: 705
<212> TYPE: PRT
<213> ORGANISM: Homo sapiens

<400> SEQUENCE: 6

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
                100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
                180                 185                 190

Ser Cys Pro Asn Gly Ser Cys Trp Gly Ala Gly Glu Glu Asn Cys Gln
            195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
                260                 265                 270

Thr Thr Tyr Gln Met Asp Val Asn Pro Glu Gly Lys Tyr Ser Phe Gly
            275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
                340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
    370                 375                 380

```
Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
            405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
        450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
            485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
            515                 520                 525

Val Ser Arg Gly Arg Glu Cys Val Asp Lys Cys Asn Leu Leu Glu Gly
530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
            565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
            595                 600                 605

Lys Tyr Ala Asp Ala Gly His Val Cys His Leu Cys His Pro Asn Cys
        610                 615                 620

Thr Tyr Gly Pro Gly Asn Glu Ser Leu Lys Ala Met Leu Phe Cys Leu
625                 630                 635                 640

Phe Lys Leu Ser Ser Cys Asn Gln Ser Asn Asp Gly Ser Val Ser His
            645                 650                 655

Gln Ser Gly Ser Pro Ala Ala Gln Glu Ser Cys Leu Gly Trp Ile Pro
            660                 665                 670

Ser Leu Leu Pro Ser Glu Phe Gln Leu Gly Trp Gly Gly Cys Ser His
        675                 680                 685

Leu His Ala Trp Pro Ser Ala Ser Val Ile Ile Thr Ala Ser Phe Cys
        690                 695                 700

His
705

<210> SEQ ID NO 7
<211> LENGTH: 20
<212> TYPE: DNA
<213> ORGANISM: Homo sapiens

<400> SEQUENCE: 7
tcggggagca gcgatgcgac                                               20

<210> SEQ ID NO 8
<211> LENGTH: 20
<212> TYPE: DNA
<213> ORGANISM: Homo sapiens
```

-continued

<400> SEQUENCE: 8
ccattcgttg gacagccttc                                                    20

<210> SEQ ID NO 9
<211> LENGTH: 21
<212> TYPE: DNA
<213> ORGANISM: Homo sapiens

<400> SEQUENCE: 9
gtcatgggag aaaacaacac c                                                  21

<210> SEQ ID NO 10
<211> LENGTH: 20
<212> TYPE: DNA
<213> ORGANISM: Homo sapiens

<400> SEQUENCE: 10
agtaatgatg gcagcgtgtc                                                    20

<210> SEQ ID NO 11
<211> LENGTH: 20
<212> TYPE: DNA
<213> ORGANISM: Homo sapiens

<400> SEQUENCE: 11
tcgctgccag atgattgttc                                                    20

<210> SEQ ID NO 12
<211> LENGTH: 20
<212> TYPE: DNA
<213> ORGANISM: Homo sapiens

<400> SEQUENCE: 12
cgctctggtg ggacacgctg                                                    20

<210> SEQ ID NO 13
<211> LENGTH: 20
<212> TYPE: DNA
<213> ORGANISM: Homo sapiens

<400> SEQUENCE: 13
gaaggaacca aggctagaag                                                    20

<210> SEQ ID NO 14
<211> LENGTH: 17
<212> TYPE: PRT
<213> ORGANISM: Homo sapiens

<400> SEQUENCE: 14

Leu Glu Asn Leu Gln Ile Ile Arg Gly Asn Met Tyr Tyr Glu Asn Ser
1               5                   10                  15

Tyr

<210> SEQ ID NO 15
<211> LENGTH: 23
<212> TYPE: PRT
<213> ORGANISM: Homo sapiens

<400> SEQUENCE: 15

Asp Ser Tyr Glu Asn Ile Glu Glu Asp Gly Val Arg Lys Cys Lys Lys
1               5                   10                  15

Cys Glu Gly Pro Cys Arg Lys

<210> SEQ ID NO 16
<211> LENGTH: 18
<212> TYPE: PRT
<213> ORGANISM: Homo sapiens

<400> SEQUENCE: 16

Phe Arg Gly Asp Ser Phe Thr His Thr Pro Pro Leu Asp Pro Gln Glu
1               5                   10                  15

Leu Asp

<210> SEQ ID NO 17
<211> LENGTH: 12
<212> TYPE: PRT
<213> ORGANISM: Homo sapiens

<400> SEQUENCE: 17

Ile Gln Cys Ala His Tyr Ile Asp Gly Pro His Cys
1               5                   10

<210> SEQ ID NO 18
<211> LENGTH: 31
<212> TYPE: PRT
<213> ORGANISM: Homo sapiens

<400> SEQUENCE: 18

Ser Val Ser His Gln Ser Gly Ser Pro Ala Ala Gln Glu Ser Cys Leu
1               5                   10                  15

Gly Trp Ile Pro Ser Leu Leu Pro Ser Glu Phe Gln Leu Gly Trp
                20                  25                  30

<210> SEQ ID NO 19
<211> LENGTH: 24
<212> TYPE: PRT
<213> ORGANISM: Homo sapiens

<400> SEQUENCE: 19

Gly Gly Cys Ser His Leu His Leu His Ala Trp Pro Ser Ala Ser Val
1               5                   10                  15

Ile Ile Thr Ala Ser Ser Cys His
                20

<210> SEQ ID NO 20
<211> LENGTH: 34
<212> TYPE: PRT
<213> ORGANISM: Homo sapiens

<400> SEQUENCE: 20

Ala Asn Cys Thr Tyr Gly Cys Ala Gly Pro Gly Leu Gln Gly Cys Glu
1               5                   10                  15

Val Trp Pro Ser Gly Tyr Val Glu Trp Gln Trp Ile Leu Lys Thr Phe
                20                  25                  30

Trp Ile

<210> SEQ ID NO 21
<211> LENGTH: 53
<212> TYPE: PRT
<213> ORGANISM: Homo sapiens

<400> SEQUENCE: 21

Gly Pro Asp Asn Cys Ile Gln Cys Ala His Tyr Ile Asp Gly Pro His

-continued

```
                 1               5                  10                 15
Cys Val Lys Thr Cys Pro Ala Gly Val Met Gly Glu Asn Asn Thr Leu
                    20                  25                  30

Val Trp Lys Tyr Ala Asp Ala Gly His Val Cys His Leu Cys His Pro
            35                  40                  45

Asn Cys Thr Tyr Gly
        50

<210> SEQ ID NO 22
<211> LENGTH: 74
<212> TYPE: PRT
<213> ORGANISM: Homo sapiens

<400> SEQUENCE: 22

His Ala Ser Ser Asn Leu Leu Val Ser Arg Pro Gln Cys Ser Gly Asn
1               5                   10                  15

Asp Ser Ala Met His Arg Val Pro Gly Arg Ala Cys Val Val Gln Cys
            20                  25                  30

Cys Thr Ser Gln Gln Glu Gly Arg Gly Thr Lys Glu His Arg Ser Trp
        35                  40                  45

Gln Leu Pro Gln Ser Pro Gly Ala Phe Ala Phe Leu Ser Arg Phe Leu
    50                  55                  60

Arg Leu Thr Trp Gly Leu Ala Val Leu Gln
65                  70

<210> SEQ ID NO 23
<211> LENGTH: 12
<212> TYPE: PRT
<213> ORGANISM: Homo sapiens

<400> SEQUENCE: 23

Phe Leu Arg Leu Thr Trp Gly Leu Ala Val Leu Gln
1               5                   10

<210> SEQ ID NO 24
<211> LENGTH: 4
<212> TYPE: PRT
<213> ORGANISM: Homo sapiens

<400> SEQUENCE: 24

Lys Thr Ile Ile
1

<210> SEQ ID NO 25
<211> LENGTH: 24
<212> TYPE: PRT
<213> ORGANISM: Homo sapiens

<400> SEQUENCE: 25

Cys Ala Ser Val Ser Leu His Gln Tyr Leu Tyr Ile Ser Ile Ser Val
1               5                   10                  15

Ser Val Ser Ile Cys Cys Trp Ala
            20

<210> SEQ ID NO 26
<211> LENGTH: 11
<212> TYPE: PRT
<213> ORGANISM: Homo sapiens

<400> SEQUENCE: 26

Met Cys Asp Tyr Ile Pro Asp Ser Glu Pro Phe
```

-continued

```
1               5                   10

<210> SEQ ID NO 27
<211> LENGTH: 54
<212> TYPE: PRT
<213> ORGANISM: Homo sapiens

<400> SEQUENCE: 27

Ile Tyr Asp Val His Asn Ile Pro Glu Tyr Ile Val Ser Leu Ile Ser
1               5                   10                  15

Gln Met Gly Cys Ile Ala Phe Ser Ile Ser Ile Val Lys Glu Thr Leu
            20                  25                  30

Thr Gly Val Ser Leu Thr Thr Cys Glu Gln Gln His Gln Ser Pro Asp
        35                  40                  45

Tyr Ser Ile Ser Ser Cys
    50

<210> SEQ ID NO 28
<211> LENGTH: 19
<212> TYPE: PRT
<213> ORGANISM: Homo sapiens

<400> SEQUENCE: 28

Trp Asp Val Leu Pro Ser Pro Phe Leu Leu Leu Lys Lys His Leu Gln
1               5                   10                  15

Gly Phe Leu

<210> SEQ ID NO 29
<211> LENGTH: 67
<212> TYPE: PRT
<213> ORGANISM: Homo sapiens

<400> SEQUENCE: 29

Val Thr Glu Gly Leu Ile Ser Val Ser Arg Ser Pro Ser Pro Ser Asp
1               5                   10                  15

Ala Leu Thr Ser Phe Ser Pro Ala Ala Pro Ser Cys His Cys Pro Cys
            20                  25                  30

Pro Ala Ser Leu Gln Gly Ser Thr Gly Leu Pro Phe Pro Thr Ser Leu
        35                  40                  45

Ser Gln Leu Leu Val Ser Asn Pro Tyr Gly Cys Pro Lys Ala Phe Ser
    50                  55                  60

Glu Pro Ala
65

<210> SEQ ID NO 30
<211> LENGTH: 28
<212> TYPE: PRT
<213> ORGANISM: Homo sapiens

<400> SEQUENCE: 30

Pro Val Leu Pro Leu Ser Leu Ser Ser Phe Ser Ser Arg Val Asn Trp
1               5                   10                  15

Ser Thr Phe Pro Tyr Lys Ser Val Thr Ala Ser Cys
            20                  25

<210> SEQ ID NO 31
<211> LENGTH: 78
<212> TYPE: PRT
<213> ORGANISM: Homo sapiens

<400> SEQUENCE: 31
```

```
Pro Gly Asn Glu Ser Leu Lys Ala Met Leu Phe Cys Leu Phe Lys Leu
1               5                   10                  15

Ser Ser Cys Asn Gln Ser Asn Asp Gly Ser Val Ser His Gln Ser Gly
            20                  25                  30

Ser Pro Ala Ala Gln Glu Ser Cys Leu Gly Trp Ile Pro Ser Leu Leu
        35                  40                  45

Pro Ser Glu Phe Gln Leu Gly Trp Gly Gly Cys Ser His Leu His Ala
    50                  55                  60

Trp Pro Ser Ala Ser Val Ile Ile Thr Ala Ser Ser Cys His
65                  70                  75

<210> SEQ ID NO 32
<211> LENGTH: 75
<212> TYPE: PRT
<213> ORGANISM: Homo sapiens

<400> SEQUENCE: 32

Val Ser Ala Gly Leu Gly Trp Met Gln Pro Pro Cys Leu Ala Phe
1               5                   10                  15

Cys Ile Cys Asp His His Gly Leu Leu Leu Pro Leu Ser Leu Met Pro
            20                  25                  30

Ser Arg Val Cys Ser Pro Arg Phe Ser Phe Leu Pro Leu His Val
        35                  40                  45

Gly Arg Gln Val Pro Lys Ser Ile Leu Pro Ile Ser Phe Leu Pro Leu
    50                  55                  60

Pro Leu Pro Val Pro Leu Thr Pro Thr Ser Ser
65                  70                  75

<210> SEQ ID NO 33
<211> LENGTH: 13
<212> TYPE: PRT
<213> ORGANISM: Homo sapiens

<400> SEQUENCE: 33

Cys Thr Gly Pro Gly Leu Glu Gly Cys Pro Thr Asn Gly
1               5                   10

<210> SEQ ID NO 34
<211> LENGTH: 79
<212> TYPE: PRT
<213> ORGANISM: Homo sapiens

<400> SEQUENCE: 34

His Thr Ala Gln Gln Arg Gln Lys Gly Phe Leu Gln His Gln Leu Trp
1               5                   10                  15

Pro Val Cys Gln Ser Lys Ala Leu Arg Lys Ala Arg Leu Lys Ser Leu
            20                  25                  30

Ile Gln Thr His Gln Glu Arg Val Val Leu Leu Ser Met Ala Ser Ser
        35                  40                  45

Gln Glu Ser Trp Asn Thr Tyr Pro Ser Thr Cys Leu Pro Phe Trp Met
    50                  55                  60

Phe Pro Asn Met Asn Gln Thr Ser Arg Pro Leu Cys His Leu Trp
65                  70                  75

<210> SEQ ID NO 35
<211> LENGTH: 19
<212> TYPE: PRT
<213> ORGANISM: Homo sapiens
```

-continued

```
<400> SEQUENCE: 35

Glu Leu Leu Gly His Pro Ala Glu Leu Pro His Ser Thr Leu Gln Ser
1               5                   10                  15

Gln Gly Ser

<210> SEQ ID NO 36
<211> LENGTH: 17
<212> TYPE: PRT
<213> ORGANISM: Homo sapiens

<400> SEQUENCE: 36

Ser Tyr Ile Val Ser His Phe Pro Arg Ser Phe Tyr Lys Met Ser Val
1               5                   10                  15

His

<210> SEQ ID NO 37
<211> LENGTH: 47
<212> TYPE: PRT
<213> ORGANISM: Homo sapiens

<400> SEQUENCE: 37

Pro Lys Ile Pro Ser Ile Ala Thr Gly Met Val Gly Ala Leu Leu Leu
1               5                   10                  15

Leu Leu Val Val Ala Leu Gly Ile Gly Leu Phe Met Arg Arg Arg His
                20                  25                  30

Ile Val Arg Lys Arg Thr Leu Arg Arg Leu Leu Gln Glu Arg Glu
            35                  40                  45

<210> SEQ ID NO 38
<211> LENGTH: 161
<212> TYPE: DNA
<213> ORGANISM: Homo sapiens

<400> SEQUENCE: 38
cagggaccag acaactgtat ccagtgtgcc cactacattg acggccccca ctgcgtcaag     60
acctgcccgg caggagtcat gggagaaaac aacaccctgg tctggaagta cgcagacgcc    120
ggccatgtgt gccacctgtg ccatccaaac tgcacctacg g                        161

<210> SEQ ID NO 39
<211> LENGTH: 230
<212> TYPE: DNA
<213> ORGANISM: Homo sapiens

<400> SEQUENCE: 39
cagccatgcc agtagcaact tgcttgtgag caggcctcag tgcagtggga atgactctgc     60
catgcaccgt gtccccggcc gggccgtgtg ttgtgcaatg ctgcacatca acaggagg      120 gtaggggac aaaagagcac aggtcctggc agctgccaca gtctccaggg gcttttgcgt    180
ttctctccag atttctaagg ttaacatggg gattagctgt tttgcaatga               230

<210> SEQ ID NO 40
<211> LENGTH: 43
<212> TYPE: DNA
<213> ORGANISM: Homo sapiens

<400> SEQUENCE: 40
cagatttcta aggttaacat ggggattagc tgttttgcaa tga                       43

<210> SEQ ID NO 41
```

<211> LENGTH: 19
<212> TYPE: DNA
<213> ORGANISM: Homo sapiens

<400> SEQUENCE: 41
taggaaaaca atcatataa                                                         19

<210> SEQ ID NO 42
<211> LENGTH: 79
<212> TYPE: DNA
<213> ORGANISM: Homo sapiens

<400> SEQUENCE: 42
tagatgtgca tcagtatctc tgcatcaata tctctatatc agtatctctg tgtcagtgag            60
catatgttgc tgggcttag                                                         79

<210> SEQ ID NO 43
<211> LENGTH: 40
<212> TYPE: DNA
<213> ORGANISM: Homo sapiens

<400> SEQUENCE: 43
tagtatgtgt gattacattc ctgattctga gcctttttag                                  40

<210> SEQ ID NO 44
<211> LENGTH: 169
<212> TYPE: DNA
<213> ORGANISM: Homo sapiens

<400> SEQUENCE: 44
gagtatttat gacgtgcaca acattcctga atatattctc tctctcattt ctcagatggg            60
atgtattgcc ttctccattt ctattgttaa agaaacactt acaggggttt ctttaacaac           120
ttgtgaacag cagcatcaga gcccagacta cagcataagc agctgctga                       169

<210> SEQ ID NO 45
<211> LENGTH: 64
<212> TYPE: DNA
<213> ORGANISM: Homo sapiens

<400> SEQUENCE: 45
cagatgggat gtattgcctt ctccatttct attgttaaag aaacacttac aggggtttct            60
ttaa                                                                         64

<210> SEQ ID NO 46
<211> LENGTH: 208
<212> TYPE: DNA
<213> ORGANISM: Homo sapiens

<400> SEQUENCE: 46
cagagttacc gagggcctca tcagcgtcag caggagcccc tcgccttctg acgtctcac             60 atccttctct cctgcagccc cgtcctgcca ctgtccttgt ccagcttctc ttcaagggtc           120
aactggtcta cctttcccta caagtctgtc acagcttctt gttagcaatc cctatggttg          180
cccaaaagca ttttcagagc ctgcataa                                              208

<210> SEQ ID NO 47
<211> LENGTH: 91
<212> TYPE: DNA
<213> ORGANISM: Homo sapiens

<400> SEQUENCE: 47

```
cagccccgtc ctgccactgt ccttgtccag cttctcttca agggtcaact ggtctacctt    60
tccctacaag tctgtcacag cttcttgtta g                                   91

<210> SEQ ID NO 48
<211> LENGTH: 240
<212> TYPE: DNA
<213> ORGANISM: Homo sapiens

<400> SEQUENCE: 48
caggccagga aatgagagtc tcaaagccat gttattctgc cttttttaaac tatcatcctg   60 taatcaaatg aatgatggca gcgtgtccca ccagagcggg agcccagcgc gcaggagtca   120
tgcttaggat ggatcccttc tcttctgccg tcagagtttc agctgggttg gggtggatgc   180
agccacctcc atgcctggcc ttctgcatct gtgatcatca cggcctcctc ctgccactga   240

<210> SEQ ID NO 49
<211> LENGTH: 232
<212> TYPE: DNA
<213> ORGANISM: Homo sapiens

<400> SEQUENCE: 49
cagagtttca gctgggttgg ggtggatgca gccacctcca tgcctggcct tctgcatctg   60
tgatcatcac ggcctcctcc tgccactgag cctcatgcct tcacgtgtct gttcccccccg   120 cttttccttt ctgccacccc tgcacgtggg ccgccaggtt cccaagagta tcctacccat   180
ttccttcctt ccactccctt tgccagtgcc tctcacccca actagtagct aa            232

<210> SEQ ID NO 50
<211> LENGTH: 42
<212> TYPE: DNA
<213> ORGANISM: Homo sapiens

<400> SEQUENCE: 50
cagatgcact gggccaggtc ttgaaggctg tccaacgaat gg                       42

<210> SEQ ID NO 51
<211> LENGTH: 244
<212> TYPE: DNA
<213> ORGANISM: Homo sapiens

<400> SEQUENCE: 51
cagacacact gcccagcaaa ggcaaaaggg cttccttcaa catcagctct ggccagtttg    60
ccagagcaaa gccctgagaa aagcaaggtt gaaaagtctt attcaaactc accaggaaag   120
agtggtgtta ctctcgatgg cgtctagcca ggaatcatgg aattatacac cgagcacctg   180
tttgccattt tggatgtttc caaacatgaa ccaaacttcc aggcccctct gccatctctg   240
gtaa                                                                 244

<210> SEQ ID NO 52
<211> LENGTH: 64
<212> TYPE: DNA
<213> ORGANISM: Homo sapiens

<400> SEQUENCE: 52
cagtgagctg ctaggacacc cagcagaact tccccactcc acactgcaat ctcagggatc    60
ttag                                                                 64

<210> SEQ ID NO 53
```

```
<211> LENGTH: 58
<212> TYPE: DNA
<213> ORGANISM: Homo sapiens

<400> SEQUENCE: 53
tagaagctac atagtgtctc actttccaag atcattctac aagatgtcag tgcactga         58

<210> SEQ ID NO 54
<211> LENGTH: 145
<212> TYPE: DNA
<213> ORGANISM: Homo sapiens

<400> SEQUENCE: 54
caggcctaag atcccgtcca tcgccactgg gatggtgggg gccctcctct tgctgctggt        60
ggtggccctg gggatcggcc tcttcatgcg aaggcgccac atcgttcgga agcgcacgct       120
gcggaggctg ctgcaggaga gggag                                              145
```

SOLUBLE EPIDERMAL GROWTH FACTOR RECEPTOR ISOFORMS

CROSS-REFERENCE TO RELATED APPLICATIONS

This application is a continuation-in-part of U.S. application Ser. No. 09/676,380 filed Sep. 29, 2000, which claims priority to U.S. Application No. 60/157,144 filed Sep. 30, 1999, and U.S. Application No. 60/967,865 filed Sep. 7, 2007.

STATEMENT REGARDING GOVERNMENT RIGHTS

The disclosed invention was made with the support of grants from the National Institutes of Health: K07 CA 76170 "Soluble ErbB1 Molecules as Tumor Biomarkers"; R03 CA82091 "Serologic sErbB1 in Healthy Women"; R21CA82520 "Circulating sErbB1 Levels as Diagnostic Tumor Biomarkers"; R01 CA57534 "Truncated c-erbB Receptors in Women with Ovarian Cancer"; and U01 CA85133 "Early Detection Research Network: National Ovarian Cancer Early Detection Program". The U.S. Government has certain rights in the invention.

FIELD

Embodiments of the present invention relate to soluble isoforms of Epidermal Growth Factor Receptor ("sEGFR"), also known as sErbBl/sHER1, particularly p110 sEGFR, including the nucleic acid sequences encoding these isoforms, purified recombinant proteins, novel antibodies specific for these isoforms, the use of immunoassay and other assay techniques to measure the concentration of these isoform gene products in a biological sample, cancer treatments, and compositions. Additional embodiments of the present invention pertain to p110 sEGFR/sErbB1/sHER1 regulation of at least one ErbB receptor activity and treatment of associated pathological conditions. Other embodiments relate to risk assessment and cancer prevention, screening and early detection, diagnosis, prognosis, theragnosis, monitoring of responsiveness to treatment, and monitoring of disease progression, recurrence, or metastasis of a cancer based on the aberrant concentration of p110 sEGFR gene products (i.e. mRNA or protein) in biological samples.

BACKGROUND

The epidermal growth factor receptor (EGFR) is a transmembrane glycoprotein encoded by the EGFR/ERBB1/HER1 proto-oncogene. Sequence analysis has demonstrated that the human EGFR gene is the cellular homolog of the v-ERBB1 oncogene from the avian erythroblastosis retrovirus (Downward et al., Nature, 307, 521 (1984); Ullrich et al., Nature, 309, 418 (1984)). A family of c-ERBB related cell surface receptor tyrosine kinases has been identified. The four members of the ERBB proto-oncogene family are: ErbBl/EGFR/HER1, ErbB2Neu/HER2 (Coussens et al., Science, 230, 1132 (1988)); ErbB3/HER3 (Kraus et al., Proc. Nat'l. Acad. Sci, USA, 86, 9193 (1989)); Plowman, et al., Proc. Nat'l. Acad. Sci. USA 87, 4905 (1990)); and ErbB4/HER4 (Plowman et al., Proc. Nat'l. Acad. Sci. USA, 90, 1746 (1993)). The Epidermal Growth Factor Receptor (EGFR/ErbBl/HER1) includes three functional domains: an extracellular ligand binding domain, a transmembrane domain, and a cytoplasmic tyrosine kinase domain. The extracellular domain can be further divided into four subdomains (I-IV), including two cysteine-rich regions (II and IV) and two flanking regions (I and III) (Lax et al., Cell Regul. 2,337 (1991)). Subdomains I and III are involved in ligand binding. Ligand binding to the receptor represents the first event in a complex phosphorylation cascade that culminates in DNA synthesis and cell division, as well as cell survival and metastasis.

The full-length 170 kDa human EGFR is encoded by two alternatively spliced transcripts of 5.8 and 10.5 kb (Ullrich et al., supra). In addition, alternatively spliced mRNA's from the EGFR/ErbBl/HER1 gene encode soluble forms of this receptor. A 60 kDa to 80 kDa sEGFR isoform present in human placenta extracts is encoded by an alternatively spliced 1.8 kb RNA transcript (Ilekis et al., Mol. Reprod. Devel., 41, 149 (1995); Reiter and Maihle, Nucl. Acids Res., 24, 4050 (1996)). Soluble EGF receptors also arise from aberrant transcription products in carcinoma-derived cell lines, as exemplified by the epidermoid carcinoma line, A431 (Ullrich et al., supra). In this cell line, the EGFR gene is amplified and rearranged, and a 2.8 kb transcript arises from a translocation between the 5'-region of the EGFR gene and an unidentified region of genomic DNA (Ulrich et al., supra; Merlino et al., Mol. Cell. Biol., 5, 1722 (1985); Hunts et al., Cell Mol. Genet., 11, 477 (1988)). Alternative EGFR/ErbB1 RNA transcripts of approximately 1.8-2.8 kb that encode soluble receptor isoforms comprised of the extracellular ligand binding domain and unique carboxy-terminal amino acid sequences are found in normal human, chicken, rat and mouse tissues (Maihle et al. Proc. Nat'l Acad. Sci. USA, 88, 1825 (1991); Petch et al., Mol. Cell. Biol., 10, 2973 (1990); Flickinger et al., Mol. Cell. Biol., 12,883 (1991); Das et al., Endocrinology 134,971 (1994); Rho et al., Mol. Carcinogenesis. 11, 19 (1994); Reiter and Maihle, Nucl. Acids Res., 24, 4050 (1996); Tong et al., Endocrinology 137,1492 (1996)). Conversely, proteolytically generated isoforms of sEGFR have only been observed in transfected cell lines and human carcinoma cell lines that highly over express the full-length EGF receptor (Brakebusch et al., J. Biol. Chem. 269, 32488 (1994); Zhen et al., Biochemistry 42, 5478 (2003)).

Soluble isoforms of ErbB (sErbB) receptors are being investigated in connection with several human cancers (McKenzie, Biochim. Biophys. Acta, 1072, 193 (1991); Brandt-Rauf Mutat. Res., 333, 203 (1995)). Immunoassay studies show that sErbB2 proteins are elevated in serum samples of patients with breast and ovarian cancer compared to healthy women (Mori et al., Jpn. J. Cancer. Res., 81, 489 (1990); Meden et al., Anticancer Res., 17, 757 (1997)). Recent studies suggest that low pretreatment serum sErbB2 levels are positive predictors of responsiveness to hormonal therapy for patients with metastatic breast cancer (Hayes et al., Breast Cancer Treat., 14, 135, (1993); Leitzel et al., J. Clin. Oncol., 13, 1129 (1995); Yamauchi et al., J. Clin. Oncol., 15, 2518 (1997)). Meden et al. (supra) have reported a positive association between elevated serum p105 sErbB2 levels and shorter survival for patients with stage I through IV epithelial ovarian cancer (EOC).

Immunoassay studies also show that the extracellular domain of EGFR/ErbB1 is detectable and increased in the serum of patients with asbestosis-induced lung cancer (Partanen et al., J. Occup. Med., 36, 1324 (1994); Partanen et al., Int. J. Oncol., 4, 1025 (1994)) and in the urine of patients with squamous cell carcinomas of the head, neck, and lung (Witters et al., Clin. Cancer Res., 1, 551 (1995)). In addition, U.S. Pat. No. 5,674,753, issued Oct. 7, 1997, associates increased levels of the EGFR ectodomain in blood, plasma, or serum with cancer. Ilekis et al. (Gynecol. Oncol., 65, 36 (1997)) have recently observed a positive association between expression of a p60/p80 sEGFR protein and full-length EGFR/ErbB1 in tissue samples of serous cystadenocarcinomas of the ovary. Furthermore, the EGF receptor has been shown to be over-expressed in various human tumor cell lines and neoplasms (Xu et al., Proc, Nat'l. Acad. Sci, 81, 7308 (1984); Salomon et al., Crit. Rev. Oncol. Hematol., 19, 183 (1995)), including cancers of the breast (King et al., Science, 229, 974 (1985)), lung (Hendler et al., Proc. Am. Soc. Clin. Oncol., 8, 223 (1989); Veale et al., Cancer Res., 49, 1313 (1989)), brain (Schlegel et al., Int. J. Cancer, 56, 72 (1994)), bladder (Neal et al., Cancer, 65, 1619 (1990); Mellon et al., 153, 919 (1995)), and ovary (Berchuck et al., Am. J, Obstet. Gynecol., 164, 669 (1991); Scambia et al., J. Clin. Oncol., 10, 529 (1992)).

Research concerning the biological function and clinical utility of EGF/ErbB receptors has provided contradictory results, and has not yet provided a clear indication of how any particular ErbB receptor can be used as a tool for the risk assessment and prevention, screening and early detection, diagnosis, prognosis, theragnosis, and treatment of any particular cancer type. Therefore, a need exists for the isolation and characterization of soluble epidermal growth factor receptor protein molecules and their isoforms in human tissues, and for the analysis/quantitation of these proteins in normal versus pathological conditions. In this regard, a useful, quantitative method to detect the presence of biologically relevant, specific EGF receptor isoform expression in human body fluids and tissues, and for discerning the onset and progression of diseases associated with these soluble epidermal growth factor receptor protein molecules is needed.

SUMMARY

Generally, embodiments of the present invention provide several novel isolated and purified non-genomic nucleic acids which encode soluble isoforms of the human EGFR/ErbB1, as well as nucleic acids encoding engineered variants of these proteins. Preferred embodiments of this aspect of the invention are nucleic acid sequences which specifically encode a soluble isoform of a human EGFR ("sEGFR/sErbB1") whose amino acid sequence comprises the sequence of SEQ ID NO: 1, i.e. p110 sEGFR. The nucleic acid embodiments of the invention include, SEQ ID NO: 2, which is the naturally occurring sequence encoding the polypeptide SEQ ID NO: 1. The nucleic acids of the invention also include nucleic acid sequences which are complementary to or synonymous with SEQ ID NO: 2, (i.e., also encode polypeptide SEQ ID NO: 1.) Other preferred embodiments of this aspect of the invention include nucleic acid sequences which encode proteins which comprise a sequence which has at least 90% identity with SEQ ID NO: 1, more preferably at least 95% identity with SEQ ID NO: 1, more preferably at least 98% identity with SEQ ID NO: 1, and most preferably at least 99% identity with SEQ ID NO: 1. Another embodiment of these nucleic acid sequences would be a nucleic acid encoding the naturally occurring variant SEQ ID NO: 3, which is approximately 90.9% identical to SEQ ID NO: 1 (641 out of 705 amino acids). Other embodiments of these nucleic acid sequences include nucleic acid sequences encoding the point-mutation proteins SEQ ID NO: 4, SEQ ID NO: 5, and SEQ ID NO: 6, which are all approximately 99.8% identical to SEQ ID NO: 1 (704 out of 705 amino acids). Other embodiments of the nucleic acid sequence include nucleic acid sequences which are complementary to the above nucleic acid sequences.

Embodiments of the present invention also provide an expression cassette comprising a nucleic acid sequence encoding p110 sEGFR/sErbB1, which is operably linked to a promoter functional in a host cell. Another aspect of the present invention is a method of producing p110 sEGFR/sErbB1 polypeptides by incorporating such cassettes into expression vectors used to transform prokaryotic or eukaryotic host cells to express a p110 sEGFR/sErbB1 polypeptide. The p110 sEGFR/sErbB1 polypeptide may then be isolated from the host cell or the culture media by methods well known in the protein purification arts. The vectors of the invention also may contain a functional DNA sequence that is comprised of a selectable marker gene and/or reporter gene, as described below, or an additional nucleic acid sequence encoding a polypeptide tag for purification. Another aspect of the present invention is an isolated and purified p110 sEGFR/sErbB1 protein, produced as above. A preferred p110 sEGFR/sErbB1 comprises a polypeptide having SEQ ID NO: 1. sEGFR/sErbB1 can be employed in cell growth assays, ligand binding assays, and biomarker detection assays such as those described in Examples below.

Yet another embodiment of the present invention is antibodies produced using polypeptides which are specific for a protein selected from the group consisting of: SEQ ID NO: 1, SEQ ID NO: 3, SEQ ID NO: 4, SEQ ID NO: 5, and SEQ ID NO: 6; and which do not cross-react with other EGFR/ErbB1 isoforms. For example, polypeptides comprising the unique carboxy-terminus of p110 sEGFR, or portions thereof, are used to generate antibodies specific for p110 sEGFR.

Another embodiment of the present invention is an expression cassette comprising a preselected DNA segment that is complementary to SEQ ID NO: 2 and that is operably linked to a promoter functional in a host cell. Thus, the present invention provides an expression cassette that encodes an "antisense" mRNA transcript of a DNA sequence of the invention. Another aspect of the invention is a method of using this transcript to transform a host cell with an expression cassette comprising the complementary sequence which is expressed within the host cell, and thus altering EGFR and/or sEGFR/sErbB1 expression, adhesion and motility, survival, cell growth, and/or differentiation of the host cell. In addition, such complementary transcripts may be utilized in RNAse protection assays to determine the level of cellular expression of mRNAs encoding SEQ ID NO: 1.

Yet another embodiment of the invention is a sandwich immunoassay method for detecting or determining the concentration of soluble and/or full-length human epidermal growth factor receptor in a biological sample obtained from a patient. The method comprises: a) contacting an amount of a first purified antibody that specifically reacts with a first epitope of the extracellular ligand binding domain of p110 sEGFR/sErbB1 with the patient biological sample to be tested, wherein the first purified antibody is modified with a first labeling moiety, b) contacting the sample with an amount of a second purified antibody that specifically reacts with a second epitope of p110 sEGFR/sErbB1, wherein the second purified antibody is modified with a second labeling moiety, and wherein the second purified antibody does not competitively inhibit the binding of the first purified antibody, and c) determining presence or amount of the soluble epidermal growth factor receptor and/or full-length human epidermal growth factor receptor complexed with said antibodies by detecting the co-presence of the first and second labels. In preferred embodiments of this assay, the first antibody is either MAb R.1 or an antibody which binds to the same epitope as MAb R.1 (i.e. competitively inhibits the binding of MAb R.1 to the ligand binding domain of EGFR/ErbB1). In further preferred embodiments, the second antibody is MAb 528, or an antibody which binds to the same epitope as MAb 528 (i.e., competitively inhibits the binding of MAb 528 to the ligand binding domain of EGFR/ErbB1). In especially preferred embodiments, either the first or second labeling moiety is acridinium. In preferred embodiments of this aspect of the invention the patient biological sample is blood, serum, plasma, urine, saliva, sputum, breast nipple aspirates, tumor lysates or ascites fluid. Additional methods for detecting p110 sEGFR are disclosed in other embodiments.

Embodiments of the invention further provide a method for determining the risk or presence of a cancer, such as for example an ovarian carcinoma in a female human patient. For example, the method comprises a) determining the concentration of p110 sEGFR/sErbB1 in a biological sample obtained from a female patient with ovarian cancer (e.g., by the above immunochemical method) b) comparing the concentration obtained in "a" (above) with a normal or baseline level for p110 sEGFR/sErbB1 that is preferably established with samples from female humans without ovarian cancer, and c) correlating a decrease in the concentration of p110 sEGFR/sErbB1 in the patient's sample with the presence of an ovarian carcinoma in the patient. In further embodiments of this aspect of the invention, a female patient may be monitored with repeated testing to determine the onset or progression of ovarian cancer. In further embodiments, the female patient may be tested before and after radiation, chemotherapy, or surgical treatment to predict treatment responsiveness or survival, and to monitor treatment responsiveness and/or disease regression or progression of ovarian cancer. Additional methods for detecting and quantifying p110 sEGFR are disclosed in other embodiments.

Yet another embodiment of the invention is a method to increase or decrease the half-life of soluble EGFR/ErbB1 ligands in the circulatory system of a human patient. For example, the method may be used to increase the circulatory half-life of ligands, such as EGF and TGF-α, or other soluble receptors (e.g., sHER2) or serum proteins (e.g., extracellular matrix proteins/soluble adhesion proteins) by binding to these proteins in the patient's blood, thereby altering their half-life and/or function in the patient. Alternatively, the method may be used to alter (decrease or extend) the circulatory half-life of these proteins by allowing cells to remove p110 sEGFR/sErbB1-ligand complexes from the circulation by endocytosis and intracellular membrane transport. The method comprises administering to a human patient a ligand-half-life-altering amount of a p110 sEGFR/sErbB1 protein with an amino acid sequence chosen from the group consisting of SEQ ID NO: 1, SEQ ID NO: 3, SEQ ID NO: 4, SEQ ID NO: 5, and SEQ ID NO: 6.

Yet another embodiment of the invention is a method to regulate cellular proliferation and cellular differentiation. The sEGFR/sErbB1 molecules inhibit cytokines and receptors necessary for normal cell proliferation and differentiation and play important roles in regulating development, wound healing, carcinogenesis, and tumor progression. The method comprises administering to a cell a cytokine-function-inhibiting amount of a p110 sEGFR/sErbB1 protein with an amino acid sequence selected from the group consisting of SEQ ID NO: 1, SEQ ID NO: 3, SEQ ID NO: 4, SEQ ID NO: 5, and SEQ ID NO: 6.

Yet another embodiment of the invention is a diagnostic kit package for detecting or determining p110 sEGFR/sErbB1 and/or EGFR concentration in a biological sample. For example, the kit comprises: (a) a solid phase capable of having attached thereto a first antibody; (b) a first antibody that binds to a first epitope on the extracellular ligand binding domain of the human epidermal growth factor receptor, wherein the first antibody is modified with an attachment label moiety; (c) a second antibody which specifically binds to a second epitope on the extracellular ligand binding domain of the human epidermal growth factor receptor, wherein the second antibody is labeled with a second label moiety; and (d) instructions for carrying out the immunoassay of the invention. Preferred kits comprise antibodies specific to a protein having the amino acid sequence SEQ ID NO: 1, SEQ ID NO: 3, SEQ ID NO: 4, SEQ ID NO: 5, or SEQ ID NO: 6.

Various embodiments of the present invention relate to a p110 sEGFR agent for expression of p110 sEGFR or regulation of p110 sEGFR function or expression (either transcription or translation). Examples of a p110 sEGFR agent include without limitation a polypeptide, a nucleic acid sequence (RNA or DNA, sense or antisense), a p110 sEGFR antibody, an expression vector, a small molecule, or a polypeptide agonist or antagonist.

Various embodiments of the present invention pertain to methods for treating cancer comprising a p110 sEGFR agent. Other embodiments relate to p110 sEGFR agents as cancer therapeutics. Other embodiments of the present invention pertain to the use of a p110 sEGFR agent to regulate ErbB receptor signal transduction pathways and biological effects on cellular proliferation, survival, adhesion and motility, differentiation, and metastasis. Embodiments of the present invention also pertain to the risk assessment and prevention, screening, diagnosis, prognosis, theragnosis, treatment, evaluation of responsiveness to treatment, and monitoring of disease progression, recurrence, or metastasis of cancer cells using the p110 sEGFR isoform.

Those and other details, objects, and advantages of the present invention will become better understood or apparent from the following description and drawings showing embodiments thereof.

BRIEF DESCRIPTION OF THE FIGURES AND DEFINITIONS

The accompanying drawings illustrate examples of embodiments of the invention. In such drawings:

FIG. 3 is a schematic representation of alternative exons located in human EGFR introns 15 and 16;

FIG. 4 shows DNA and translated protein sequences (FIGS. 4A and 4B; SEQ ID NOs: 21-54);

Figure 5:
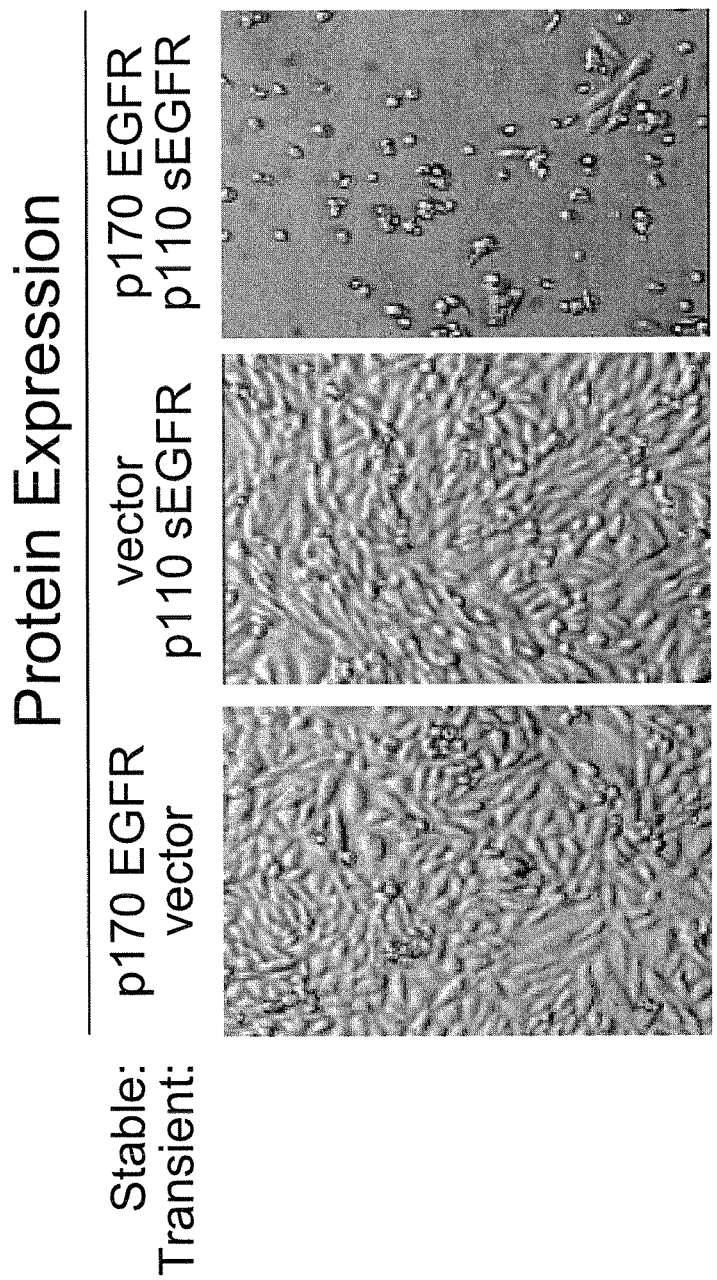

FIG. 5 shows the effects of p110 sEGFR/sErbB1 protein isoform in vitro. Chinese hamster ovary (CHO) cells were transfected with either the full-length human EGFR cDNA (encoding p170 EGFR) in the expression vector pcDNA3 (Invitrogen) or with the vector alone. Stable clonal isolates were selected with G418 and these cells were then transiently transfected with the alternative 3.0 kb EGFR cDNA (encoding p110 sEGFR/sErbB1) or with vector alone. When p170 EGFR and p110 sEGFR/sErbB1 were co-expressed in the same cells, significant cell death was observed 24-48 hours following transfection; however, no cell death was observed when either of these proteins was expressed individually.

Figure 6:
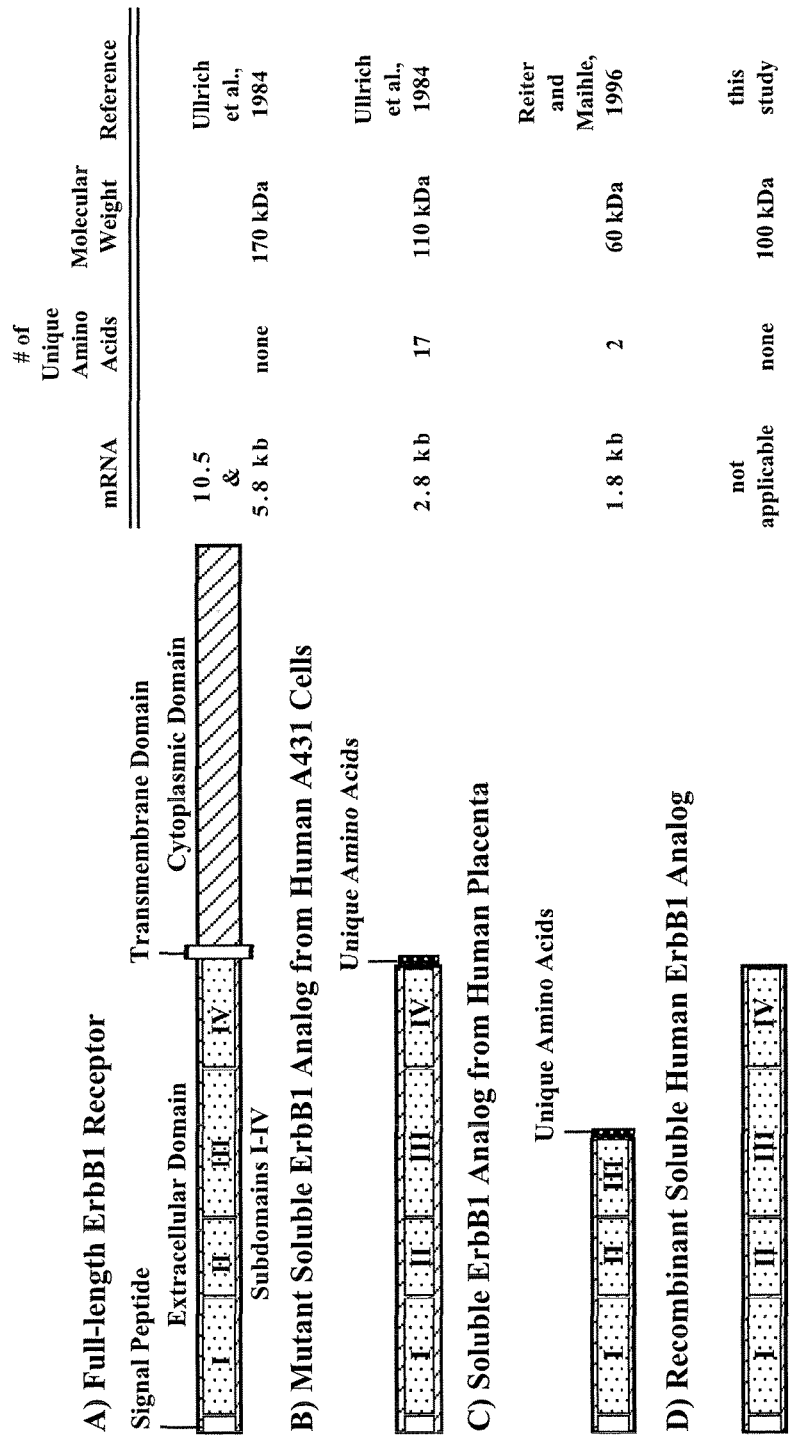

FIG. 6 illustrates the structure of several EGFR isoforms, including the full-length EGF receptor, p170 ErbB1 (A), the mutant p110 soluble ErbB1 analog from A431 cells [which differs in sequence from normal p110 from human placenta, as described below] (B), the p60 soluble ErbB1 analog of human placenta (C), and a recombinant p100 soluble ErbB1 analog (D). Additional information about these molecules is given in the chart. The full-length 170 kDa ErbB1 receptor contains an extracellular domain with four distinct subdomains (I-IV), a transmembrane domain, and a cytoplasmic domain. The mutant A431 p110 sErbB1 analog contains extracellular subdomains I through IV and 17 unique amino acids at its carboxy-terminal end. The p60 sErbB1 analog contains subdomains I and II, a portion of subdomain III, and 2 unique carboxy-terminal amino acids. Recombinant human p100 sErbB1 ends at amino acid 589 (nucleotide numbering according to Ullrich et al., 1984) and, therefore, embodies subdomains I through IV without any additional unique carboxy-terminal amino acids. The mutant p110 and 'natural' p60 human sErbB1 analogs are synthesized from alternatively spliced 2.8 kb and 1.8 kb mRNA transcripts of A431 carcinoma cells and normal placenta, respectively. QT6 cells transfected with the plasmid vector, psErbB1ECD589, synthesize the recombinant human p100 sErbB1 analog. The p110 sEGFR/sErbB1 isoform encoded by the nucleic acids of the invention, not shown, contains subdomains I-IV, as well as its 78 unique amino acid carboxy-end sequence.

Figure 7:
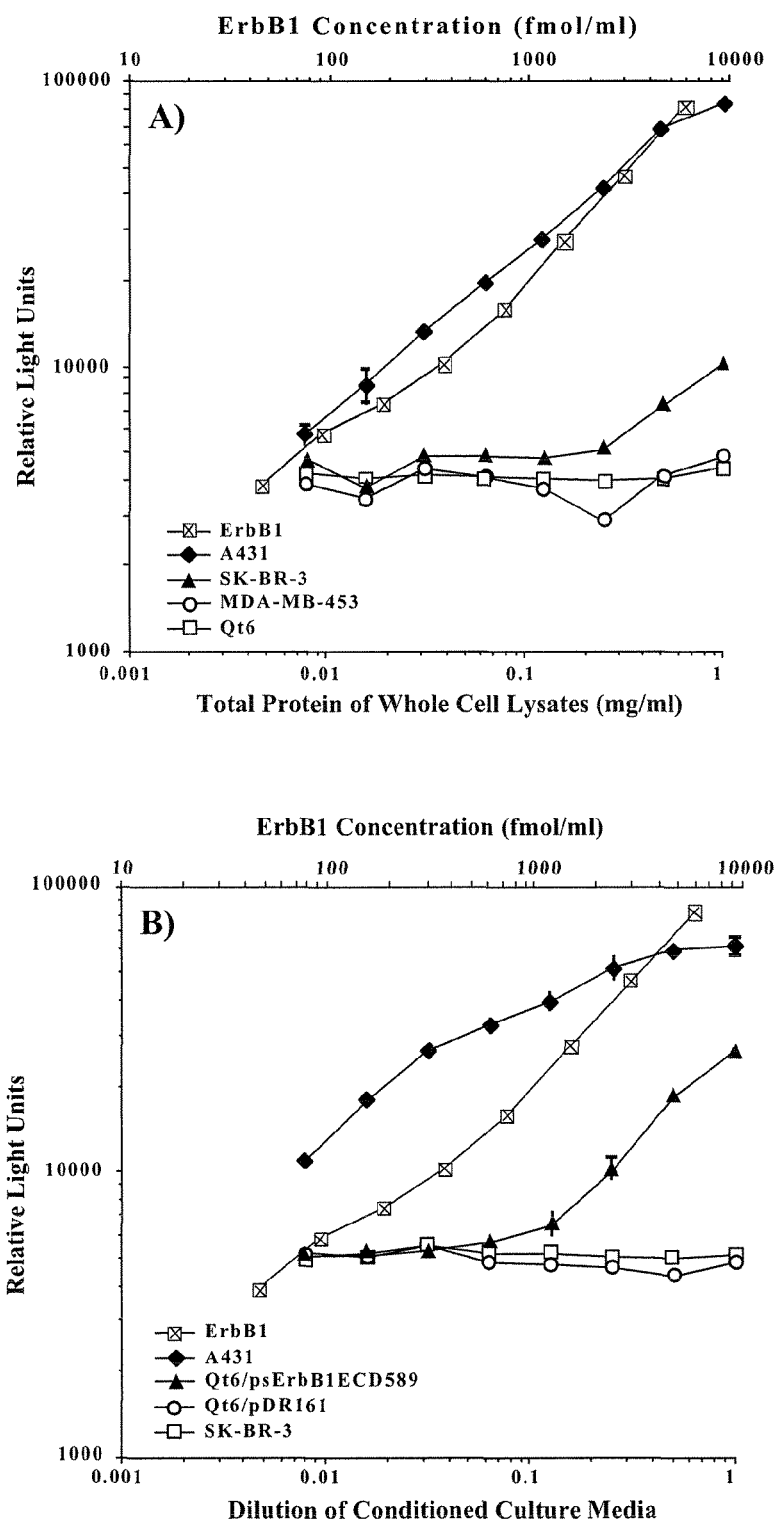

FIG. 7 shows dose-response curves of the ALISA toward whole cell lysates (A) and conditioned culture media (B) from various cell lines that synthesize different combinations of ErbB-related molecules (bottom axes). The standard dose-response curve with p170 ErbBl also is shown on each graph (top axes). QT6 quail fibroblasts do not synthesize any human ErbB molecules. The human breast carcinoma cell line, MDA-MB-453, is known to synthesize full-length ErbB2, ErbB3, and ErbB4, but not ErbB1. The human breast carcinoma cell line, SK-BR-3, is known to synthesize complete ErbB2, ErbB3, and ErbB4 receptors. The dose-response curves with A431 and SK-BR-3 whole cell lysates are positive, and those with MDA-MB-453 and QT6 whole cell lysates are negative (A). A431 cells secrete a mutant p110 sErbB1 analog; whereas QT6, QT6/pDR161, and QT6/psErbB1ECD589 cells secrete no ErbB1-related molecules, p60 sErbB1, and p100 sErbBl, respectively. MDA-MB-453 and SK-BR-3 cells are not known to secrete sErbB1 molecules. However, SK-BR-3 cells have been shown to secrete a sErbB2 analog of approximately 105 kDa. The dose-response curves with A431 and Qt6/psErbB1ECD589 conditioned media are positive, and those with Qt6/pDR161 and SK-BR-3 conditioned media are negative. Thus, as is shown by these graphs, the ALISA described in Example V detects ErbB1 isoforms which contain subdomains I-IV (A431 p110, p100, p170, and p110 sEGFR/sErbB1), but does not detect isoforms which contain only sub domains I-III.

Figure 8:
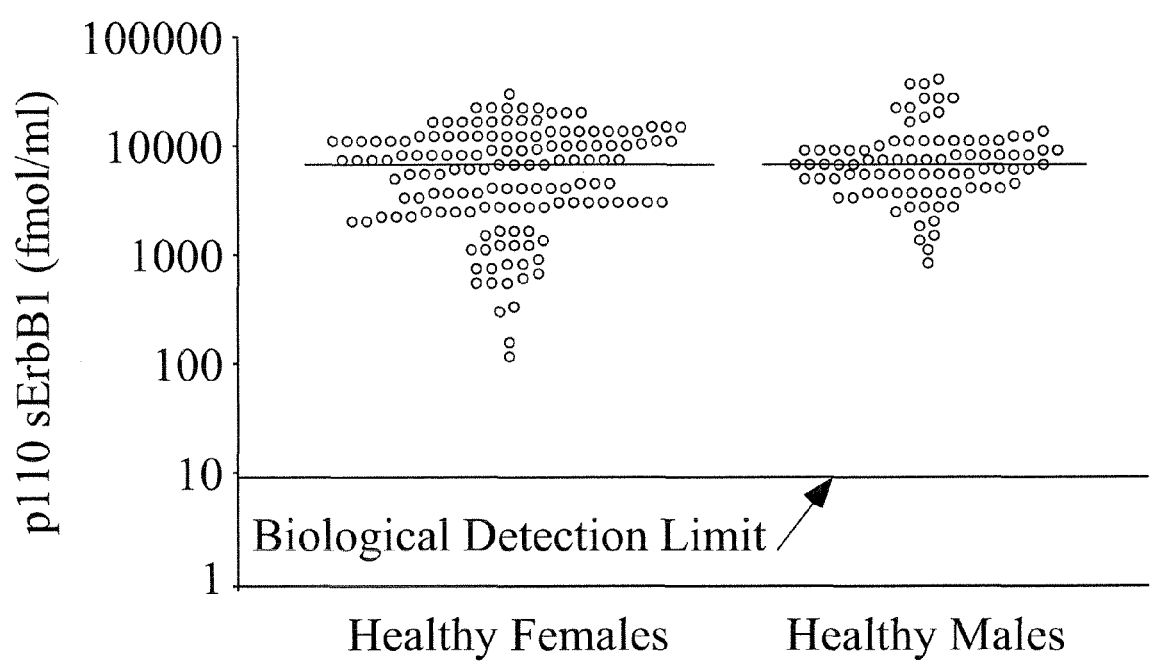

FIG. 8 demonstrates the concentration of sErbB1 in normal human female (n-144) and male (n=88) sera as measured by the ALISA of Example V and compared as described in Example VI.

Figure 9:
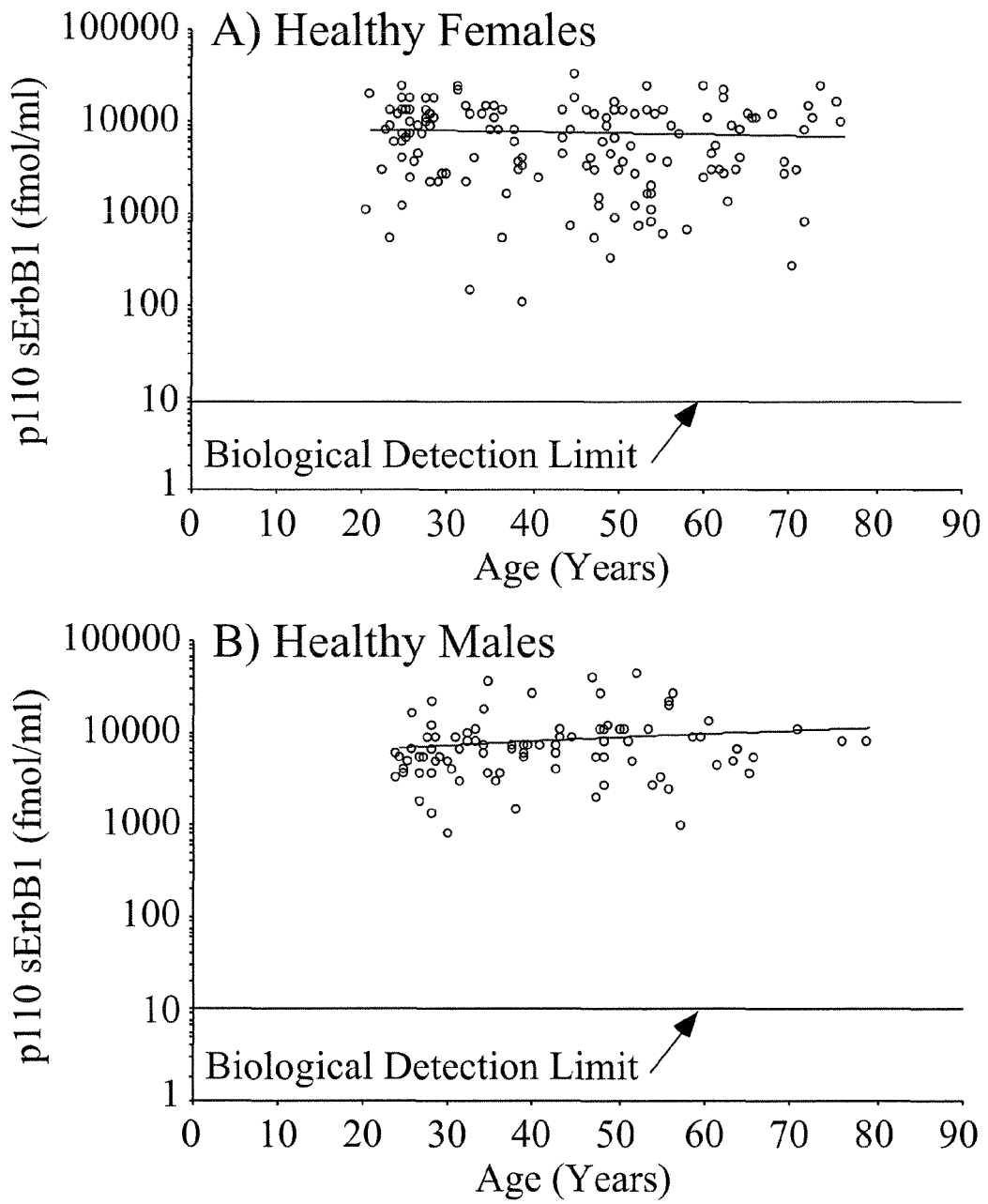

FIG. 9 demonstrates the serum sErbB1 concentrations for healthy females (A) and healthy males (B) plotted as a function of patient age.

Figure 10:
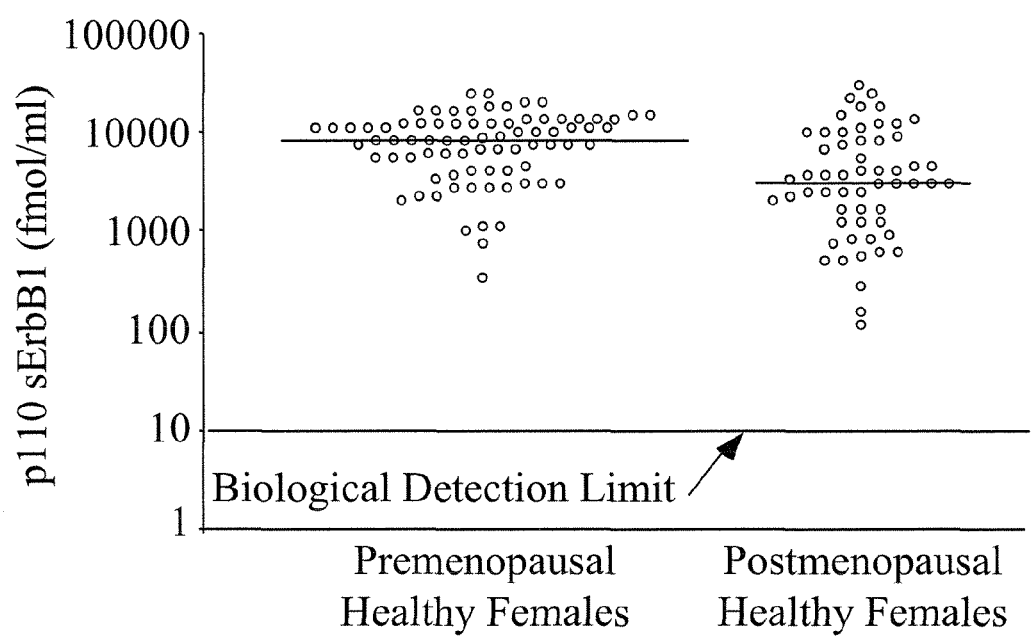

FIG. 10 demonstrates the serum sErbB1 concentrations of the healthy females plotted as a function of pre- or post-menopause status.

Figure 11:
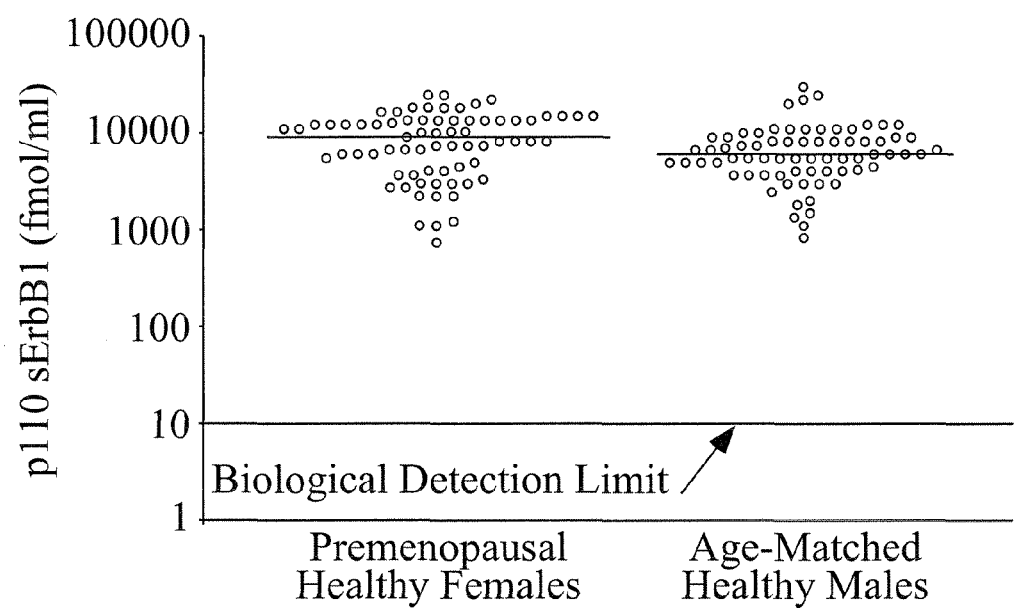

FIG. 11 demonstrates serum sErbB1 concentrations of pre-menopausal females plotted with an age-matched group of males.

Figure 12:
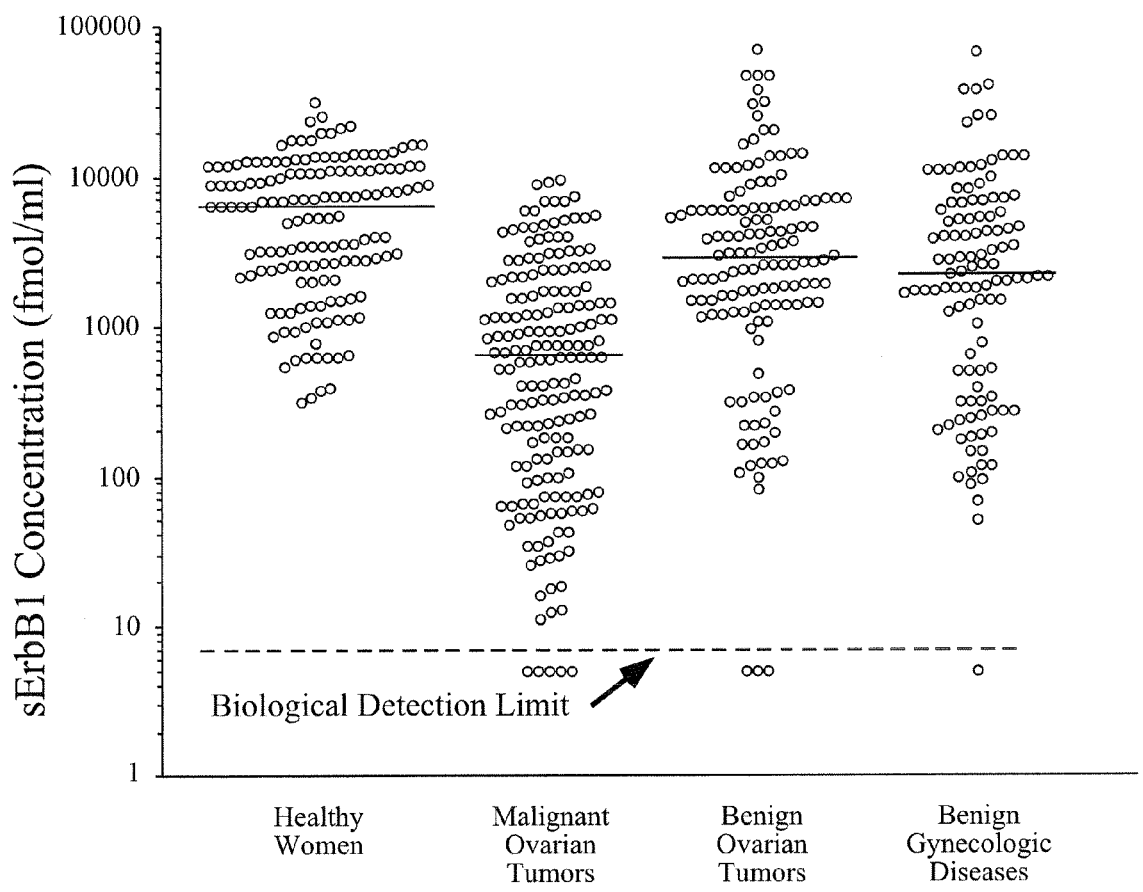

FIG. 12 demonstrates serum sErbB1 concentrations, measured using the ALISA of Example V, of healthy women in a control group, with pre-operative epithelial ovarian cancer (EOC), with benign ovarian tumors, and with benign gynecological diseases. The median sErbB1 concentration of women with EOC is significantly less than that of women without ovarian cancers.

Figure 13:
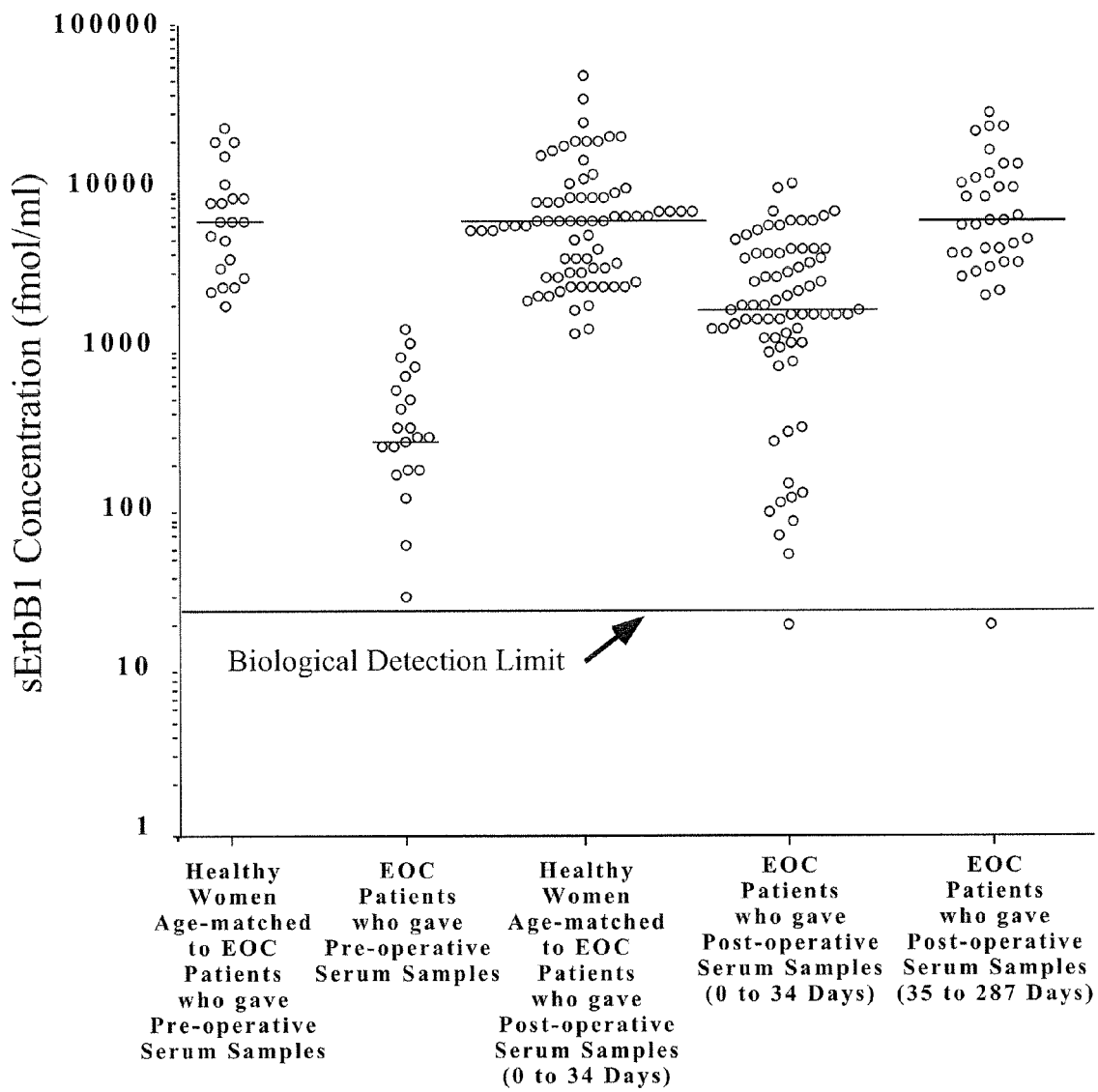

FIG. 13 demonstrates serum sErbB1 concentrations, measured using the ALISA of Example V, of healthy women in a control group age-matched to the pre-operative EOC group, EOC patients who gave pre-operative samples, a control group age-matched to the post-operative EOC group, a post-operative EOC group 0-34 days after surgery, and a post-operative EOC group 35-287 days after surgery.

Figure 14:
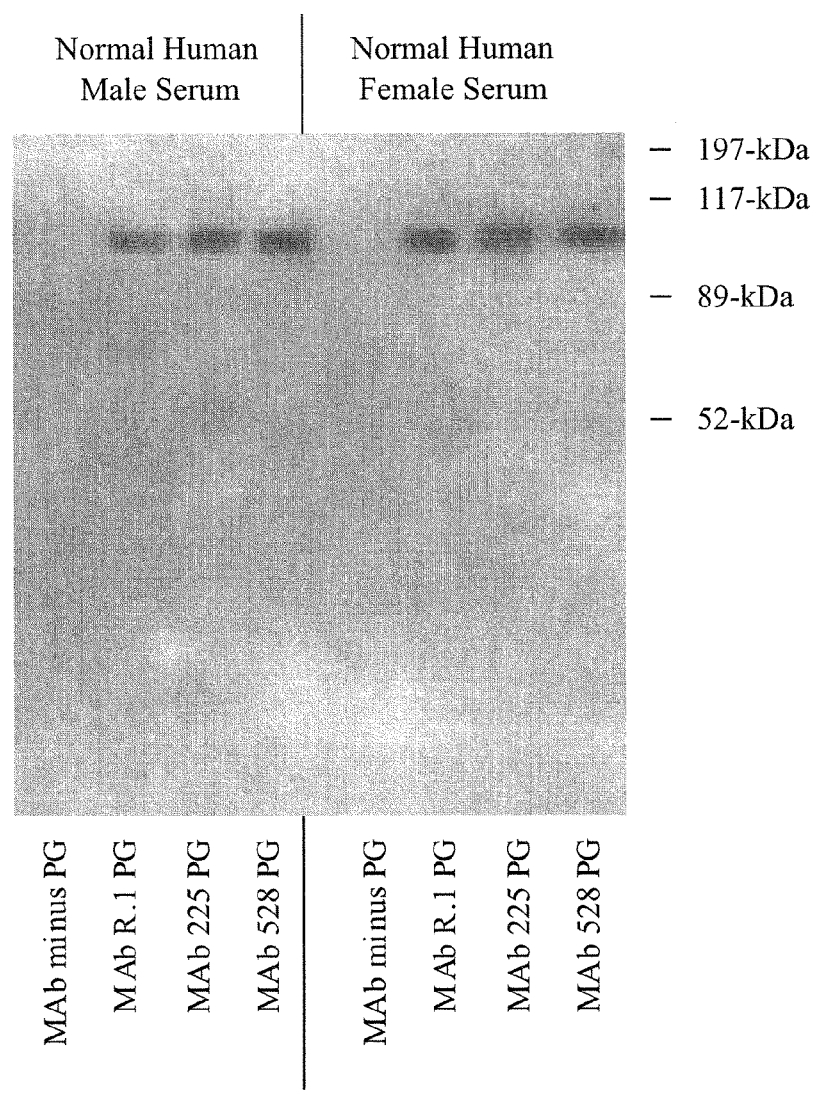

FIG. 14 shows normal human male and female sera immunoprecipitated with Protein-G MAb minus, R.1-, 225-, or 528-coupled resins and Western blotted with a mixture (15E11, 2D2, LA22, and C11) of anti-ErbB1 ECD-specific MAbs. A reactive band of approximately 110 kDa eluted from each MAb affinity resin, but not from the MAb minus resin used to immunoprecipitate normal male or female sera.

Figure 15:
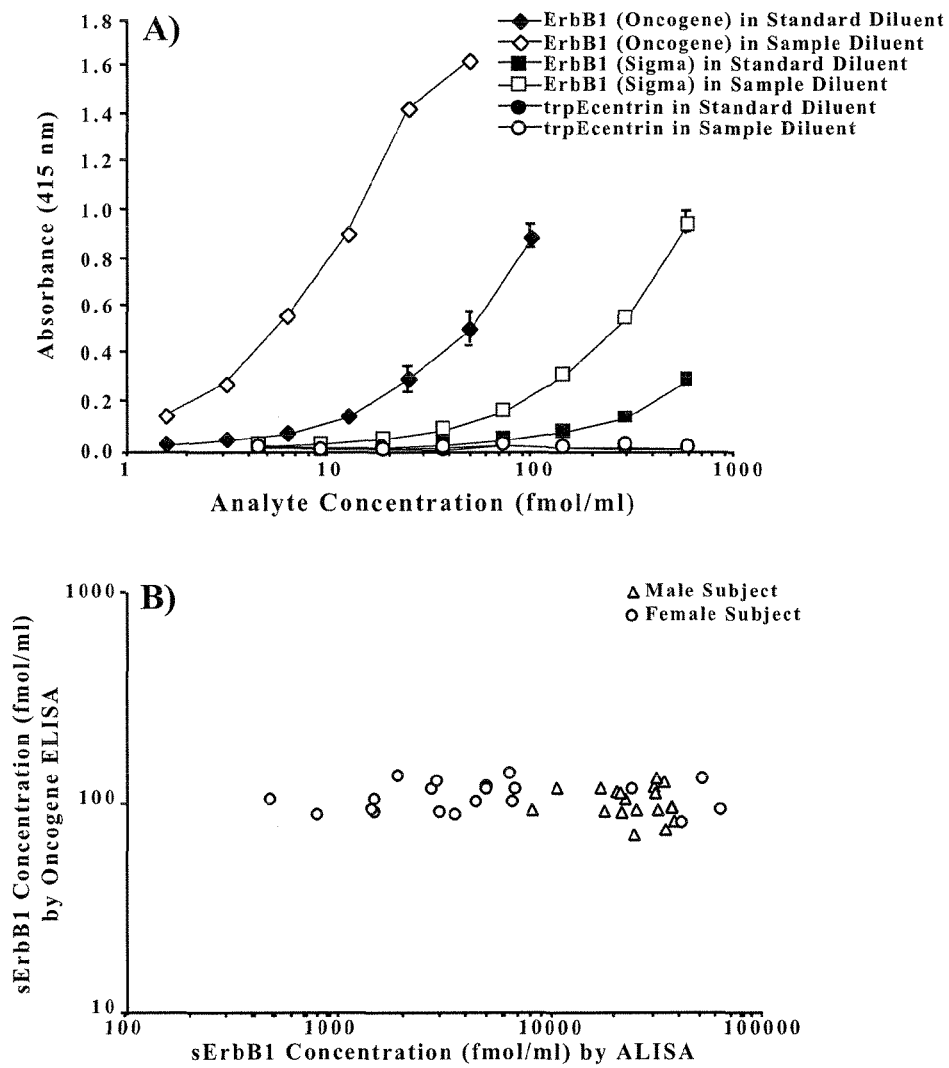

FIG. 15 shows the dose-response curves of the current Oncogene Research Products ELISA with the p170 ErbB1 standard supplied in the Oncogene Research Products kit and with the p170 ErbB1 standard, purchased from Sigma (A). Serial dilutions of both p170 ErbB1 standards and the zero calibrator, trpEcentrin, were prepared and assayed in both standard and sample diluents. Both standards show stronger dose-response curves in the sample diluent than the standard diluent. In addition, the p170 ErbB1 standard supplied by Oncogene Research Products gives stronger response curves than the p170 ErbB1 standard purchased from Sigma Chemical. Serum sErbB1 levels measured with the Oncogene Research Products ELISA for forty healthy human subjects (20 women and 20 men) are compared to the sErbBl levels measured with our ErbB1 ECD-specific ALISA (B). The sErbB1 levels determined with the Oncogene Research Products ELISA for men are not significantly different from those of women. No association between the serum sErbB1 values obtained with the Oncogene Research Products ELISA and those obtained with the ErbB1 ECD-specific ALISA is observed.

Figure 16:
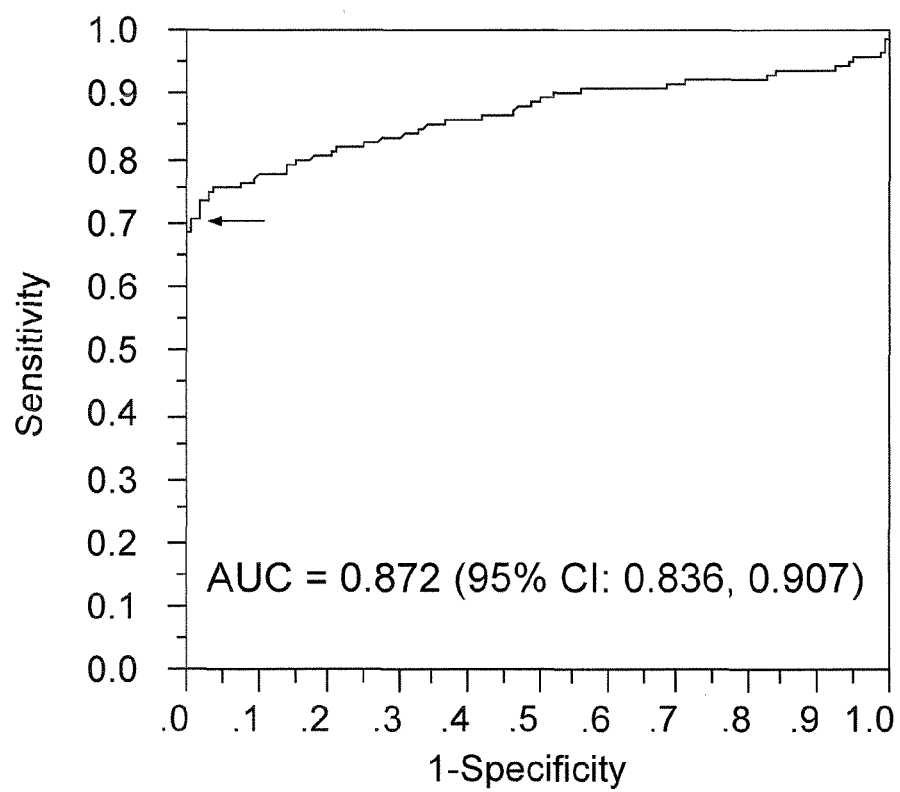

FIG. 16 shows an ROC curve comparing women with EOC versus women with benign ovarian neoplasms for the extended logistic regression model, which includes log p110 sEGFR, log CA125, age, (log sEGFR×log CA125), and (log CA125×age) as continuous variables. The area under the curve (AUC) and 95% confidence interval (95% CI) is provided. The arrow denotes the sensitivity where the model converges to 100% specificity.

Figure 17:
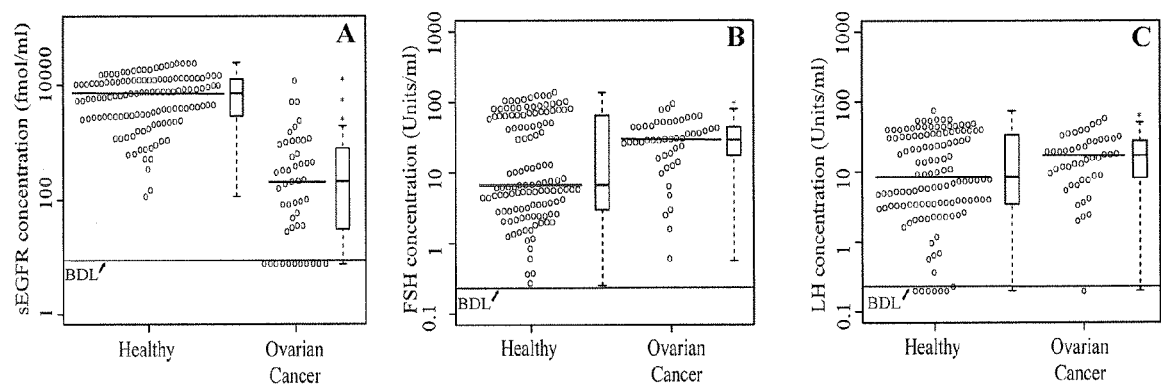

FIG. 17 shows serum p110 sEGFR (A), FSH (B), and LH (C) concentrations for healthy women (n=124) and women with ovarian cancer (n=47). Each data point represents the median value for one serum sample assayed three times in duplicate. Horizontal lines represent the median concentrations of p110 sEGFR, FSH, and LH, respectively, for each group. Horizontal lines in the box plot represent the first, second (median), and third quartiles and whiskers extend from the box to a distance of 1.5 interquartile ranges. Values outside of 1.5 interquartile ranges are indicated by *. The interassay biological detection limit (BDL) for the ALISAs performed in this study are marked as shown.

Figure 18:
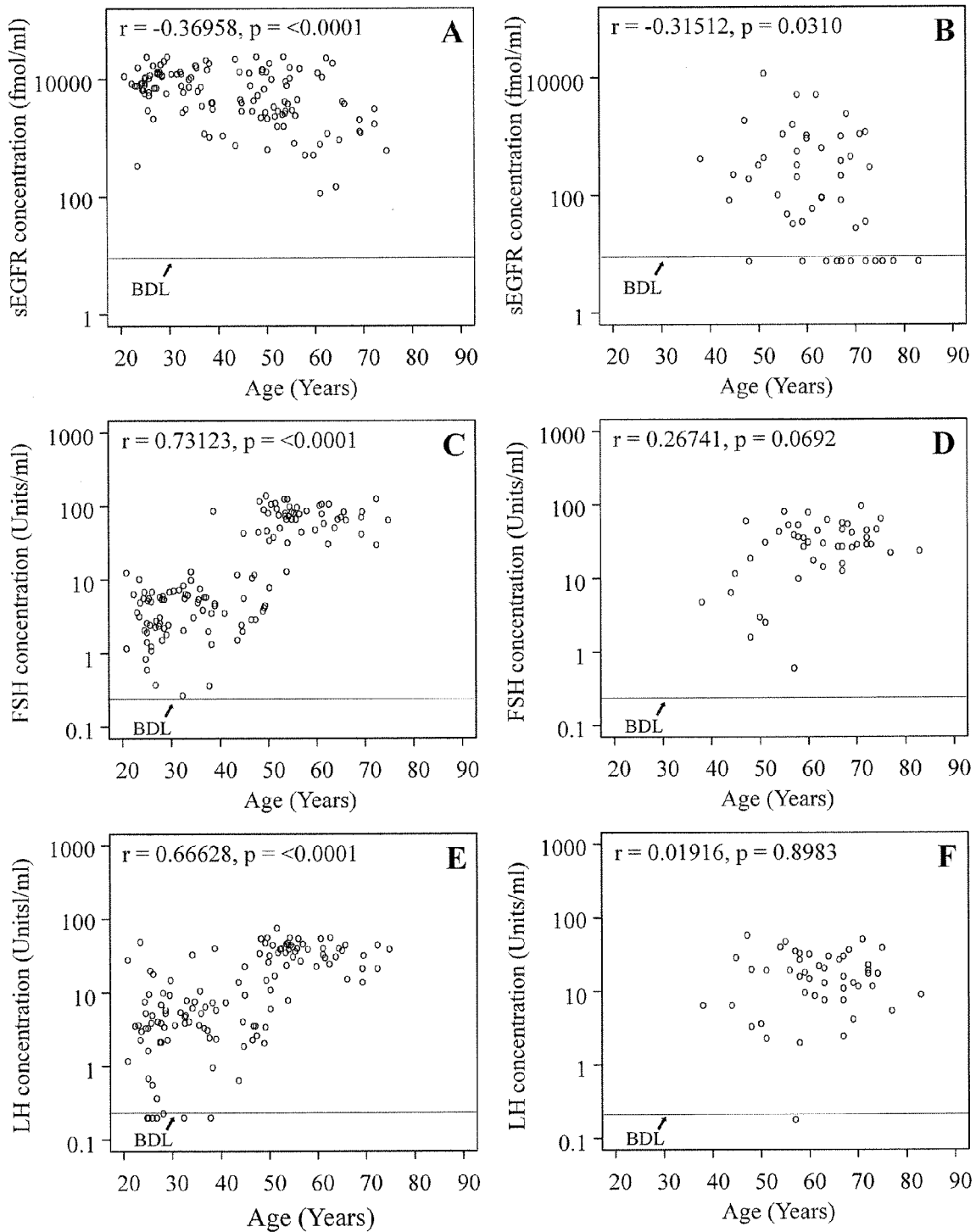

FIG. 18 shows serum p110 sEGFR concentrations in healthy women (A) and women with EOC (B), FSH concentrations in healthy women (C) and women with EOC (D), and LH concentrations in healthy women (E) and women with EOC (F). The biological detection limits (BDL) for the assays used are marked as shown.

Figure 19:
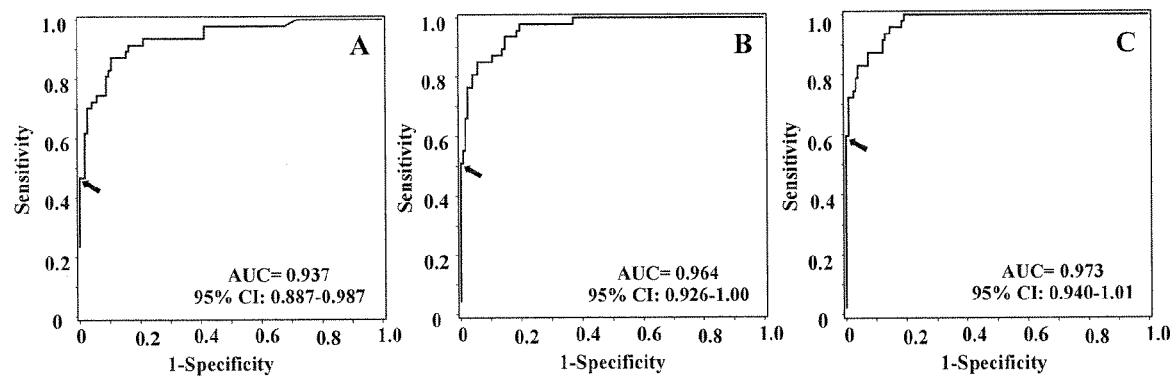

FIG. 19 shows ROC curves comparing log p110 sEGFR concentrations in all healthy women and EOC cases (A) followed by a multivariate logistic regression model (B), which included log p110, log FSH, log LH, age, and menopausal status, and a multivariate model (C), which included log p110, log FSH, log LH, age, menopausal status and all possible interactions. The area under the curve (AUC) and 95% confidence interval (95% CI) is given for each ROC curve. Arrows indicate the sensitivity at which each model converges to 100% specificity.

Figure 20:
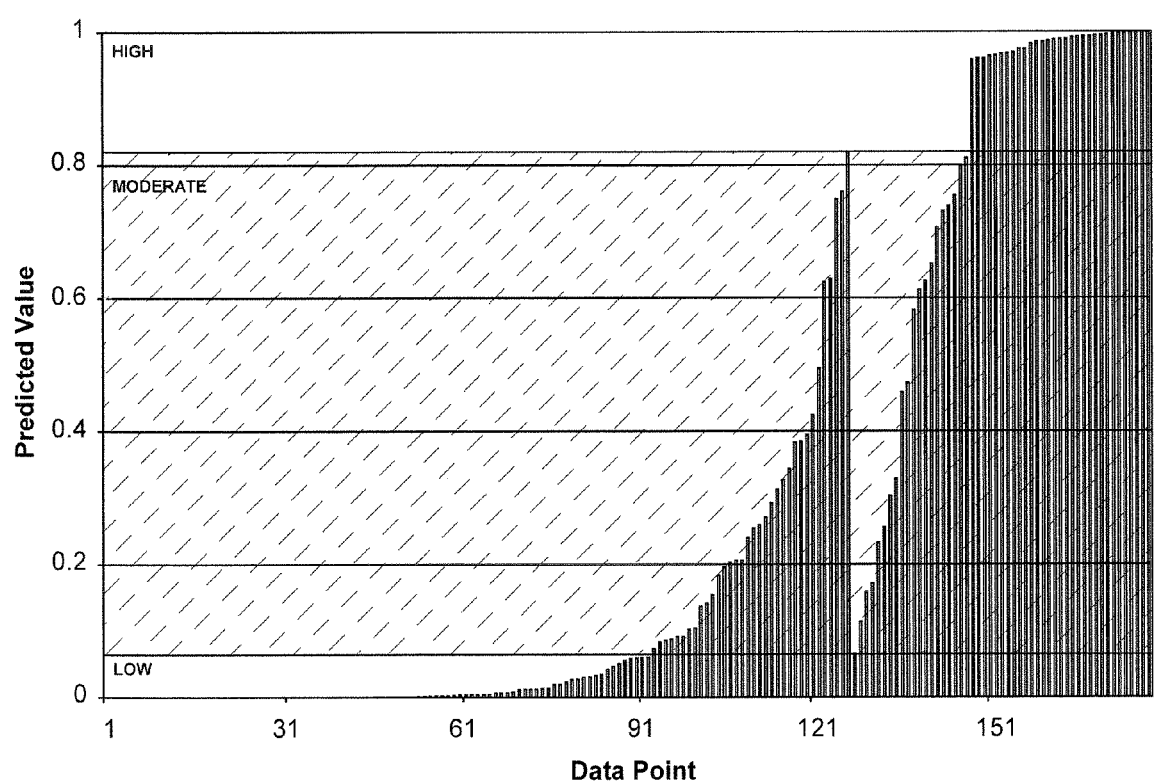

FIG. 20 shows a histogram of predicted probability values in ascending order for each healthy woman (data points 1-124) and each woman with EOC (data points 125-171) derived from the seven-term MLR model (Table 5). Healthy women and women with EOC are predicted to yield a cohort value of 0 or 1, respectively.

Figure 21:
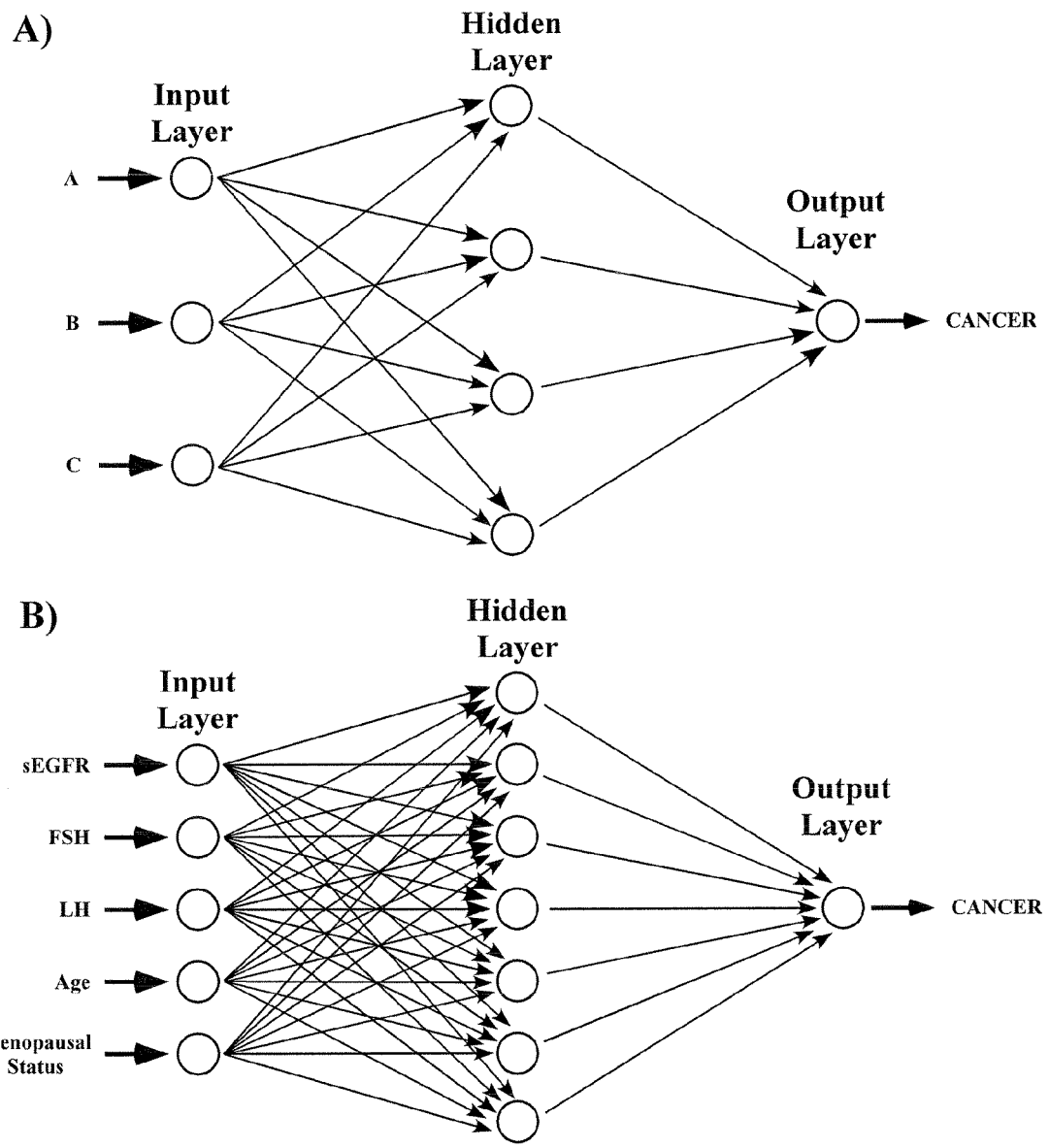

FIG. 21 shows a schematic illustration of a general artificial neural network model with 3:4:1-architecture (A) and a schematic illustration of an artificial neural network model with a 5:7:1-architecture and the input variables sEGFR, FSH, LH, age, and menopausal status (B).

Figure 22:
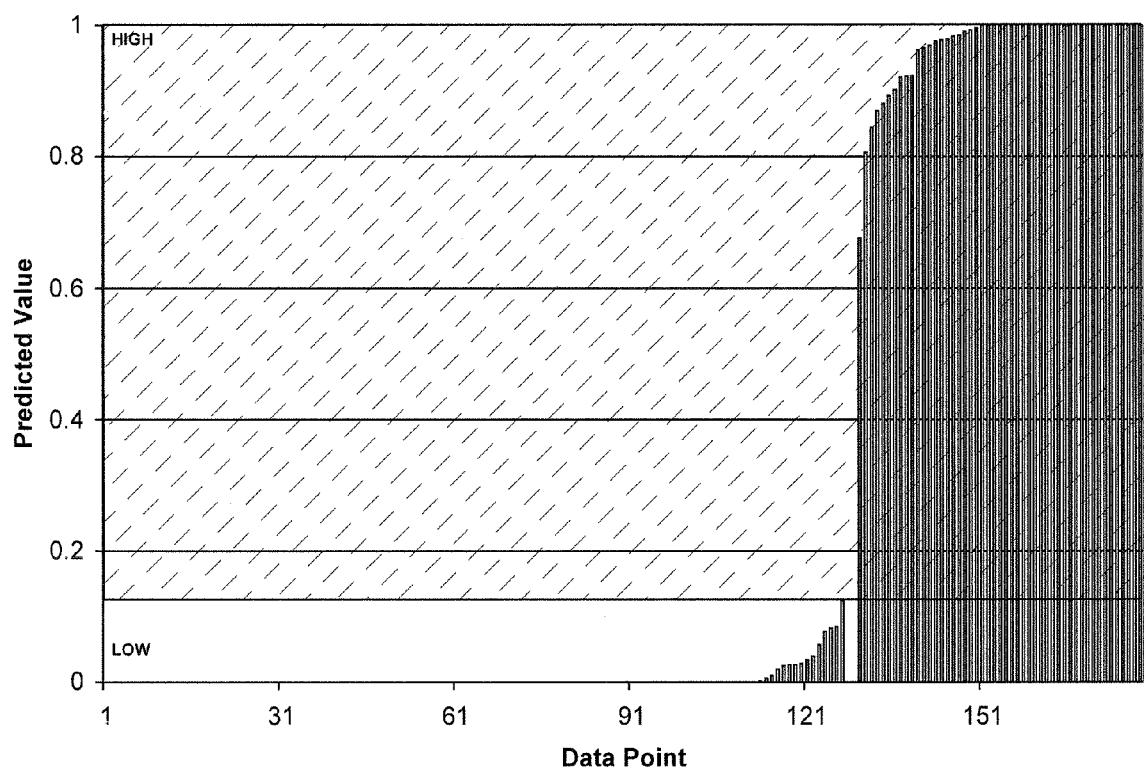

FIG. 22 shows a histogram of predicted probability values in ascending order for each healthy woman (data points 1-127) and each woman with EOC (data points 128-178) derived from a five-term ANN model (see Table 6). Healthy women and women with EOC are predicted to yield a cohort value of 0 (zero) or 1 (one), respectively. Suggested zones of a low and high (gray area) probability of malignancy are shown.

DEFINITIONS

As used herein, the term "soluble" epidermal growth factor receptor (sEGFR or sErbB1) means that the epidermal growth factor receptor polypeptide is found in a form that does not harbor a typical transmembrane domain that is found physically embedded in the lipid bilayer which comprises the cell membrane in the cell of its origin through a constituent peptide domain. However, sEGFR/sErbB1 may be embedded or attached to the cell membrane through other sequences or moieties such as lipids, carbohydrates, and/or proteins. Preferred soluble isoforms of the receptor are synthesized by the cell, proteolytically cleaved from the cell surface or released from the cell by other mechanisms. Other preferred soluble isoforms of the receptor may comprise the extracellular ligand binding domain of the sEGFR/sErbB1, and lack at least a portion of the transmembrane domain (TM), i.e., the canonical membrane-anchoring domain of the EGFR. p110 sEGFR comprises SEQ ID NO: 1 and is based on an apparent molecular weight as determined by SDS polyacrylamide electrophoresis.

As used herein, the terms "isolated and/or purified" refer to in vitro isolation of a nucleic acid or polypeptide molecule from its natural or transformed cellular environment, and from association with other naturally occurring components of the cell. Such molecules may then be sequenced, replicated, manipulated, and/or recombined for artificial in vivo or in vitro expression. Thus, the RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell.

As used herein, the term "biological activity" of a peptide of the invention is defined to mean a polypeptide comprising a subunit of a peptide having SEQ ID NO: 1, or a variant thereof, which has at least about 10%, preferably at least about 50%, and more preferably at least about 90%, of the activity of a peptide having SEQ ID NO: 1. The activity of a peptide of the invention can be measured by methods well known in the art including, but not limited to, the ability to bind EGF, or the ability of the peptide to elicit a sequence-specific immune response when the peptide is administered to an organism, e.g., goat, rabbit, sheep, or mouse.

As used herein with regard to polypeptide sequences, the term "% identity" means the percentage of amino acids in a compared sequence which are identical with the amino acids in a reference sequence, when both sequences are aligned and gaps are introduced, when necessary, to produce the best match. As used herein, sequences with "substantial identity" are at least 90% identical. It is also preferred that the non-identical amino acids in the compared sequence be conservatively substituted with like amino acids in substantially identical polypeptides.

As used herein, the term "complementary," when used to describe nucleic acids, refers to the ability of the nucleic acids to hybridize with each other. Preferred complementary nucleic acids have an exact complementarity with regard to A/T and G/C matching. However, substantially complementary nucleic acids which hybridize to RNA or DNA and remain stably bound under stringent conditions, as defined by methods well known in the art (Sambrook et al., supra), would be sufficiently complementary for some uses (e.g., as antisense nucleotide sequences.)

As used herein, the term "synonymous," when used to describe nucleic acids, refers to the polypeptide sequence encoded by a compared nucleic acid relative to a reference nucleic acid. The genetic code is well known by those of skill in the art, and sequences with codon substitutions which encode the same amino acid can be easily devised for various purposes (e.g., introducing convenient restriction enzyme cleavage sites or optimizing codon usage for a particular recombinant protein production organism) without changing the translated polypeptide sequence. Utilizing common tools such as phosphoramidite polynucleotide synthesis and site directed mutagenesis or other recombinant techniques, such substitutions may easily be effected by those of ordinary skill in the art. Thus, sequences which are synonymous with the exemplary nucleotide sequences are also considered to be within the scope of the present invention. However, sequences which do not directly encode the translation of the same protein would not be considered to be "synonymous." Specifically, the full genomic EGFR/ERBB1/HER1 gene is not considered to be synonymous with the nucleic acids of the invention, as the full-length gene can encode many alternatively spliced transcripts, including the nucleic acids of the invention, but the full-length transcript does not directly encode proteins such as SEQ ID NO: 1.

The terms "recombinant nucleic acid" or "preselected nucleic acid," e.g., "recombinant DNA sequence or segment" or "preselected DNA sequence or segment" refer to a nucleic acid sequence that has been derived or isolated from any appropriate tissue source and that may be subsequently chemically altered, typically in vitro, so that its sequence is not naturally occurring, or corresponds to naturally occurring sequences that are not positioned as they would be positioned in a genome which has not been transformed with exogenous DNA. An example of preselected DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

"Regulatory sequences" is defined to mean RNA or DNA sequences necessary for the expression, post-transcriptional modification, translation, and post-translational modification of an operably linked coding sequence in a particular host organism. The control sequences that are suitable for prokaryotic cells, for example, include a promoter, and optionally an operator sequence, and a ribosome binding site. Eukaryotic cells are known to utilize, for example, promoters, stop sequences, enhancers, splicing, and polyadenylation signal sequences, as well as glycosylation and secretory signal sequences.

"Operably linked" is defined to mean that nucleic acids are placed in a functional relationship with one another in a nucleic acid sequence. For example, DNA for a secretory leader is operably linked to DNA for a polypeptide if it is expressed as a pro-polypeptide that participates in the secretion of the polypeptide; a promoter or enhancer is operably linked to a coding sequence if it affects the transcription of the sequence; or a ribosome binding site is operably linked to a coding sequence if it is positioned to facilitate translation. Generally, "operably linked" means that the DNA sequences being linked are contiguous and, in the case of a secretory leader, contiguous and in reading phase. However enhancers do not have to be contiguous. Linking is accomplished by ligation at convenient restriction sites. If such sites do not exist, the synthetic oligonucleotide linkers or mutagenesis are used in accord with conventional practice.

As used herein, the term "cell line" or "host cell" is intended to refer to well-characterized homogenous, biologically pure populations of cells. These cells may be eukaryotic cells that are neoplastic or which have been "immortalized" in vitro by methods known in the art, as well as primary cells, or prokaryotic cells. The cell line or host cell is preferably of mammalian origin, but cell lines or host cells of non-mammalian origin may be employed, including avian, plant, insect, yeast, fungal or bacterial sources. Generally, the preselected DNA sequence is related to a DNA sequence that is resident in the genome of the host cell but is not expressed, or not highly expressed, or, alternatively, over-expressed.

The terms "transfected" or "transformed" are used herein to include any host cell or cell line, the genome of which has been altered or augmented by the presence of at least one preselected DNA sequence, which DNA is also referred to in the art of genetic engineering as "heterologous DNA," "recombinant DNA," "exogenous DNA," "genetically engineered DNA," "non-native DNA," or "foreign DNA," wherein said DNA was isolated and introduced into the genome of the host cell or cell line by the process of genetic engineering. The host cells of the present invention are typically produced by transfection with a DNA sequence in a plasmid expression vector, a viral expression vector, or as an isolated linear DNA sequence. Preferably, the transfected DNA is a chromosomally integrated recombinant DNA sequence, which comprises a gene encoding p110 sEGFR/sErbB1, which the host cell may or may not express significant levels of autologous or "native" p110 sEGFR/sErbBl.

As used herein, the term "protein" is a polypeptide, and the term "polypeptide" comprises at least two amino acids with no predefined limitation in length, p110 sEGFR/sErbB1 polypeptides may be the complete sequence, for example SEQ ID NO:1, or may be corresponding fragments or variants thereof, such as the unique carboxy terminal region.

DETAILED DESCRIPTION

In order to more fully understand the mechanism by which the sEGFR/sErbB1 influences cell growth and differentiation in normal tissue, cDNAs which encode the extracellular ligand binding domain and unique carboxy-terminal sequences, but not the transmembrane or cytoplasmic kinase domains, of the human epidermal growth factor receptor were isolated from a human placental cDNA library. Besides identifying a soluble isoform of the human epidermal growth factor receptor which may play a role in, or be associated with, cell growth and differentiation in normal cells, the identification and isolation of cDNAs encoding novel p110 sEGFR/sErbB1 transcripts has proven useful for defining the molecular basis for some neoplastic processes. Monoclonal antibodies against the extracellular domain of EGFR produce a useful discriminatory test which demonstrates the association between the discovered forms of sEGFR/sErbB1 and ovarian cancer. By further utilizing the nucleic acid sequences of the invention to recombinantly produce the encoded p110 sEGFRs/sErbBls, or producing specific antibodies to the unique carboxy terminal sequence of these proteins, other important advances in cancer therapeutics, risk assessment, screening and early detection, diagnosis, prognosis and theragnosis may be realized through the invention.

A significant association exists between the concentration of p110 sEGFR/sErbB1 and ovarian cancer. Thus, patient samples, e.g., tissue biopsies, sera or plasma, may now be analyzed with antibodies specific for the p110 sEGFR/sErbB1 to detect the presence and progression of a cancer, for example ovarian carcinomas in patients. As demonstrated by the examples below, the concentration of p110 sEGFR/sErbB1 in patient samples is useful in determining residual disease, responsiveness to chemotherapy, or overall survival. In addition, the concentration of particular isoforms of sEGFR/sErbB1 in a patient may be a useful indicator of the stage, grade, histological and molecular subtype of a tumor. Cancers may include, for example carcinomas, such as esophageal, liver, colon, gastric, thyroid, head and neck, kidney, bladder, pancreatic, lung, skin, breast, ovarian, cervical, endometrial, prostate, brain, intestinal, or testicular, and gliomas.

Molecular genetic based therapies directed to controlling the expression of sEGFR/sErbB1 can be employed to correct, inhibit or supplement the expression of sEGFR/sErbB1 or full-length EGFR in patients with disease. For example, an expression vector containing cDNA encoding sense or anti-sense EGFR/sErbB1 sequences can be introduced into tumors or patients to inhibit or reduce the overexpression of full-length EGFR and/or sEGFR.

The nucleic acid sequences encoding sEGFR/sErbB1 such as SEQ ID NO: 1 also can be employed in expression cassettes to synthesize sEGFR/sErbB1 in vitro. In vitro prepared sEGFR/sErbB1 can be employed to obtain antibodies specific for soluble forms of the EGFR. In vitro synthesized sEGFR/sErbB1 also can be employed in a pharmaceutical formulation which, when administered to a subject, such as a human, can regulate cell functions by interacting with full-length ErbB family members (or other cell surface receptors), the extracellular matrix, and/or ligands thereby suppressing the growth stimulatory and other signaling activities (e.g., adhesion and survival) of ErbB receptor tyrosine kinases.

The sequences of the present invention are useful for detecting the expression of p110 sEGFR/sErbB1, for detecting related DNA molecules and for amplifying nucleic acid sequences, wherein said sequences fall within the scope of the present invention. The antibodies of the invention, besides being useful to discriminate between full-length EGFR and other EGFR isoforms and also detect p110 sEGFR/sErbB1 levels in patient samples, and may be useful in vivo to inhibit the natural functions of sEGFR/sErbB1 or other growth regulatory proteins in various disease states.

Sources and Isolation of Nucleic Acids Encoding p110 sEGFR/ErbB1

Sources of nucleotide sequences from which the present cDNA molecules encoding human sEGFR/sErbB1 can be derived include total or polyA+ RNA from any human cellular source, preferably from embryonic cells such as those from placental tissue, carcinomas, or cell lines derived therefrom, from which cDNAs encoding sEGFR/sErbB1 can be derived by methods known in the art and described below in Example I. Other sources of the DNA molecules of the invention include cDNA libraries derived from any human cellular source including placental cDNA libraries.

A nucleic acid molecule encoding sEGFR/sErbB1 can be identified and isolated using standard methods, as described by Sambrook et al., Molecular Cloning: A Laboratory Manual, Cold Spring Harbor, N.Y. (1989). For example, reverse transcriptase PCR (RT-PCR) can be employed to isolate and clone sEGFR/sErbB1 cDNAs.

Oligo-dT can be employed as a primer in a reverse transcriptase reaction to prepare first-strand cDNAs from isolated RNA that contains RNA sequences of interest, e.g., total RNA isolated from human placental tissue. RNA can be isolated by methods known to the art, e.g., using TRIZOLI™ reagent (GIBCO-BRL/Life Technologies, Gaithersburg, Md.). Resultant first-strand cDNAs are then amplified in PCR reactions.

Primers are made to correspond to highly conserved regions of polypeptides or nucleotide sequences which were identified and compared to generate the primers, e.g., by a sequence comparison of other mammalian or avian EGFRs, particularly sEGFR/sErbB1s. One primer is prepared which is predicted to anneal to the antisense strand, and another primer prepared which is predicted to anneal to the sense strand, of a DNA molecule that encodes a soluble isoform of the human EGFR.

The products of each PCR reaction are separated by an agarose gel and all consistently amplified products are gel purified and cloned directly into a suitable vector, such as a known plasmid vector. The resultant plasmids are subjected to restriction endonuclease and dideoxy sequencing of double-stranded plasmid DNAs.

Another approach to identify, isolate and clone cDNAs that encode sEGFR/sErbB1 is to screen a cDNA library generated from embryonic tissue. Screening for DNA fragments that encode all or a portion of a cDNA encoding sEGFR/sErbB1 can be accomplished by probing the library with a probe, which has sequences that are highly conserved between genes believed to be related to sEGFR/sErbB1, e.g., DNA encoding rat or avian sEGFR/sErbB1 or encoding sEGFR/sErbB1 from A431 cells, or by screening of plaques for binding to antibodies that specifically recognize sEGFR/sErbBl. DNA fragments that bind to a probe having sequences which are related to sEGFR/sErbB1, or which are immunoreactive with antibodies to sEGFR/sErbB1 can be subcloned into a suitable vector and sequenced and/or used as probes to identify other cDNAs encoding all or a portion of sEGFR/sErbB1.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA (Lawn et al., Nucleic Acids Res., 9, 6103 (1981); Goeddel et al., Nucleic Acids Res., 8, 4057 (1980)).

Variants of the DNA Molecules of the Invention

Nucleic acid molecules encoding amino acid sequence variants, including proteins, analogs, and derivatives, of p110 sEGFR are prepared by a variety of methods known in the art. These methods include, but are not limited to, random mutagenesis of DNA which encodes p110 sEGFR or a region thereof, isolation from a natural source (in the case of naturally occurring amino acid sequence variants such as SEQ ID NO: 3-6), preparation by oligonucleotide-mediated (or site-directed) mutagenesis, saturation mutagenesis, PCR mutagenesis, and cassette mutagenesis of an earlier prepared variant or a non-variant version of sEGFR/sErbB1 polypeptide. A library of random amino acid sequence variants can also be generated by the synthesis of a set of degenerate oligonucleotide sequences. Non-random or directed mutagenesis techniques can be used to provide specific sequences or mutations in specific regions. Alanine scanning mutagenesis is a useful method for identification of certain residues or regions of the desired protein that are preferred locations or domains for mutagenesis, see for example Cunningham and Wells (Science 244:1081-1085, 1989). Oligonucleotide-mediated mutagenesis is a useful method for preparing substitution, deletion, and insertion variants of DNA, see, e.g., Adelman et al., (DNA 2:183, 1983). Additionally, in another example, combinatorial mutagenesis is used to generate variants.

Oligonucleotide mediated mutagenesis is a preferred method for preparing amino acid substitution variants of sEGFR/sErbBl. This technique is well known in the art (Adelman et al., DNA, 2, 183 (1983)). Briefly, sEGFR/sErbB1 DNA is altered by hybridizing an oligonucleotide encoding the desired mutation to a DNA template, where the template is the single-stranded form of a plasmid or bacteriophage containing the unaltered or native DNA sequence of sEGFR/sErbB1. After hybridization, a DNA polymerase is used to synthesize an entire second complementary strand of the template that will thus incorporate the oligonucleotide primer, and will code for the selected alteration in the sEGFR/sErbB1 DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art (Crea et al., Proc. Nat'l. Acad. Sci., 75, 5765 (1978)).

The DNA template can be generated by those vectors that are either derived from bacteriophage M13 vectors (the commercially available M13 mp 18 and M13 mp 19 vectors are suitable), or those vectors that contain a single-stranded phage origin of replication as described by Viera et al., Meth. Enzymol., 153, 3 (1987). Thus, the DNA that is to be mutated may be inserted into one of these vectors to generate single-stranded template. Production of the single-stranded template is described in Sections 4.21-4.41 of Sambrook et al., Molecular Cloning Laboratory Manual (Cold Spring Harbor Laboratory Press, N.Y. (1989)). Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the sEGFR/sErbB1, and the other strand (the original template) encodes the native, unaltered sequence of the sEGFR/sErbB1. This heteroduplex molecule is then transformed into a suitable host cell, usually a prokaryote such as E. coli. JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for polypeptide production, generally an expression vector of the type typically employed for transformation of an appropriate host.

The method described immediately above may be modified such that a homoduplex molecule is created wherein both strands of the plasmid contain the mutations(s). The modifications are as follows: The single-stranded oligonucleotide is annealed to the single-stranded template as described above. A mixture of three deoxyribonucleotide triphosphates, deoxyriboadenosine (dATP), deoxyriboguanosine (dGTP), and deoxyribothymidine (dTTP), is combined with a modified thiodeoxyribocytosine called dCTP-(aS) (Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as E. coli JM101.

Embodiments of the present invention further relate to variants of the nucleic acid sequences, such as SEQ ID NO: 2, which encode proteins, analogs or derivatives of p110 sEGFR. Such nucleic acid variants are produced by nucleotide substitutions, deletions, or additions and may involve one or more nucleotides. A preferred embodiment of the invention is an isolated and purified DNA molecule comprising a preselected DNA sequence encoding a sEGFR/sErbB1 polypeptide comprising SEQ ID NO: 2 having nucleotide substitutions which are "silent." That is, when nucleotide substitutions are present in a codon, the same amino acid is encoded by the codon with the nucleotide substitution as is encoded by the codon without the substitution. For example, leucine is encoded by the codon CTT, CTC, CTA and CTG. A variant of SEQ ID NO: 2 at the first codon in the mature polypeptide (CTG in SEQ ID NO: 2) includes the substitution of CTT, CTC or CTA for CTG. Nucleotide substitutions can be introduced into DNA segments by methods well known to the art (Sambrook et al., supra).

In examples, the nucleic acid sequence is a genomic sequence or a cDNA sequence. The nucleotide sequence includes, for example: an sEGFR coding region; a promoter sequence, such as a promoter sequence from an sEGFR gene or from another gene; an enhancer sequence; untranslated regulatory sequences either 5' or 3' from an sEGFR gene or from another gene; a polyadenylation site; and an insulator sequence. The nucleotides of embodiments of the present invention can be modified at the base moiety, sugar moiety or phosphate backbone to improve the stability, hybridization, or solubility of the molecules. For instance, the deoxyribose phosphate backbone of the polynucleotide molecules is modified to generate peptide polynucleotides (see, for example Hyrup et al, Bioorganic & Medicinal Chemistry, 4:523, 1996). As used herein, the terms "peptide polynucleotides" or "PNAs" refer to polynucleotide mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. In examples, PNA oligomers are synthesized using standard solid phase peptide synthesis protocols. PNAs are used in therapeutic and diagnostic applications. For example, PNAs are used as antisense agents for sequence-specific modulation of gene expression.

In other examples, the unique sEGFR sequences are also used as a target for selective inhibition of function/expression (stability, transcription, or translation) using siRNA, RNAi, short hairpin RNA, microRNAs, ribozyme, and triple helix methodologies, as well as antisense sequences, including antisense oligonucleotides. Useful fragments of the sEGFR nucleic acid sequences include antisense or sense oligonucleotides comprising a single-stranded nucleic acid sequence (either RNA or DNA) capable of binding to target sEGFR mRNA or sEGFR DNA sequences. Antisense or sense oligonucleotides comprise a fragment of the coding region of an sEGFR, for example to a unique region such as the C-terminus. Such a fragment generally comprises at least about 5 nucleotides, and typically 14 to 30 nucleotides. The ability to derive an antisense or a sense oligonucleotide, based upon a cDNA sequence encoding a given protein is well known in the art and is described in, for example, Stein and Cohen (Cancer Res. 48:2659, 1988), van der Krol et al. (Bio Techniques 6:958, 1988), Izant J. G. and Weintraub H., (Cell, 36: 100.7-1015, 1984) and Rosenberg et al. (Nature, 313:703-706, 1985).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. Thus, the antisense oligonucleotides are used for example to block expression of sEGFR proteins. Antisense or sense oligonucleotides further comprise oligonucleotides having modified sugar-phosphodiester backbones or other sugar linkages, wherein such sugar linkages are resistant to endogenous nucleases. Such oligonucleotides with resistant sugar linkages are stable in vivo, i.e., capable of resisting enzymatic degradation, but retain sequence specificity to be able to bind to target nucleotide sequences.

Other examples of sense or antisense oligonucleotides include oligonucleotides which are covalently linked to other organic moieties, such as for example organic moieties that increase affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

In other examples, sense or antisense oligonucleotides are introduced into a cell containing the target nucleotide sequence by formation of a conjugate with a ligand binding molecule, for example cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

These sense and antisense nucleic acid sequences have utility as therapeutic agents, in methods of treating cancer or other diseases and medical conditions, and in methods of regulating sEGFR expression and/or function.

The sequences embodied herein relate specifically to p110 sEGFR, for example SEQ ID NO: 1, SEQ ID NO: 2, SEQ ID NO: 3, SEQ ID NO: 4, SEQ ID NO: 5, and SEQ ID NO: 6. Various embodiments relate to the unique carboxy-terminal region of the sEGFR isoforms, for example variants and fragments specific to the unique region comprising amino acids 628-705 of SEQ ID NO: 1.

Chimeric Expression Cassettes and Expression Vectors

The recombinant or preselected DNA sequence or segment used to prepare expression cassettes for transformation may be circular or linear, double-stranded or single-stranded. Generally, the preselected DNA sequence or segment is in the form of chimeric DNA, such as plasmid DNA that can also contain coding regions flanked by control sequences that promote the expression of the preselected DNA present in the resultant cell line. Aside from preselected DNA sequences that serve as transcription units for sEGFR/sErbB1 or portions thereof, a portion of the preselected DNA may be untranscribed, serving a regulatory or a structural function. For example, the preselected DNA may itself comprise a promoter that is active in mammalian cells, or may utilize a promoter already present in the genome that is the transformation target. Such promoters include the CMV promoter, as well as the SV40 late promoter and retroviral LTRs (long terminal repeat elements), although many other promoter elements well known to the art may be employed in the practice of the invention. A preferred promoter useful in the practice of the invention is the CMV promoter. Another preferred promoter useful in the practice of the invention is the Rous Sarcoma Virus LTR promoter.

Other elements functional in the host cells, such as introns, enhancers, polyadenylation sequences and the like, may also be a part of the preselected DNA. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

The preselected DNA to be introduced into the cells further will generally contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as neo, hpt, dhfr, bar, aroA, dapA and the like (Lundquist et al. (U.S. Pat. No. 5,848,956)).

Reporter genes are used for identifying potentially transformed cells and for evaluating the functionality of regulatory sequences. Reporter genes that encode for easily assayable polypeptides are well known in the art. In general, a reporter gene is a gene which is not present in or expressed by the recipient organism or tissue and which encodes a polypeptide whose expression is manifested by some easily detectable property, e.g., enzymatic activity. Preferred genes include the chloramphenicol acetyl transferase gene (cat) from Tn9 of *E. coli*, the beta-glucuronidase gene (gus) of the uidA locus of *E. coli*, and the luciferase gene from firefly *Photinus pyralis*. Expression of the reporter gene is assayed at a suitable time after the DNA has been introduced into the recipient cells.

The general methods for constructing recombinant DNA which can transform target cells are well known to those skilled in the art, and the same compositions and methods of construction may be utilized to produce the DNA useful herein (Sambrook et al., supra).

Other embodiments of the present invention comprise an expression vector containing a nucleic acid sequence that expresses an p110 sEGFR polypeptide, for example a polypeptide having an amino acid sequence comprising SEQ ID NO: 1, in a suitable host. In an example, the nucleic acid sequence has a promoter operably linked to the polypeptide coding region, the promoter being inducible or constitutive and, optionally, cell-type or tissue-specific. In an example, the promoter may also be a heterologous promoter. The vector may be, for example, a plasmid, a single or double-stranded phage vector, or a single or double-stranded viral RNA or DNA molecule. An example of an inducible vector is a vector induced for expression by environmental factors that are easy to manipulate, such as temperature and nutrient additives. Examples of viral vectors include viruses such as baculoviruses, papova viruses such as SV40, vaccinia viruses, adenoviruses including adeno-associated viruses, fowl pox viruses, lentiviruses, parvoviruses, herpes simplex viruses, pseudorabies viruses, and retroviruses, as well as vectors derived from combinations thereof, such as those derived from plasmid and bacteriophage genetic elements, such as cosmids and phagemids.

Transformation into Host Cells and Methods of Delivery

The recombinant DNA can be readily introduced into host cells, e.g., mammalian, bacterial, yeast or insect cells by transfection with an expression vector comprising DNA encoding sEGFR/sErbB1 by any procedure useful for the introduction into a particular cell, e.g., calcium phosphate precipitation, lipofection, electroporation, and the like, to yield a transformed cell having the cDNA stably integrated into its genome, so that the DNA molecules, sequences, or segments of the present invention are expressed by the host cell. That is, an embodiment of the present invention also provides a transformed host cell having a genome augmented by a recombinant (non-native) DNA sequence, preferably by a chromosomally integrated recombinant (genetically engineered) DNA sequence that includes a DNA encoding p110 sEGFR/sErbBl.

Embodiments of the present invention also include therapeutic expression of genetic material, including gene therapy expression of an p110 sEGFR isoform, variant, or fragment. Gene therapy is either by in vivo gene therapy, which is direct delivery of the nucleic acid or nucleic acid-carrying vector into a subject, or ex vivo gene therapy, which is indirect delivery to the subject via transplanted cells that were first transformed with the nucleic acid sequences or nucleic acid-carrying vector in vitro. In examples, viral vectors such as the examples listed herein can be used for in vivo and ex vivo gene therapy.

Plasmid DNA can be delivered with the help of, for example and without limitation: cationic liposomes such as lipofectin, or derivatized (e.g. antibody conjugated) polylysine conjugates, nanoparticles, gramacidin S, artificial viral envelopes or other such intracellular carriers, as well as direct injection of the gene construct or CaPasub.4 precipitation carried out in vitro.

In other examples, a subject polynucleotide is administered using a non-viral delivery vehicle. "Non-viral delivery vehicle" (also referred to herein as "non-viral vector") as used herein is meant to include chemical formulations containing naked or condensed polynucleotides (e.g., a formulation of polynucleotides and cationic compounds, for example dextran sulfate), and naked or condensed polynucleotides mixed with an adjuvant such as a viral particle (i.e., the polynucleotide of interest is not contained within the viral particle, but the transforming formulation is composed of both naked polynucleotides and viral particles, see, for example Curiel et al. 1992 Am. J. Respir. Cell Mol. Biol. 6:247-52). Thus "non-viral delivery vehicle" includes vectors composed of polynucleotides plus viral particles where the viral particles do not contain the polynucleotide of interest. "Non-viral delivery vehicles" include bacterial plasmids, viral genomes or portions thereof, wherein the polynucleotide to be delivered is not encapsidated or contained within a viral particle, and constructs comprising portions of viral genomes and portions of bacterial plasmids and/or bacteriophages. The term also encompasses natural and synthetic polymers and co-polymers. The term further encompasses lipid-based vehicles. Lipid-based vehicles include cationic liposomes such as disclosed for example by Felgner et al (U.S. Pat. Nos. 5,264,618 and 5,459,127; PNAS 84:7413-7417, 1987; Annals N.Y. Acad. Sci. 772:126-139, 1995), DDAB, DOPC, and phospholipids such as phosphatidylcholine. In other examples, lipid based vehicles consist of neutral or negatively charged phospholipids or mixtures thereof including artificial viral envelopes as disclosed for example by Schreier et al. (U.S. Pat. Nos. 5,252,348 and 5,766,625).

Non-viral delivery vehicles include polymer-based carriers, including natural and synthetic polymers and co-polymers. Preferably, the polymers are biodegradable or are readily eliminated from the subject. Naturally occurring polymers include polypeptides and polysaccharides. Synthetic polymers include, but are not limited to, polylysines and polyethyleneimines (PEI; see for example Boussif et al., PNAS 92:7297-7301, 1995) which molecules can also serve as condensing agents. These carriers are dissolved, dispersed or suspended in a dispersion liquid such as water, ethanol, saline solutions and mixtures thereof. A wide variety of synthetic polymers are known in the art.

In examples, naked DNA or RNA molecules are used where they are in a form which is resistant to degradation, such as by modification of the ends, by the formation of circular molecules, or by the use of alternate bonds including phosphothionate and thiophosphoryl modified bonds. In other examples, the delivery of nucleic acids is facilitated by transport where the nucleic acid molecules are conjugated to polylysine or transferrin. Antisense or sense oligonucleotides are introduced into a cell containing the target nucleic acid sequence by any genetic material transfer method, including, for example, CaPO.sub.4-mediated DNA transfection, lipid mediated transfection, electroporation, or by using gene transfer vectors or methods described above. In another example, an antisense or sense oligonucleotide is inserted into a suitable viral vector, such as those described previously. A cell containing the target nucleic acid sequence is contacted with the recombinant viral vector, either in vivo or ex vivo.

p110 sEGFR/sErbB1 Polypeptides

Embodiments of the present invention provide an isolated, purified p110 sEGFR/sErbB1 polypeptides, which can be prepared by recombinant DNA methodologies, and may be fused to other moieties. Additional amino-terminal or carboxy-terminal sequences may be added to the polypeptides for various reasons, for example to improve expression or regulation of expression in particular expression systems, to provide protection against proteolytic cleavage, or to aid in identification as fusion proteins or purification such as affinity chromatography using fusion proteins. Techniques for providing such additional sequences are well known in the art. Furthermore polypeptides with additional amino-terminal or carboxy-terminal sequences may simply result from the technique used to obtain the polypeptide without providing any advantageous characteristics and are also within the scope of the present invention. Whatever sequence is added, the resultant polypeptide preferably exhibits the biological activity of the cognate p110 sEGFR, for example a polypeptide having the amino acid sequence SEQ ID NO: 1.

The polypeptides of the present invention include post-translational modifications, for example and without limitation, phosphorylation, glycosylation and farnesylation.

The general methods for isolating and purifying a recombinantly expressed protein from a host cell are well known to those in the art (Sambrook et al., supra). For example, in one embodiment, the present invention provides the complete amino acid sequence of p110 sEGFR sEGFR/sErbB1 (SEQ ID NO:1), sEGFR/sErbB1 or bioactive variants thereof, which can also be synthesized by the solid phase peptide synthetic method (Stewart et al., Solid Phase Peptide Synthesis, W.H. Freeman Co., San Francisco (1969); Merrifield, T. Am. Chem. Soc., 85, 2149 (1963); Meienhofer, "Hormonal Proteins and Peptides," ed.).

sEGFR/sErbB1 polypeptide expressed in a recombinant cell is purified from recombinant cell proteins or cellular polypeptides to obtain preparations that are substantially homogenous. For example, the culture medium or lysate can be centrifuged to remove particulate cell debris. The membrane and soluble protein fractions are then separated. sEGFR/sErbB1 polypeptide can then be purified from contaminant soluble or membrane proteins and polypeptides by fractionation on immunoaffinity or ion exchange columns; ethanol precipitation; reverse phase HPLC; chromatography on silica or on an anion exchange resin such as DEAE; chromatofocusing; SDS-PAGE; ammonium sulfate precipitation; gel filtration using, e.g., Sephadex G-75; or ligand affinity chromatography, and the like. An example of such purification is provided in Ilekis et al., supra, as well as in Example II herein.

sEGFR/sErbB1 polypeptides, variant sEGFR/sErbB1 polypeptides or biologically active subunits thereof also can be prepared by in vitro transcription and translation reactions. A sEGFR/sErbB1 expression cassette can be employed to generate sEGFR/sErbB1 transcripts that are subsequently translated in vitro so as to result in a preparation of substantially homogenous sEGFR/sErbB1, variant sEGFR/sErbB1, or biologically active subunits thereof. The construction of vectors for use in transcription/translation reactions, as well as the methodologies for such reactions, is well known to the art.

Once isolated from the resulting transgenic host cells or from in vitro transcription/translation reactions, derivatives and chemically derived variants of the sEGFR/sErbB1 polypeptide can be readily prepared. For example, amides of the sEGFR/sErbB1 polypeptides of the present invention may also be prepared by techniques well known in the art for converting a carboxylic acid group or precursor, to an amide. A preferred method for amide formation at the terminal carboxyl group is to cleave the polypeptide from a solid support with an appropriate amine, or to cleave in the presence of an alcohol, yielding an ester, followed by aminolysis with the desired amine.

Salts of carboxyl groups of the sEGFR/sErbB1 polypeptide may be prepared in the usual manner by contacting the peptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of the present polypeptides may be prepared by utilizing an N-acyl protected amino acid for the final condensation, or by acylating a protected or unprotected peptide. O-acyl derivatives may be prepared, for example, by acylation of a free hydroxy peptide or peptide resin. Either acylation may be carried out using standard acylating reagents such as acyl halides, anhydrides, acyl imidazoles, and the like. Both N- and O-acylation may be carried out together, if desired. In addition, the internal sEGFR/sErbB1 amino acid sequence of SEQ ID NO:1 can be modified by substituting one or two conservative amino acids for the positions specified, including substitutions that utilize the D rather than L form.

The invention also is directed to variant or modified forms of the sEGFR/sErbB1 polypeptide. One or more of the residues of this polypeptide can be altered, so long as the variant polypeptide has at least about 50%, preferably at least about 80%, and more preferably at least about 90%, of the biological activity of the polypeptide having SEQ ID NO: 1. Conservative amino acid substitutions are preferred—that is, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids.

Acid addition salts of the polypeptides may be prepared by contacting the polypeptide with one or more equivalents of the desired inorganic or organic acid, such as, for example, hydrochloric acid. Esters of carboxyl groups of the polypeptides may also be prepared by any of the usual methods known in the art.

sEGFR/sErbB1 Variant Polypeptides

Alterations, either conservative or non-conservative, can occur in the amino acid sequence of a polypeptide, which likely do not affect the function. Such alterations include amino acid deletions, insertions, and substitutions. Such alterations can result from alternative splicing and/or the presence of multiple translation start sites and/or stop sites. Polymorphisms may also arise as a result of the infidelity inherent in the translation process. In an example, variant sEGFR/sErbB1 polypeptides have at least one amino acid substitution relative to SEQ ID NO: 1. In particular, amino acids are substituted in a relatively conservative manner. Such conservative substitutions are shown in Table I under the heading of exemplary substitutions. More preferred substitutions are under the heading of preferred substitutions. After the substitutions are introduced, the products are screened for biological activity.

TABLE I

| Original Residue | Exemplary Substitutions | Preferred Substitutions |
|---|---|---|
| Ala (A) | val; leu; ile | val |
| Arg (R) | lys; gin; asn | lys |
| Asn (N) | gln; his; lys; arg | gin |
| Asp (D) | Glu | glu |
| Cys (C) | Ser | ser |
| Gin (Q) | Asn | asn |
| Glu (E) | Asp | asp |
| Gly (G) | Pro | pro |
| His (H) | asn; gln; lys; arg | arg |
| Ile (I) | leu; val; met; ala; phe; norleucine | leu |
| Leu (L) | norleucine; ile; val; met; ala; phe | Ile |
| Lys (K) | arg; gin; asn | arg |
| Met (M) | leu; phe; ile | leu |
| Phe (F) | leu; val; ile; ala | leu |
| Pro (P) | Gly | gly |
| Ser (S) | Thr | thr |
| Thr (T) | Ser | ser |
| Trp (W) | Tyr | tyr |
| Tyr (Y) | trp; phe; thr; ser | phe |
| Val (V) | ile; leu; met; phe; ala; norleucine | leu |

Amino acid substitutions falling within the scope of the invention are, in general, accomplished by selecting substitutions that do not differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic; trp, tyr, phe.

It is preferred that the non-identical amino acids of engineered versions of these embodiments be conservatively substituted relative to the amino acids of SEQ ID NO. 1

Amino acid substitutions or insertions can be made using naturally occurring or non-naturally occurring amino acids; however, L-amino acids are preferred in one embodiment.

Whatever amino acid changes are made, whether by means of substitution, modification, insertion or deletion, polypeptides embodied within embodiments of the present invention have at least 50% sequence identity with the related p110 sEGFR isoform, for example isoforms comprising SEQ ID NO: 1 or SEQ ID NO: 3-6, and in various embodiments the degree of sequence identity is at least 75%. In various embodiments, sequence identities of at least 80%, 85%, 90%, 95%, 98% or 99% are used.

It is also preferred that the proteins of the invention have at least 10% of the biological activity of the polypeptide SEQ. ID NO. 1, more preferably at least 50% of the biological activity of the polypeptide SEQ. ID NO. 1, and most preferably at least 90% of the biological activity of the polypeptide SEQ. ID NO. 1. The activity of the sEGFR/sErbB1 polypeptides of the invention can be measured by methods well known to the art including, but not limited to, ligand binding assays (Flickinger et al., Mol. Cell. Biol., 12, 883 (1992)), the ability of the sEGFR/sErbB1 to be bound by antibodies specific for the extracellular ligand binding domain of EGFR (see Example V, Maihle et al, supra, and Ilekis et al., supra), the ability of the sEGFR/sErbB1 to inhibit the kinase activity of the full-length EGFR, and growth inhibition assays (see Example III). Amino acid substitutions are introduced into the DNA molecules of the invention by methods well known to the art. For example, see the description herein above for the introduction of silent mutations into the DNA molecules of the invention.

Immunogenic Polypeptides, Conjugates, and Antibodies

Because the full amino acid sequence of the p110 sEGFR/sErbB1 has been elucidated by the present invention, the invention also provides polypeptides useful for generating antibodies specific to the proteins encoded by the amino acid sequences of the invention, including SEQ ID NO: 1, SEQ ID NO: 3, SEQ ID NO: 4, SEQ ID NO: 5, and SEQ ID NO: 6. By utilizing a portion of the p110 sEGFR/sErbB1 sequence which contains some of the 78 novel amino acids of the carboxy terminus of the disclosed sEGFR/sErbB1 proteins, antibodies raised to these peptides may be specific for the placental p110 sEGFR/sErbB1, but non-reactive with full-length EGFR or other sEGFR/sErbB1 isoforms such as p60 sEGFR/sErbB1. Thus, polyclonal or monoclonal antibodies particularly useful for detecting p110 sEGFR/sErbB1 in patient samples may be made using the disclosed 78 amino acid sequence. For example, amino acids SSCN QSNDGSVSHQ S (corresponding to amino acids 644-658) or PGNESLKAML FCLFKLSSCN QSNDGSVSHQ S (corresponding to amino acids 628-658).

Polypeptides for use as immunogens will typically be smaller than the full sEGFR/sErbB1 protein, ranging from 10 to about 500 amino acids in length. Although they may contain other amino acids for, e.g., conjugation purposes, the immunogenic polypeptides of the invention comprise an amino acid sequence specific for sEGFR/sErbB1 which is of 10 to 35 amino acids in length, more preferably 11 to 31 amino acids in length, and most preferably 14 to 20 amino acids in length. These lengths of specific sequence are typical of those used in the art for conjugation to immunogenic carrier molecules. The amino acid sequence is identical to an amino acid sequence of similar length in an amino acid sequence selected from the group consisting of: amino acids 628-705 of SEQ ID NO. 1, amino acids 628-705 of SEQ ID NO. 3, amino acids 628-705 of SEQ ID NO. 4, amino acids 628-705 of SEQ ID NO. 5, and amino acids 628-705 of SEQ ID NO. 6. The polypeptides may optionally comprise further portions of the sEGFR/sErbB1 amino acid sequence which are not specific for the p110 sEGFR/sErbB1s, e.g., a peptide encoded by exon15, 15a, and/or 15b of sEGFR/sErbB1.

These polypeptides may be conveniently conjugated to immunostimulatory carrier molecules. Preferred carrier molecules for use as immunogenic conjugates include keyhole limpet hemocyanin (KLH), ovalbumin, and bovine serum albumin (BSA), however, other suitable carriers may be used. Conjugation chemistries for this purpose are well known in the art, and are available in prepackaged kits (e.g., from Sigma-Aldrich.) Once conjugated, the immunogenic peptide-carrier conjugates may then be used to immunize animals to produce monoclonal or polyclonal antibodies. Standard injection regimes, with our without the use of adjuvants (alum, Freunds's, etc.), may be used to produce the desired immune response.

After harvesting, monoclonal or polyclonal antibodies produced using the above polypeptides, which are specific for p110 sEFGR, and which do not cross-react with other ErbB isoforms, may be selected by screening for binding to recombinant p110 sEGFR/sErbB1 and p170 EGFR, as described in the Examples below.

p110 sEGFR polypeptides embodied within the present invention can be "antigenic" and/or "immunogenic". Generally, "antigenic" means that the polypeptide is capable of being used to generate antibodies or indeed is capable of inducing an antibody response in a subject. "Immunogenic" means that the polypeptide is capable of eliciting an immune response in a subject. For example, the polypeptide could not only generate an antibody or anti-idiotypic antibody response but, in addition, non-antibody based immune responses, and also could be used to produce a therapeutic vaccine. In an example, the unique carboxy-terminal region of an p110 sEGFR is a target of the vaccine.

Further embodiments relate to antibodies, which specifically bind the p110 sEGFR isoform, generated using an immunogen derived from the p110 sEGFR isoform, such as from an isoform having SEQ ID NO: 1. In an example, an antibody specific to the p110 sEGFR is generated using the unique carboxy-terminal region (described herein) of the specific p110 sEGFR, such as SSCN QSNDGSVSHQ S or PGNESLKAML FCLFKLSSCN QSNDGSVSHQ S. Such antibodies include, but are not limited to polyclonal, monoclonal, bispecific, humanized or chimeric antibodies, single chain antibodies, Fab fragments and F(ab') fragments, fragments produced by a Fab expression library, anti-idiotypic (anti-Id) antibodies, antibodies, and epitope-binding fragments of any of the above. As used herein, "antibody" refers to immunoglobulin molecules and immunologically active portions of immunoglobulin molecules, i.e., molecules that contain an antigen binding site that specifically binds an antigen. The immunoglobulin molecules can be of any class, e.g., IgG, IgE, IgM, IgD and IgA, or subclass of immunoglobulin molecule. As described above, such antibodies are used for detection and quantification as well as in methods of treating cancer, methods of regulating p110 sEGFR isoforms, and cancer therapeutics.

In the production of antibodies, screening for the desired antibody is accomplished by techniques known in the art, e.g., ELISA (enzyme-linked immunosorbent assay). In one example, to select antibodies which recognize a specific domain of a polypeptide of the invention, generated hybridomas are assayed for reactivity toward a product which binds to a polypeptide fragment of the p110 sEGFR isoform.

Polyclonal antibodies directed towards a p110 sEGFR polypeptide are generated by stimulating their production in a suitable animal host (e.g. a chicken, mouse, rat, guinea pig, rabbit, sheep, goat or monkey) when a polypeptide of embodiments of the present invention is injected into the animal. If necessary, an adjuvant may be administered together with the polypeptide of the invention. The antibodies are then purified by virtue of high affinity binding to the associated polypeptide of the invention.

Monoclonal antibodies (mAbs) directed toward an p110 sEGFR polypeptide may be generated by any technique known to those skilled in the art to provide for the production of antibody molecules by continuous cell lines in culture. Some examples for producing mAbs include the hybridoma technique (Kohler and Milstein, 1975, Nature 256:495-497), the trioma technique, the human B-cell hybridoma technique (Kozbor et al., 1983, Immunology Today 4:72), the EBV-hybridoma technique to produce human monoclonal antibodies (Cole et al., 1985, Monoclonal Antibodies and Cancer Therapy, Alan R. Liss, Inc., pp. 77-96), and germ-free animals (PCT/US90/02545). The hybridoma producing the mAbs of the invention may be cultivated in vitro or in vivo. The mAbs to p110sEGFR include but are not limited to human mAbs and chimeric mAbs (e.g., human-mouse chimeras). A chimeric antibody is a molecule in which different portions are derived from different animal species, such as those having a human immunoglobulin constant region and a variable region derived from a murine mAb. See, for example, U.S. Pat. No. 4,816,567; and U.S. Pat. No. 4,816,397. Humanized antibodies are antibody molecules from non-human species having one or more complementarity determining regions (CDRs) from the non-human species and a framework region from a human immunoglobulin molecule. See, for example, U.S. Pat. No. 5,585,089.

Chimeric and humanized mAbs can be produced by recombinant DNA techniques known in the art, for example and without limitation using methods described in WO 87/02671; EP 184,187; EP 171,496; EP 173,494; WO 86/01533; U.S. Pat. No. 4,816,567; EP 125,023; Better et al., 1988, Science 240:1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Canc. Res. 47:999-1005; Wood et al., 1985, Nature 314:446-449; and Shaw et al., 1988, J. Natl. Cancer Inst. 80:1553-1559; Morrison, 1985, Science 229:1202-1207; Oi et al., 1986, Bio/Techniques 4:214; U.S. Pat. No. 5,225,539; Jones et al., 1986, Nature 321:552-525; Verhoeyan et al. (1988) Science 239:1534; and Beidler et al., 1988, J. Immunol. 141:4053-4060; Neuberger et al., 1984, Nature 312:604-608; Takeda et al., 1985, Nature 314:452-454.

For therapeutics and methods of treating human patients, completely human p110 sEGFR antibodies are desirable. Such antibodies can be generated, for example, using transgenic mice which are incapable of expressing endogenous immunoglobulin heavy and light chain genes, but which can express human heavy and light chain genes. The transgenic mice are immunized by methods known to those skilled in the art with a selected antigen, e.g., all or a portion of an p110 sEGFR specific polypeptide, for example SEQ ID NO: 1, SEQ ID NO: 3-6, or a unique carboxy-terminal sequence, such as the unique carboxy-terminal sequence (amino acids 628-705) or a region thereof such as amino acids SSCN QSNDGSVSHQ S or PGNESLKAML FCLFKLSSCN QSNDGSVSHQ S. Then, mAbs directed against the antigen can be obtained using conventional hybridoma technology where the human immunoglobulin transgenes harbored by the transgenic mice rearrange during B cell differentiation, and subsequently undergo class switching and somatic selection. By using such a technique, therapeutically useful IgG, IgA, IgM, IgD and IgE antibodies can be produced. For references and protocols for producing human antibodies, see, for examples Lonberg and Huszar (1995, Int. Rev. Immunol. 13:65-93); U.S. Pat. No. 5,625,126; U.S. Pat. No. 5,633, 425; U.S. Pat. No. 5,569,825; U.S. Pat. No. 5,661,016; and U.S. Pat. No. 5,545,806.

Furthermore, completely human antibodies which recognize a selected epitope can be produced, for example, by the "guided selection" technique in which a selected non-human mAb, e.g., a mouse antibody, is used to guide the selection of a completely human antibody recognizing the same epitope such as disclosed in Jespers et al. (1994) Biotechnology 12:899-903.

The p110 sEGFR antibodies embodied herein also can be generated using various phage display methods known in the art whereby functional antibody domains are displayed on the surface of phage particles which carry the polynucleotide sequences encoding the functional antibody domains. After phage selection, which is performed for example by using labeled antigen or antigen bound or captured to a solid surface or bead, the antibody coding regions from the phage can be isolated and used to generate whole antibodies, including human antibodies, or any other desired antigen binding fragment, and expressed in any desired host, including mammalian cells, insect cells, plant cells, yeast, and bacteria. Techniques known in the art to produce recombinant Fab, Fab' and F(ab')2 fragments can also be employed.

Single-chain Fvs and antibodies which bind an p110 sEGFR also can be produced by methods known in the art, such as for example those disclosed in U.S. Pat. No. 4,946, 778 and U.S. Pat. No. 5,258,498; Huston et al., Methods in Enzymology 203:46-88 (1991); Shu et al., PNAS 90:7995-7999 (1993); and Skerra et al., Science 240:1038-1040 (1988). In addition, variable domains of camelid heavy chain-only antibodies, called nanobodies, may be produced by methods known in the art (Roovers, R. C., T. Laeremans, et al. (2007) *Cancer Immunol Immunother* 56(3): 303-317; Gainkam, L. O., L. Huang, et al. (2008) *J Nucl Med* 49(5): 788-95; Huang, L., L. O. Gainkam, et al. (2008) *Mol Imaging Biol* 10(3): 167-75; Tijink, B. M., T. Laeremans, et al. (2008) *Mol Cancer Ther* 7(8): 2288-2297). Nanobodies superior properties compared with classical antibodies include that they are small, very stable, easy to produce in large quantities and easy to re-format into multi-valent or multi-specific proteins.

Further, bispecific antibodies which bind to an p110 sEGFR can be made by methods known in the art and are embodied herein. For example, bispecific antibodies comprise a hybrid immunoglobulin heavy chain with a first binding specificity in one arm, and a hybrid immunoglobulin heavy chain-light chain pair with a second binding specificity in the other arm. See, for example WO 94/04690 and Suresh et al., Methods in Enzymology, 1986, 121:210.

Embodiments of the present invention include functionally active fragments, derivatives or analogs of the anti-polypeptide immunoglobulin molecules. "Functionally active" means that the fragment, derivative or analogue is able to elicit anti-anti-idiotype antibodies (i.e., tertiary antibodies) that recognize the same antigen that is recognized by the antibody from which the fragment, derivative or analogue is derived. In an example, the antigenicity of the idiotype of the immunoglobulin molecule is enhanced by deletion of framework and CDR sequences that are carboxy-terminal to the CDR sequence that specifically recognizes the antigen. To determine which CDR sequences bind the antigen, synthetic peptides containing the CDR sequences are used in binding assays with the antigen by any binding assay method known in the art.

Embodiments of the present invention include antibody fragments such as, but not limited to, F(ab')2 fragments and Fab fragments. In examples, antibody fragments which recognize specific epitopes are generated by known techniques to those skilled in the art. F(ab')2 fragments consist of the variable region, the light chain constant region and the CH1 domain of the heavy chain and are generated by pepsin digestion of the antibody molecule. Fab fragments are generated by reducing the disulphide bridges of the F(ab').sub.2 fragments. Further, any other molecule with the same specificity as the antibodies and antibody fragments of embodiments of the present invention are embodied herein.

Embodiments of the present invention also relate to heavy chain and light chain dimers of the antibodies of the invention, or any minimal fragment thereof such as Fvs or single chain antibodies (SCAs). See for example U.S. Pat. No. 4,946,778; Bird, 1988, Science 242:42342; Huston et al., 1988, Proc. Natl. Acad. Sci. USA 85:5879-5883; and Ward et al., 1989, Nature 334:544-54. Single chain antibodies are formed by linking the heavy and light chain fragments of the Fv region via an amino acid bridge, resulting in a single chain polypeptide. Techniques for the assembly of functional Fv fragments in *E. coli* may be used such as the method disclosed in Skerra et al., (1988, Science 242:1038-1041).

Additional embodiments of the present invention provide for fusion polypeptides of the immunoglobulins of embodiments of the invention, or functionally active fragments thereof, for example in which the immunoglobulin is fused via a covalent bond (e.g., a peptide bond), at either the N-terminus or the C-terminus to an amino acid sequence of another polypeptide (or portion thereof, which is at least 10, 20 or 50 amino acids in length) that is not the immunoglobulin. The immunoglobulin, or fragment thereof, may be covalently linked to the other polypeptide at the N-terminus of the constant domain. Such fusion polypeptides may facilitate purification, increase half-life in vivo, and enhance the delivery of an antigen across an epithelial barrier to the immune system.

The immunoglobulin of embodiments of the invention include analogues and derivatives that are modified, such as by the covalent attachment of any type of molecule as long as such covalent attachment does not impair specific binding. For example, without limitation, the derivatives and analogues of the immunoglobulins include those that have been further modified, e.g., by glycosylation, acetylation, pegylation, phosphylation, amidation, derivatization by known protecting/blocking groups, proteolytic cleavage, linkage to a cellular ligand or other protein. In examples, chemical modifications of the analogues and derivatives are carried out by known techniques including, but not limited to, specific chemical cleavage, acetylation, and formylation. In additional examples, the analogues or derivatives contain one or more non-classical amino acids.

In various embodiments, the p110 sEGFR antibodies described herein are used in methods known in the art relating to the localization and activity of the polypeptides of embodiments of the invention. Examples of use include without limitation, imaging or radioimaging these polypeptides, measuring amounts thereof in appropriate biological samples, in diagnostic, prognostic, and theragnostic methods, and for radiotherapy.

The antibody embodiments of the invention can be produced by any method known in the art for the synthesis of antibodies, in particular, by chemical synthesis or by recombinant expression, and may be produced by recombinant expression techniques.

Recombinant expression of antibodies, or fragments, derivatives or analogs thereof, requires construction of a nucleic acid that encodes the antibody. If the nucleotide sequence of the antibody is known, a nucleic acid sequence encoding the antibody may be assembled from chemically synthesized oligonucleotides, as described for example in Kutmeier et al. (1994, BioTechniques 17:242), which, briefly, involves the synthesis of overlapping oligonucleotides containing portions of the sequence encoding antibody, annealing and ligation of those oligonucleotides, and then amplification of the ligated oligonucleotides by PCR.

Alternatively, the nucleic acid encoding the antibody is obtained by cloning the antibody. If a clone containing the nucleic acid encoding the particular antibody is not available, but the sequence of the antibody molecule is known, a nucleic acid encoding the antibody may be obtained from a suitable source (e.g., an antibody cDNA library, or cDNA library generated from any tissue or cells expressing the antibody) by PCR amplification using synthetic primers hybridizable to the 3' and 5' ends of the sequence or by cloning using an oligonucleotide probe specific for the particular gene sequence.

Once a nucleic acid encoding at least the variable domain of the antibody molecule is obtained, it may be introduced into a vector containing the nucleotide sequence encoding the constant region of the antibody molecule. Vectors containing the complete light or heavy chain for co-expression with the nucleic acid to allow the expression of a complete antibody molecule are also available. Then, the nucleic acid encoding the antibody can be used to introduce the nucleotide substitution(s) or deletion(s) necessary to substitute or delete the one or more variable region cysteine residues participating in an intrachain disulphide bond with an amino acid residue that does not contain a sulfhydryl group. Such modifications can be carried out by any method known in the art for the introduction of specific mutations or deletions in a nucleotide sequence, for example, but not limited to, chemical mutagenesis, in vitro site directed mutagenesis, or PCR based methods.

Once a nucleic acid encoding an antibody of the invention has been obtained, the vector for the production of the antibody may be produced by recombinant DNA technology using techniques well known in the art. Such methods can be used to construct expression vectors containing an antibody molecule coding sequence and appropriate transcriptional and translational control signals. These methods include, for example without limitation, in vitro recombinant DNA techniques, synthetic techniques, and in vivo genetic recombination. See, for example, the techniques disclosed in Sambrook et al. (2001, Molecular Cloning, A Laboratory Manual, 3d Ed., Cold Spring Harbor Laboratory, Cold Spring Harbor, N.Y.) and Ausubel et al. (Current Protocols in Molecular Biology, John Wiley & Sons, NY).

A variety of host-expression vector systems can be utilized to express an antibody molecule of embodiments of the invention. Such host-expression systems represent vehicles by which the coding sequences of interest may be produced in large quantity and subsequently purified, but also represent cells which may, when transformed or transfected with the appropriate nucleotide coding sequences, express the antibody molecule of the invention in situ. These include but are not limited to microorganisms such as bacteria (e.g., *E. coli* or *B. subtilis*) transformed with recombinant bacteriophage DNA, plasmid DNA or cosmid DNA expression vectors containing antibody coding sequences; yeast (e.g., *Saccharomyces* or *Pichia*) transformed with recombinant yeast expression vectors containing antibody coding sequences; insect cell systems infected with recombinant virus expression vectors (e.g., baculovirus) containing the antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, HEK 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the antibody molecule being expressed. For example, when a large quantity of such a polypeptide is to be produced for the generation of pharmaceutical compositions comprising an antibody molecule, vectors which direct the expression of high levels of fusion polypeptide products that are readily purified may be desirable. Such vectors include but are not limited to the *E. coli* expression vector pUR278 (Ruther et al., 1983, EMBO J. 2:1791) in which the antibody coding sequence may be ligated individually into the vector in frame with the lac Z coding region so that a fusion polypeptide is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion polypeptides with glutathione S-transferase (GST). In general, such fusion polypeptides are soluble and can easily be purified from lysed cells by adsorption and binding to a matrix of glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter). In mammalian host cells, a number of viral-based expression systems (e.g., an adenovirus expression system or those described above) may be utilized.

As discussed above, a host cell strain may be chosen which modulates the expression of the inserted sequences, or modifies and processes the gene product in a specific way. Such modifications (e.g., glycosylation) and processing (e.g., cleavage) of polypeptide products may be important for the function of the polypeptide.

For long-term, high-yield production of recombinant antibodies, stable expression is preferred. For example, cell lines that stably express an antibody of interest can be produced by transfection of cells with an expression vector comprising the nucleotide sequence of the antibody and the nucleotide sequence of a selectable marker (e.g., neomycin or hygromycin), and selecting for expression of the selectable marker. Such engineered cell lines may be particularly useful for screening and evaluation of agents that interact directly or indirectly with the antibody molecule.

The expression levels of the antibody molecule can be increased by vector amplification.

The host cell may be co-transfected with two expression vectors, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain is preferably placed before the heavy chain to avoid an excess of toxic free heavy chain (see, e.g. Proudfoot, 1986, Nature 322:52; Kohler, 1980, Proc. Natl. Acad. Sci. USA 77:2197). The coding sequences for the heavy and light chains comprise either cDNA or genomic DNA.

Once the recombinant antibody molecule has been expressed, it may be purified by any method known in the art for purification of an antibody molecule, for example without limitation, by chromatography (e.g., ion exchange chromatography, affinity chromatography such as with protein A or specific antigen, and sizing column chromatography), centrifugation, differential solubility, or by any other standard technique for the purification of polypeptides.

In another embodiment, antibodies of the invention or fragments thereof are conjugated to a diagnostic or therapeutic moiety. The antibodies are used for diagnosis or to determine the efficacy of a given treatment regimen. Detection is facilitated by coupling the antibody to a detectable substance. Examples of detectable substances include various enzymes, prosthetic groups, fluorescent materials, luminescent materials, bioluminescent materials, radioactive nuclides, positron emitting metals (for use in positron emission tomography), and non-radioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include .sup.125I, .sup.131I, .sup.111In and .sup.99Tc.

The therapeutic moiety is not to be construed as limited to classical chemical therapeutic agents. In an example, the moiety may be a protein or polypeptide possessing a desired biological activity. Such proteins may include, for example, a toxin such as abrin, ricin A, pseudomonas exotoxin, or diphtheria toxin; a polypeptide such as tumour necrosis factor, .alpha.-interferon, .beta.-interferon, nerve growth factor, platelet derived growth factor, tissue plasminogen activator, a thrombotic agent or an anti-angiogenic agent, e.g., angiostatin or endostatin; or a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor.

Techniques for conjugating such therapeutic moieties to antibodies are well known to those skilled in the art, see for example without limitation, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Alternatively, in another example, an antibody is conjugated to a second antibody to form an antibody heteroconjugate as disclosed for example in U.S. Pat. No. 4,676,980.

An antibody with or without a therapeutic moiety conjugated to it can be used as a therapeutic that is administered alone or in combination with cytotoxic factor(s) and/or cytokine(s).

Screening

Embodiments of the invention include methods and peptides for identifying active agents (e.g., chemical compounds, proteins, or peptides) that bind to an p110 sEGFR polypeptide of embodiments of the invention and/or have a stimulatory or inhibitory effect on the expression or activity of an p110 sEGFR polypeptide of the invention. Examples of active agents, include, but are not limited to, nucleic acids (e.g., DNA and RNA), carbohydrates, lipids, proteins, peptides, peptidomimetics, agonists, antagonists, small molecules and other drugs. Active agents can be obtained using any of the numerous suitable approaches in combinatorial library methods known in the art, including without limitation: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. See, for examples, methods disclosed in Lam, 1997, Anticancer Drug Des. 12:145; U.S. Pat. No. 5,738,996; and U.S. Pat. No. 5,807,683.

Various techniques are known in the art for screening polypeptides that interact with a protein such as p110 sEGFR. Examples of polypeptides include synthetic peptides, small molecular weight peptides (e.g., linear or cyclic peptides) or generated mutant gene products. Techniques for screening large gene libraries often include cloning the gene library into replicable expression vectors, transforming appropriate cells with the resulting library of vectors, and expressing the genes under conditions in which detection of a desired activity, assembly into a trimeric molecule, binding to natural ligands, e.g., a receptor or substrate, facilitates relatively easy isolation of the vector encoding the gene whose product was detected. Examples include without limitation: two hybrid (interaction trap) assays, display libraries in which the candidate peptides are displayed on the surface of a cell, plasmid, or viral particle, and the ability of particular cells or viral particles to bind an appropriate receptor protein via the displayed product is detected in a "panning assay". In an example, such high through-put assays are followed or substituted by secondary screens, such as binding assays, to determine biological activities and differentiate agonists from antagonists.

Immunoassays for sEGFR/sErbB1s and their Diagnostic Uses

An important aspect of the invention is a sandwich immunoassay method for detecting or determining the concentration of soluble and/or full-length human epidermal growth factor receptor in a biological sample obtained from a patient. The method comprises: a) contacting an amount of a first purified antibody that specifically reacts with a first epitope of the extracellular ligand binding domain of sEGFR/sErbB1 with the patient biological sample to be tested, wherein the first purified antibody is modified with a first labeling moiety, b) contacting the sample with an amount of a second purified antibody that specifically reacts with a second epitope of the extracellular ligand binding domain of sEGFR/sErbB1, wherein the second purified antibody is modified with a second labeling moiety, and wherein the second purified antibody does not competitively inhibit the binding of the first purified antibody, and c) determining the presence or amount of the soluble and/or full-length epidermal growth factor receptor complexed with said antibodies by detecting the co-presence of the first and second labels.

In preferred embodiments of the assays of the invention, one antibody is either MAb R.1 or an antibody that binds to the same epitope as MAb R.1. In preferred embodiments, the second antibody is MAb 528, or an antibody that binds to the same epitope as MAb 528. Antibodies may be tested for common epitopes by competitive binding assays according to methods standard in the immunochemical arts. Competitive binding assays using p170 ErbB1, p110 sEGFR/sErbB1, or any other ErbB1 isoform with ligand binding subdomains I-IV may be used as the antigen in a competitive binding assay to determine antibodies for use in the assays of the invention.

It is not intended that the above assays be limited to any particular immunochemistry format. Thus, standard sandwich, soluble sandwich, and competitive binding formats are used in the assays of the invention. In an example, the first labeling moiety is a binding moiety, such as a hapten or biotin. The first labeled antibody is then bound to a streptavidin or avidin coated solid support, such as a microtiter plate well. This serves as a detection mechanism for the first labeling moiety, as the location of the moiety (i.e., bound to the well of the microtiter plate) is then known. After the first antibody is bound to the wells, a patient biological sample may then be introduced into the wells.

In preferred embodiments of this aspect of the invention the patient biological sample is chosen form the group consisting of blood, serum, plasma, urine, saliva, sputum, breast nipple aspirates, tumor lysates, and ascites fluid. Especially preferred samples are serum and plasma. After incubation with the first antibody, the wells are rinsed and then the second labeled antibody is added. In this format, the second labeling moiety is a detectable labeling moiety such as a fluorescent, colorigenic, or chemiluminescent moiety. A preferred moiety for use as the second labeling moiety is acridinium, which is useful in determining especially low concentrations (femtomolar range). After incubation with the second antibody, the wells are again rinsed. Proper reaction components are then added, and the second labeling moiety detected by fluorometry, colorimetry, or luminometry. Thus, the co-presence of the two labels is determined by their location (attached to the well) and their detectable product (fluorescence, light, or colorimetric product).

Embodiments of the invention further provide a diagnostic method for determining the risk or presence of an ovarian carcinoma in a female human patient. The method comprises: a) determining the concentration of soluble EGFR/ErbB1 in a biological sample obtained from a female patient (e.g., by the above immunochemical method), b) comparing the concentration obtained in a) with a normal or baseline level for soluble EGFR/ErbB1 established with samples from female humans without ovarian cancer, and c) associating a decrease in the concentration of sEGFR/sErbB1 in the patient's sample with the presence of an ovarian carcinoma in the patient. A baseline for an assay of the invention may be established from biological samples from healthy patients, as in Example VI. It is desirable to establish baseline concentrations for a range of ages and physiological conditions (such as pre/post menopause) in order to better adjust the baseline value to the patient being tested. As shown in Example VII, the presence of ovarian cancer in female patients is strongly associated with a reduced serum sEGFR/sErbB1 concentration in those patients. Thus, the assays of the invention may be useful for the risk assessment and screening of patients for ovarian cancer using simple phlebotomy samples.

In further embodiments of the assay of the invention, a female patient may be monitored with repeated testing to determine the risk, onset or progression of ovarian cancer. Repeated testing may be done as a yearly screening of a patient to better detect the onset of disease, or at shorter intervals if a patient is at high risk for the disease. Additionally, the female patient may be tested before and after radiation, chemotherapy, or surgical treatment to predict treatment responsiveness or survival, and to monitor treatment responsiveness and/or the regression or progression of ovarian cancer. This follow-up testing may be done at regular intervals, such as monthly or weekly, or at other intervals if indicated by the patient's condition. As shown in example VII, the serum levels of female patients with ovarian cancer may change over the course of treatment, indicating treatment responsiveness and an improved prognosis. Conversely, a decrease in serum sEGFR/sErbB1 levels may be used to catch treatment failure, remission of the disease, or recurrences after cytoreductive surgery before clinical signs and symptoms are observed.

Other embodiments of the present invention relate to methods for quantifying an p110 sEGFR and assessing the risk of developing a pre-neoplastic lesion or cancer, prophylactic selection of a cancer prevention or treatment regimen, screening for cancer, and diagnosing a cancer, such as a carcinoma or a glioma. Such cancers include without limitation esophageal, liver, colon, gastric, thyroid, head and neck, kidney, bladder, pancreatic, lung, skin, breast, ovarian, cervical, endometrial, prostate, brain, intestinal, or testicular. Additional embodiments of the present invention relate to assaying a biological sample for p110 sEGFR to evaluate prognosis, theragnosis, responsiveness to a treatment, progression, recurrence, or metastasis of cancer. One embodiment relates to a method of assaying for an p110 sEGFR and/or diagnosing a cancer in a subject, for example a human or other mammal, which comprises the step of detecting and/or quantifying a concentration of a polypeptide or nucleic acid sequence of the invention in a biological sample obtained from said subject. Examples of biological samples include fluids, such as saliva, blood, serum, plasma, urine, ascites, biopsy tissues, and their derivatives. In an example, antibodies which recognize a polypeptide of the invention are used to detect the amount of the polypeptide in a biological sample such as serum.

In one embodiment, binding of an p110 sEGFR antibody in tissue sections can be used to detect aberrant polypeptide localization or an aberrant concentration of polypeptide. In another embodiment, an antibody to a polypeptide of the invention can be used to assay a subject sample, for example tissue or serum, for the concentration of the polypeptide where an aberrant amount of polypeptide is indicative of a risk of developing a pre-neoplastic lesion or cancer, prognosis, theragnosis, responsiveness to treatment, prophylactic selection of a cancer prevention or treatment regimen, early detection of a cancer, or cancer progression, recurrence, or metastasis. As used herein, an "aberrant amount" means an amount that is increased or decreased compared to the amount in a subject free from cancer or an established reference level.

Examples of suitable immunoassays for detecting or assaying p110 sEGFR include, without limitation, competitive and non-competitive assay systems using techniques such as immunoblots, radioimmunoassays, ELISA (enzyme linked immunosorbent assay), acridinium-linked immunosorbent assays (ALISA), "sandwich" immunoassays, immunohistochemical assays, immunofluorescent detection assays, immunoprecipitation assays, precipitin reactions, gel diffusion precipitin reactions, immunodiffusion assays, agglutination assays, complement-fixation assays, immunoradiometric assays, fluorescent immunoassays and protein A immunoassays. Immunoassays to detect and quantify an p110 sEGFR may be used on formalin-fixed, paraffin-embedded tissue and tumor samples and on frozen-section tissue and tumor samples. In addition, antibodies can be used to quantify selectively an p110 sEGFR polypeptide in other tissues, including for example saliva, blood, serum, plasma, and urine, using enzyme-linked immunosorbent assays, acridinium-linked immunosorbent assays, and radioimmunoassay. Such assays may be combined with the quantitative assessment of other biomarkers on a similar platform (e.g., multiplex assays) to increase the biological or clinical information obtained.

Quantification of the expression of the specific mRNA encoding the polypeptide can be performed using methods such as RNA in situ hybridization (RNA ISH), as well as other complementary RNA methodologies, such as RNAse protection assays. Genetic aberrations in the relative copy number of the sequence can be performed by any genomic DNA detection method, for example FISH.

The p110 sEGFR isoform can be used alone as a biomarker for cancer as described above. For example, a lower concentration of p110 sEGFR in serum is associated with cancer, such as ovarian cancer. In addition, multivariate determinants are useful predictors of clinical classifications such as those described previously (i.e. risk assessment, diagnosis, prognosis, etc.). Multivariate determinants, both physiological and biomarkers, include without limitation age, gender, smoking, menopause status, menstrual cycle phase, parity, gravidity, pregnancy, exogenous hormone usage, p110 sEGFR, gonadotropic hormones (e.g. FSH and LH), sex steroid hormones (e.g. estrogen and testosterone), CA-125, sHER2, etc., depending on the cancer evaluated. For example, mutually adjusting for age, gender, menopause, p110 sEGFR, CA 125, FSH, and LH increases the accuracy in evaluating clinical classifications in epithelial ovarian cancer. In an example, such adjustment is used with statistical models such as multivariate logistic regression, generalized linear, classification and regression tree, artificial neural networks, etc., to calculate a probability value that is evaluated to predict clinical classifications. Embodiments of the present invention also include kits for detecting p110 sEGFR, an apparatus for adjusting and calculating the probability value to predict clinical classifications, and computer readable mediums that are used for adjusting and calculating probability values to predict clinical classifications.

Therapeutics and Methods of Treating

The p110 sEGFR antibodies and nucleotide and polypeptide sequences embodied herein also can be used in methods of treatment and therapeutics for cancers, such as carcinomas and gliomas. Such cancers include without limitation esophageal, liver, colon, gastric, thyroid, head and neck, kidney, bladder, pancreatic, lung, skin, breast, ovarian, cervical, endometrial, prostate, brain, intestinal, or testicular. As such, various embodiments of the present invention include methods and therapeutics to treat cancer, including carcinomas and gliomas, comprising an p110 sEGFR specific antibody, nucleic acid sequence (e.g., DNA and RNA), proteins, and peptides. For example, the methods and therapeutics of the present invention comprise administering the nucleic acid sequence SEQ ID NO: 2, or a complementary sequence thereof, or the amino acid sequences SEQ ID NO: 1 or SEQ ID NO: 3-6. The sequences include for example, without limitation and as more fully described supra, the complete sequence, fragments and variants. Additional embodiments of the present invention include methods to regulate ErbB signaling activity through regulation of p110 sEGFR using the various embodiments herein.

In examples, the therapeutic agent comprises any of the previously described polypeptides, nucleic acid sequences, or variants thereof or previously described instruments, or other agents that can spatially regulate sEGFR expression or function. Examples include without limitation an p110 sEGFR polypeptide, or a functional fragment, variant or analog thereof having an p110 sEGFR activity; a polypeptide agonist or antagonist of p110 sEGFR that increases or decreases respectively the activity of an p110 sEGFR or the binding of an p110 sEGFR to a binding partner; a small molecule that increases or decreases expression of an p110 sEGFR, for example by binding to the promoter region of the sEGFR gene; an antibody, for example an antibody that binds to and stabilizes or assists the binding of p110 sEGFR to an p110 sEGFR binding partner or an antibody that inhibits binding to and destabilizes the binding of p110 sEGFR to an p110 sEGFR binding partner; or a nucleotide sequence encoding an p110 sEGFR polypeptide or functional fragment or analog thereof. The agent and instruments described herein also may comprise any compositions or methods in molecular medicine or therapeutic transfer of genetic material known to those skilled in the art such as those previously described above to achieve a therapeutic effect.

In an embodiment, the amount of p110 sEGFR protein is increased by elevated transcriptional expression of the endogenous EGFR gene and translation of the p110 sEGFR isoform from its alternate mRNA or by increasing p110 sEGFR mRNA stability. In another embodiment, transcription of the EGFR gene is increased for example by altering its regulatory sequence such as by the addition of a positive regulatory element (such as an enhancer or a DNA-binding site for a transcriptional activator); the deletion of a negative regulatory element (such as a DNA-binding site for a transcriptional repressor); and/or replacement of the endogenous regulatory sequence, or elements therein, with that of another gene, thereby allowing the coding region of the ErbB3 gene to be transcribed more efficiently. In other examples, the amount of p110 sEGFR protein is regulated post-transcriptionally by microRNAS or other post-transcriptional regulatory elements.

In an embodiment, the agent is a vector that includes a nucleic acid sequence encoding p110 sEGFR, preferably human p110 sEGFR, for example SEQ ID NO: 1. The vector can be any vector suitable for transfer of genetic material such as those listed previously or that are known in the art.

The therapeutic composition can be administered by any method known in the art, for example by direct administration, e.g., injection, intravenous or intramuscular, to a subject, for example a human. In another example, the composition is delivered directly to an affected tissue. The composition can be coupled to a second agent, for example a delivery agent (e.g., an agent that protects the agent from degradation) or a targeting agent (e.g., for targeting to the cancer or affected tissue or targeting to the inside of a cell). Targeting may occur by means of, for example, the gene delivery vehicle, cell-type or tissue-type expression due to the transcriptional regulatory sequences controlling expression of the receptor gene, or a combination thereof.

Such compositions may include a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances are known. Except insofar as any conventional media or agent is incompatible with the active compound, such media can be used in the compositions of the invention. Supplementary active compounds can also be incorporated into the compositions.

The composition may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by admixing the active ingredient with the carrier(s) or excipient(s) under sterile conditions.

Embodiments of the invention further provide quantitative diagnostic and pharmaceutical packs and kits comprising one or more containers filled with one or more of the ingredients of the aforementioned compositions of embodiments of the invention. For example, the kit may comprise an antibody, nucleotide sequence, or polypeptide specific to p110 sEGFR. Further, the kit may contain other ingredients necessary or useful in combination with active ingredients or components embodied herein. Associated with such container(s) can be a notice in the form prescribed by a governmental agency regulating the manufacture, use or sale of pharmaceuticals or biological products, reflecting approval by the agency of the manufacture, or use or sale of the product for human administration. Informational material can be included which is descriptive, instructional, marketing or other material that relates to the methods described herein and/or the use of the agent for the methods described herein. The kit may contain separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In various embodiments, the kit includes a plurality of individual containers, each containing one or more unit forms of the composition. The containers of the kits can be air tight and/or waterproof.

The present invention has been described with reference to specific details of particular embodiments thereof. It is not intended that such details be regarded as limitations upon the scope of the invention except insofar as and to the extent that they are included in the accompanying claims.

The following examples are offered to further illustrate the various aspects of the present invention, and are not meant to limit the invention in any fashion. Based on these examples, and the preceding discussion of the embodiments and uses of the invention, several variations of the invention will become apparent to one of ordinary skill in the art. Such self-evident alterations are also considered to be within the scope of the present invention.

Example I

Isolation and Characterization of Human EGFR/ERBB1 cDNAs Encoding Soluble EGFRs

Figure 1:
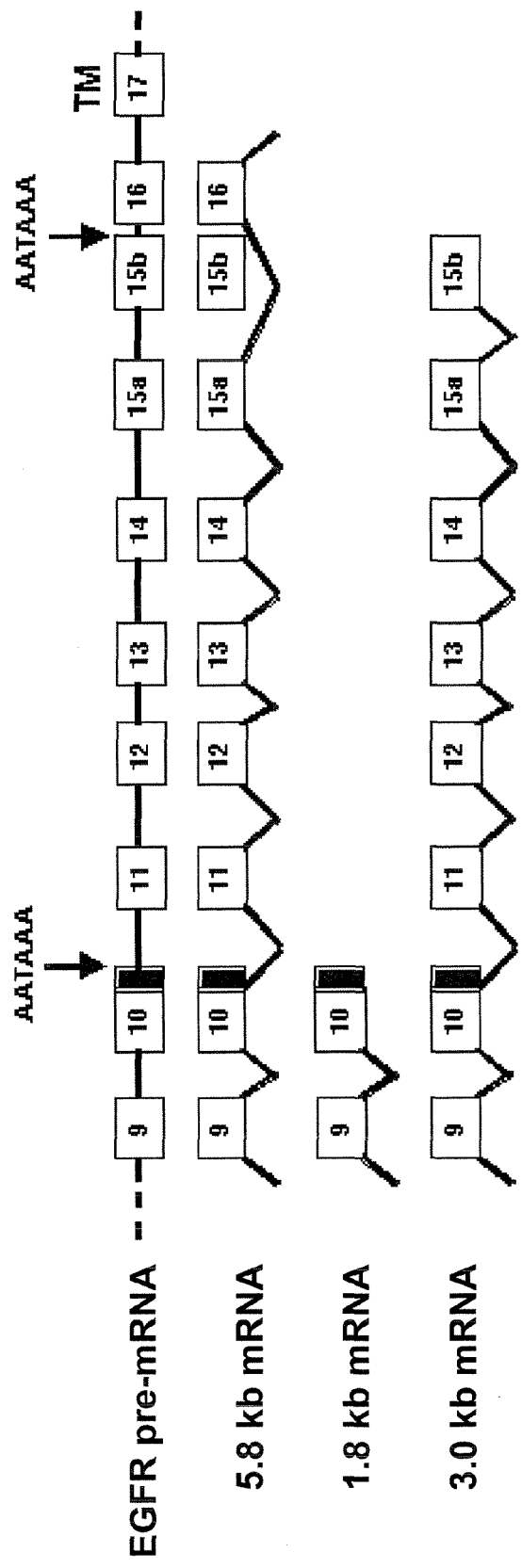
FIG. 1 is a schematic representation of full-length EGFR (i.e. 5.8 kb mRNA), p60 sEGFR (1.8 kb mRNA), and normal p110 sEGFR (3.0 kb mRNA) transcripts with open boxes representing exons and lines representing introns.
Figure 2:
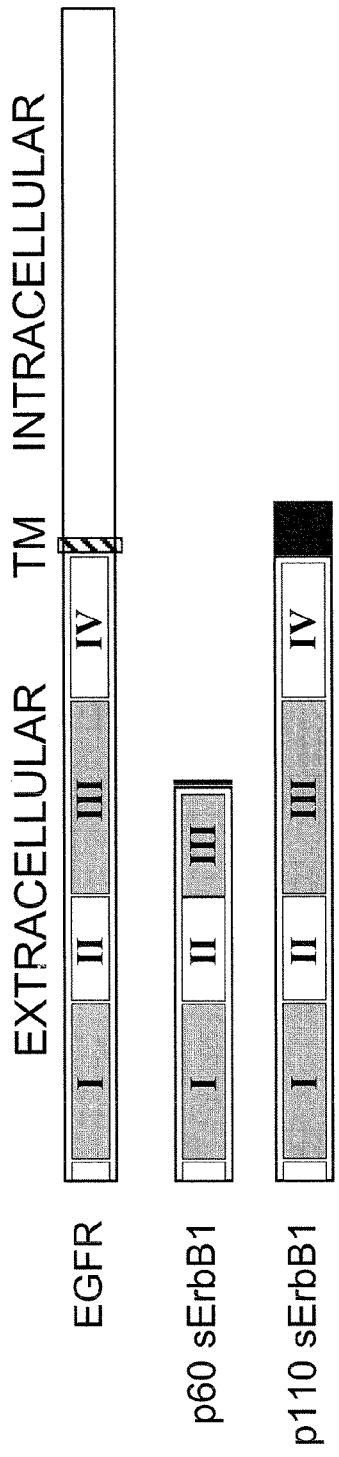
FIG. 2 is a structural comparison of p60 and p110 soluble isoforms of EGFR relative to the full-length EGFR.

To isolate human EGFR clones that lack sequences encoding the cytoplasmic domain, but have the extracellular domain, differential hybridization was employed to screen an oligo-dT primed human placental cDNA library (Clontech, cat, #H1144x). The library was screened for clones that were positive for a ligand binding domain (LBD) specific probe (positions 174-2105), but negative for a kinase domain (KD) probe (see FIG. 2 for full length EGFR versus p110 sEGFR comparison).

The ligand binding domain probe was synthesized by the PCR using pXER as a template (Chen et al., Nature, 32, 820 (1987)). The forward primer was: SEQ ID NO: 7, corresponding to nucleotide positions 174-193. The reverse primer had the sequence SEQ ID NO:8, representing base pairs 2086-2105. Nucleotide numbering is according to Ullrich et al., supra, unless stated otherwise. Amplification was performed for 35 cycles (94° C. for 1 minute; 65° C. for 1 minute; 72° C. for 3 minutes) with a final extension at 72° C. for 10 minutes. The PCR product was then excised from a low melting point agarose gel. A 768 by EcoR1 fragment from pXER was gel purified and used as the intracellular kinase domain (KD) probe. The LBD and KD probes were radiolabeled with [α-$^{32}$P]dCTP using a random primer DNA labeling kit (Gibco BRL) according to the manufacturer's instructions. The hybridizations were performed in a solution containing 6×SSC, 5×Denhard's, 7.5% dextran sulfate, 0.5% N-lauryl sarcosine, and 100 µg/ml salmon sperm DNA at 65° C. Filters were washed in 0.1×SSC and 0.1% N-lauryl sarcosine at 65° C. and then were exposed to x-ray film for 24 to 72 hours at −80° C. with an intensifying screen.

Several clones hybridizing exclusively to the LBD probe were purified. Plasmid DNA, which contained inserts of interest, was released from the pλDR2 vector by site-specific recombination using the CRE-lox system (Murphy et al., supra). Inserts were sequenced on both strands using the Taq DyeDeoxy cycle sequencing kit and the Applied Biosystems model 373A automated DNA sequencer.

To determine whether the transcript encoding p110 sEGFR/sErbB1 is expressed in human 25 placenta, RNA from a human placenta cell line (ATCC, CRL 1584) was isolated by a guanidine isothiocyanate procedure. Isolated RNA was treated with RNase free DNase and extracted twice with 1:1 phenol:chloroform. RNA (1 µg) was heated to 90° C. for 5 minutes, then the RNA was reverse transcribed in a 20 µl, 1 reaction containing 1× Avian Myeloblastosis Virus (AMV) reaction buffer, 1 mM each dNTP, 10 mM dithiothreitol (DTT), 20 U RNAsin, 10 U AMV reverse transcriptase, and 0.1 µg oligo-dT at 24° C. for 10 minutes, 42° C. for 50 minutes, 99° C. for 5 minutes and then 4° C. for 5 minutes. The first strand cDNAs were then amplified by adding Taq polymerase to the reverse transcription reaction along with pEXI5F (SEQ ID NO:9) and pEX15R (SEQ ID NO:13) in a final volume of 100 µl under the amplification conditions described hereinabove. The amplified products were analyzed by 5% PAGE. The results show that the 3.0 kb transcript is expressed in the human placenta cell line.

Thus, the isolated clone represents a 3.0 kb alternative transcript of EGFR. To map the 3.0 kb transcript, the following primers were employed: P1981 (EX15F; SEQ ID NO:9), P267F (EX15bF; SEQ ID NO:10), P615F (EX15bF; SEQ ID NO:11), P297R (EX 15bR; SEQ ID NO:12) and P732R (EX15bR; SEQ ID NO:13). The 3.0 kb transcript arises from an alternative splicing event from exon 15 to a novel exon located within intron 15 of the EGFR gene. This novel exon contains 2 polyadenylation sites. None of the downstream EGFR exons are included in this transcript. This transcript differs from the 2.8 kb transcript unique to A431 cells as the A431 transcript contains EGFR exons 1 to 16 and then splices to an unrelated sequence derived from a translocation. The 3.0 kb transcript encodes a polypeptide of 681 amino acids (less the 24 amino acid signal peptide) (SEQ ID NO:1) containing 78 unique carboxy-terminal amino acids Pro 628-His 705 of SEQ ID NO: 1.

Other variant unique EGFR-related sequences that have been detected by either cDNA cloning or by PCR include truncation at amino acid Phe 641 (SEQ ID NO:3), Gln to Arg at amino acid 657 (SEQ ID NO:4), Pro to Leu at amino acid 661 (SEQ ID NO:5), and Ser to Phe at amino acid 703 (SEQ ID NO:6).

Therefore, soluble isoforms of human EGFR, as well as amino acid variants of these sEGFR/sErbB1s, are expressed in placental tissue.

Example II

Soluble Human EGFR/ERBB1 Gene Product

The amino acid sequence deduced from the 3.0 kb EGFR/ERBB1 cDNA (SEQ ID NO:1) predicted a 705 amino acid polypeptide with a molecular mass of 77 kDa. The first 24 amino acids code for a signal peptide; following cleavage by signal peptidases, the predicted molecular weight of this polypeptide is 75 kDa. The sequence encodes subdomains I, II, III and a portion of subdomain IV of the extracellular ligand binding domain of the EGFR plus an additional 78 unique carboxy-terminal amino acids. A quail fibroblast cell line, QT6, was transiently transfected with the plasmid pDR2241, which contains the 3.0 kb EGFR/ERBB1 transcript and synthesizes a 110 kDa glycosylated polypeptide (p110 sErbB1). Cells were transfected with 15 µg of pDR2241 by the calcium phosphate precipitation technique as described previously (Ausubel et al., Current Protocols in Molecular Biology, John Wiley & Sons, NY (1994)).

Transfected cells from two 10 cm plates were pooled and replated in 6 well plates approximately 48 hours post-transfection. The following day, cells were rinsed once in phosphate buffered saline (PBS) and labeled in methionine free DMEM supplemented with 5% dialyzed FCS and 150 µCi/ml of [$^{35}$S] methionine (Promix, Amersham) at 37° C. for 12 hours. Conditioned medium from labeled cells was collected and centrifuged briefly to remove loose cells and debris and phenylmethylsulfonyl fluoride (PMSF) and aprotinin were added to a final concentration of 1 mM and 50 µg/ml. Cell monolayers were lysed and immunoprecipitated with the addition of 1 to 5 µg of monoclonal antibody as described previously (Maihle et al., Mol. Cell. Biol., 8, 4868 (1988)). Samples were resuspended in 2× Laemmli sample buffer (125 mM Tris-HCl, pH 6.8, 4% SDS, 20% glycerol, 10% 2-mercaptoethanol, 2 mM EDTA, 0.04% bromphenol blue), boiled for 5 minutes and separated by 10% SDS-PAGE. Gels were stained with Coomassie blue, treated with EnHance (Dupont) and dried before an overnight exposure to x-ray film.

Immunoprecipitation of mock transfected cells failed to reveal a specific EGFR related polypeptide in either cell lysates or in conditioned media, while a 115 kDa soluble EGFR was immunoprecipitated from the media of control A431 cells. Immunoprecipitation of cell lysates from transfected cells revealed a heterogeneous 110 kDa species that was specifically recognized by the EGFR specific monoclonal antibody, R.1 (Amersham, RPN 513) (Waterfield et al., J. Cell. Biochem., 20, 149 (1989)). Thus, expression of the nucleic acids of the invention encoding soluble isoforms of the human EGFR results in a glycosylated sEGFR/sErbB1 protein when transgenically expressed in eukaryotic cells.

Example III

Growth Inhibitory Potential of Soluble ErbB1 Receptors on Ovarian Carcinoma Cell Growth In Vitro To examine the affect of p110 sEGFR/sErbB1 on EGFR-regulated cell growth, stable CHO cell lines expressing p110 and/or EGFR have been established and clonally isolated. Co-expression of p110 sErbB1 in cells expressing p170 EGFR results in the rapid and unexpected induction of cell rounding (24 hr) and programmed cell death (48 hr). See FIG. 5. The mechanism of cell death has been verified to be apoptotic based on nuclear morphology and Hoechst staining. Interestingly, cell death does not occur in CHO cells treated similarly but expressing a truncated EGFR mutant that has lost most of its extracellular domain (i.e., the type III variant, originally cloned from a human glioma). These results were initially discovered using transient transfection analyses, but since that time inducible expression of p110 in CHO cells has been established using an ecdysone promoter system (Invitrogen), and have produced identical results using this inducible system. These results suggest that p110 sEGFR/sErbB1 may be able to interfere with EGFR-dependent cell substrate attachments, and hence cell survival, and that these attachments are dependent on the extracellular domain of the EGFR.

To determine the function of the human 3.0 kb alternative transcript which encodes p110 sEGFR/sErbB1, a quantitative ribonuclease protection assay was used to determine its relative abundance in RNA from 17 adult tissues (brain, breast, colon, heart, kidney, liver, lung, pancreas, placenta, prostate, skeletal muscle, small intestine, spleen, stomach, testis, thymus, and uterus) and 4 fetal tissues (brain, kidney, liver, and lung), as well as in numerous carcinoma-derived cell lines, either with or without EGFR gene amplification. The riboprobe consisted of 313 nt (1754-2066 in X00588) shared by both the full-length and the 3.0 kb transcripts, plus 134 by of exon 15B which was specific for the 3.0 kb mRNA. Transcripts containing exon 15B would result in a protected fragment of 447 nts, whereas those containing exon 15 spliced to exon 16 would result in a protected fragment of 313 nts. The full-length transcripts were observed in all of the samples examined, while the 3.0 kb transcript was detected only in human placenta, and in the carcinoma cell lines which also contained amplification of the EGFR gene. The relative ratio of full-length to 3.0 kb transcripts was quantified using a phosphoimager. The relative amount of the full-length mRNA was ~200-fold greater than the level of the 3.0 kb transcript in both human placenta and in the MDA-MB-468 breast carcinoma cell line, which contains ~15-fold amplification of the EGFR gene (Filmus et al., 1985). However, in the A431 carcinoma cell line containing ~30-fold amplification of the EGFR gene, the full-length transcript was only present in 100-fold excess compared to the 3.0 kb mRNA. The 3.0 kb transcript was not detected in the absence of EGFR gene amplification in other carcinoma-derived cell lines.

Normal cells are expected to tolerate co-expression of p110 sEGFR/sErbB1 with sEGFR/sEGFR because these proteins may route to distinct membranes (i.e., apical vs. basolateral), whereas co-localization of these receptors may result in apoptosis. Accordingly, the loss of cell polarity/membrane organization, which is characteristic of high-grade carcinomas, may result in selection against p110 sEGFR/sErbB1 expression in ovarian tumors.

Once the integrity of the soluble EGF receptor, produced as described in Example II, has been established (i.e., by mobility as a discrete band of the appropriate molecular weight on an SDS gel) serial dilutions of these preparations are added to the culture media (MEM-α reduced FCS, +/−recombinant EGF/TGF-α (Collaborative Research)) of selected (c-erbB expressors vs. nonexpressors) ovarian carcinoma cells to assay their effect on cell growth. Changes in cell growth rates are determined by monitoring $^3$H-thymidine incorporation, and by using an MTT cell growth assay.

Example IV

Preparation of Antibodies

By utilizing polypeptide sequences derived from the unique 78 amino acid carboxy-terminus of SEQ ID NO: 1, 3, 4, 5, or 6, specific monoclonal antibodies may be produced to SEQ ID NO: 1, 3, 4, 5, or 6 (note: as the unique carboxy terminus of SEQ ID NO: 3 is a portion of SEQ ID NO: 1's carboxy terminus, antibodies raised using some or all of the first 14 amino acids of the 78 amino acid carboxy terminal sequence of SEQ ID NO: 1 may react with SEQ ID NO: 3). Monoclonal antibodies may be prepared by analogy to the methods described below for the preparation of subdomain I, III, and IV specific antibodies.

To prepare monoclonal antibodies (MAbs) specific for epitopes present in domains I, III or IV of full-length human EGFR, synthetic peptides were prepared. The peptides were predicted to have a high hydrophilicity, surface probability, and antigenicity. The peptides correspond to amino acids 77 to 93 of subdomain I (SEQ ID NO:14), 290-311 of subdomain III (SEQ ID NO:15), 352-369 of subdomain III (SEQ ID NO:16), and 556-567 of subdomain IV (SEQ ID NO:17) of the complete EGF/ErbB1 receptor, which lacks the signal peptide. Peptide immunogens were made by coupling the peptides to keyhole limpet hemocyanin and bovine serum albumin. The maleimide coupling chemistry required the addition of cysteines to the carboxy-terminus of the 77 to 93 and 352-369 peptides, while the native cysteines of the 290-311 and 556-567 peptides were used for coupling.

Although every immunized mouse elicited an immunological response toward its cognate peptide, as determined by ELISA, only mice injected with peptides having SEQ ID NO:15, SEQ ID NO:16 or SEQ ID NO:17 produced antibodies capable of recognizing the 170 kDa ErbB1 receptor (p170) from A431 whole cell lysates by Western blot. Hybridomas from mice injected with peptides having amino acids 290 to 311 (clone 10B7), 352-369 (clones 15E11 and 17H3), and 556-567 (clone 2D2) of the mature EGFR were generated. All of these clones produced monoclonal antibodies that recognized p 170 ErbB1 in Western blots, and that bound to A431 cells as detected by immunofluorescence microscopy. Two MAbs (15E11 and 2D2) were also compatible with immunohistochemical methods, whereby cells or tissues are embedded in paraffin, sectioned, treated with steam and citrate to retrieve masked antigens, immunolabeled, and processed to visualize antigen with diaminobenzidine.

Three MAbs (10B7, 15E11, and 2D2) were able to immunoprecipitate p170 ErbB1 from whole cell lysates of A431 cells. One of these MAbs (15E11) immunoprecipitated a 60 kDa soluble isoform of human sEGFR/sErbB1 (p60) from whole cell lysates and culture media of transfected QT6 quail fibroblasts (QT6/pDR161). MAb 15E11 also detected p60 sEGFR/sErbB1 in QT6/pDR161 culture media by ALISA (acridinium-linked immunosorbent assay). MAb 15E11 was covalently coupled to Protein G and this resin was employed to purify (80% homogeneity) p60 sErbB1 from QT6/pDR161 culture media by immunoaffinity chromatography. This MAb reacted in the same manner to p110 ErbB1.

Hybridoma clones 10B7, 15E11, 17H3 and 2D2 have been deposited with the American Type Culture Collection, in accordance with the requirements of the Budapest Treaty, and granted Accession Nos. HB-12204, HB-12205, HB-12206, and HB-12207, respectively. Polyclonal and monoclonal antibodies have been generated for p110 sEGFR using a 15 amino acid sequence, SSCN QSNDGSVSHQ S (corresponding to amino acids 644-658), and a 31 amino acid sequence in the unique carboxy terminal region of p110 sEGFR, PGNESLKAML FCLFKLSSCN QSNDGSVSHQ S (corresponding to amino acids 628-658). Monoclonal antibodies to each peptide were generated using Balb-c mice injected with the peptides similar to the method above. Several hybridoma clones were generated. These antibodies have been shown to bind to p110 sEGFR using ELISA assays, as well as by immunoblot analysis, which demonstrate detection of a single band with an apparent molecular weight of 110 kDa, and also by indirect immunohistochemical analysis of transfected CHO cells, which detect both cell surface and membrane compartment cytoplasmic staining of p110 sEGFR only in cells transfected with the 3.0 kb sEGFR cDNA, and not in parental CHO cells.

Example V

ALISA for Detection of the sEGFR/sErbB1 Isoform(s) in Human Sera and Cell Culture A sensitive acridinium-linked immunosorbent assay (AL-ISA) quantifies sErbBl/sEGFR and EGFR/ErbB1 molecules in patient body fluids and tissues. This ALISA was used to quantify serum sEGFR/sErbB1 levels in healthy men and women, as further described in Example VI, and in patients with ovarian cancer. The experimental results of Baron et al., J. Immunol. Methods, 219, 23 (1998) are incorporated by reference. The ALISA was developed using the following:

Antibody Reagents and Analytes

Sheep anti-EGFR/ErbB1 antiserum (cat. #06-129) was obtained from Upstate Biotechnology (Lake Placid, N.Y.). Antiserum #06-129 was prepared against a recombinant fusion protein that embodies exons 15-18. Because exon 17 encodes the transmembrane domain, this protein embodies extracellular, transmembrane, and cytoplasmic amino acid sequences. Mouse MAbs specific for EGFR/ErbB1 ECD were obtained from various commercial sources: MAb R.1 (Amersham Life Science, Arlington Heights, Ill.; Oncogene Research Products, Cambridge, Mass.; Santa Cruz Biotechnology, Santa Cruz, Calif.), MAb C11 (Cambridge Research Biochemicals, Valley Stream, N.Y.), MAb 528 (Oncogene Research Products; Santa Cruz Biotechnology), MAb 225 (Oncogene Research Products), MAb LA1 (Upstate Biotechnology), MAb LA22 (Upstate Biotechnology), MAb 111.6 (NeoMarkers, Freemont, Calif.), MAb 199.12 (NeoMarkers). MAbs 10B7, 15E11, 17H3, and 2D2 disclosed above are specific toward peptide epitopes of ErbB1 ECD. MAb 20H5 (Sanders and Salisbury, 1994), which is specific for the cytoskeletal protein centrin, was used as a control antibody.

Purified p170 EGFR/ErbBl, which is used as the standard analyte, was purchased from Sigma (St. Louis, Mo.). The protein concentration of p170 EGFR/ErbB1 given by Sigma was confirmed by quantitative amino acid analysis. Briefly, p170 EGFR/ErbBl was transferred to 6×50 mm borosilicate tubes, dried, placed in a larger vial with 200 µl of 6 N HCl plus 1% phenol for hydrolysis under vacuum for 24 hours. The hydrolyzed amino acids were injected onto a Beckman 6300 Amino Acid Analyzer using sodium buffers (Beckman Instruments, Fullerton, Calif.). Chromatographic data were collected and analyzed with Beckman System Gold software, using norleucine as an internal amino acid standard. The concentration of p170 EGFR/ErbB1 was determined by total recovery of alanine, phenylalanine, and proline in comparison to norleucine. The control analyte, trpEcentrin, was purified and concentration determined by Bicinchoninic Acid Assay (BCA) (Pierce Chemical, Rockford, Ill.).

Generation of QT6/psErbB1ECD589

A cDNA fragment encoding 589 amino acids of the human EGF receptor's ECD was subcloned from pXER (Chen et al., 1989; a.k.a. pXEGFR, Opresko et al., 1995) into pcDNA3 (Invitrogen, Carlsbad, Calif.). pXER was digested with Nae I; an approximately 3.5 kb cDNA fragment was resolved by agarose gel electrophoresis and gel purified using GENECLEAN™ (BIO 101, La Jolla, Calif.). The 5'-Nae I restriction enzyme site was located within the pXER vector, whereas the 3'-Nae I site was positioned just before nucleotide 2026 of the EGFR/ERBB1/HER1 cDNA; the nucleotide numbering system is that of Ullrich et al. (1984), Xba I linkers (Boehringer Mannheim, Indianapolis, Ind.) were phosphorylated with T4 polynucleotide kinase and ligated to the blunt-ended approximately 3.5 kb Nae I restriction fragment with T4 DNA ligase. The linker-ligated restriction fragment was subsequently digested with Xba I to yield two DNA fragments of approximately 1.5 kb and approximately 2.0 kb. The larger approximately 2.0 kb EGFR/ERBB1/HER1 cDNA fragment encoding the ECD of EGFR/ErbB1 was purified as described above and ligated to Xba I digested, calf intestine phosphatase treated pcDNA3. E. coli DH5-α were transformed with pcDNA3 constructs containing the approximately 2.0 kb EGFR/ERBB1/HER1 cDNA according to the method of Hanahan (Maniatis et al., 1982) and grown on Luria-Bertani agar plates containing 100 µg/ml ampicillin as a selectable marker. Plasmid DNA was isolated by the boiling method from transformed bacterial colonies (Ausubel et al., 1989) and digested with BamH I to determine the orientation of the approximately 2 kb EGFR/ERBB 1/HER1 insert in pcDNA3. Plasmids containing the approximately 2 kb EGFR/ERBB1 fragment in the sense orientation yield a BamH I restriction fragment of 1348 bp, whereas clones containing the approximately 2 kb EGFR/ERBB1/HER1 fragment in the antisense orientation yield a 678 by restriction fragment. A transformed clone of E. coli DH5-α containing the approximately 2.0 kb EGFR/ERBB1/HER1 fragment in the sense orientation was identified and plasmid DNA, called psErbB1ECD589, was prepared using the QIAGEN plasmid purification kit (QIAGEN, Chatsworth, Calif.) for transfection experiments. The quail fibroblast cell line, QT6, was subsequently transfected with psErbB1ECD589 by calcium phosphate precipitation (Wigler et al., 1979) and stable, geneticin (G418) resistant cells were isolated and cloned by limiting dilution. A clonal cell line, QT6/psErbB1ECD589, expressing p100 sErbB1 was identified by immunoprecipitation of $^{35}$S-labeled cell lysates with MAb C11 using methods described previously (Maihle et al., 1988).

Cell Culture

All tissue culture cells were grown in $NaHCO_3$, buffered media at 37° C. in 5% $CO_2$ and air. All tissue culture reagents were purchased from Gibco BRL Life Technologies (Grand Island, N.Y.). A431, MDA-MB-453, and SK-BR-3 cells (ATCC) were maintained in Dulbecco's Modified Eagle Medium (DMEM) supplemented with 20 mM Hepes, pH 7.3, 10% fetal bovine serum (FBS), 1 mM sodium pyruvate, and 2 mM L-glutamine. QT6 quail fibroblasts (Moscovici et al., 1977; ATCC) and QT6 cells transfected with the plasmid vectors pDR161 or psErbB1ECD589, QT6/pDR161 (Reiter and Maihle, 1996) or QT6/psErbB1ECD589, respectively, were grown in DMEM supplemented with 20 mM Hepes, pH 7.3, 4% heat inactivated FBS, 1% chicken serum, 1 mM sodium pyruvate, and 2 mM L-glutamine.

Generation of Whole Cell Lysates for ALISA

Tissue culture cells at 80% to 90% confluence were rinsed once with phosphate buffered saline (PBS; 10 mM $KH_2PO_4$/$K_2HPO_4$, 150 mM NaCl, pH 7.2), scraped from the PBS loaded petri dish with a cell lifter (Costar, Cambridge, Mass.), and harvested by centrifugation at approximately 1000×g for 5 minutes. The cell pellet was resuspended and lysed by adding a 1:10 (w/v) ratio of membrane protein immunoprecipitation lysis buffer containing protease inhibitors (10 mM Trizma®, pH 7.4, 150 mM NaCl, 1 mM EDTA, 1% Nonidet P-40, 150 µg/ml phenylmethyl sulfonyl fluoride, 2 µg/ml aprotinin, 0.5 µg/ml leupeptin, 1 µg/ml pepstatin A). The cell lysate was vigorously vortexed for 30 seconds and sonicated (three 10 second bursts at half power with 60 second cooling periods) with a sonicator (model W-225R; Heat Systems-Ultrasonics, Farmingdale, N.Y.) to break DNA molecules. Enough 5.0 M NaCl was added to the cell lysate to bring the final NaCl concentration to 500 mM. Cellular debris was pelleted by centrifugation at 10,000×g for 10 minutes. The resulting supernatant was exchanged into Trizma buffered saline (TBS; 10 mM Trizma, pH 7.4, 150 mM NaCl) containing 0.02% $NaN_3$ by passage through a Sephadex G-25 fast desalting gel filtration column using a Fast Performance Liquid Chromatography system (FPLC; Pharmacia Biotech, Piscataway, N.J.), and concentrated by ultrafiltration with a Centricon centrifugal concentrator (Amicon, Beverly, Mass.). The protein concentration of the final whole cell lysate was determined by BCA (Pierce Chemical).

Acridinium Labeling Procedure

A 1 mg/ml stock solution of succinimidyl-activated acridinium ester [4-(2-succinimidyl-xycarbonylethyl)phenyl-10-acridinium-9-carboxylate sulfonate; ASSAY Designs, Ann Arbor, Mich.) in dry dimethyl formamide was stored in 5 µg aliquots at −70° C. MAb IgG was exchanged from carrier solution into labeling buffer (0.2 M sodium phosphate buffer ($NaH_2PO_4/Na_2HPO_4$) pH 8.0) with a Sephadex G-25 fast desalting gel filtration column by FPLC and concentrated by ultrafiltration to 200 µl, and approximately 1.0 mg/ml total protein. MAb IgG was labeled at room temperature with a 1:80 molar ratio of IgG to succinimidyl-activated acridinium ester for 15 minutes in the dark. The coupling reaction was stopped by adding 100 d of quenching buffer (labeling buffer with 10 mg/ml lysine monohydrochloride) and incubating for an additional 5 minutes. Unbound acridinium ester was removed with a Sephadex® G-25 fast desalting gel filtration column by FPLC and simultaneously exchanged into a solution containing 0.2 M sodium phosphate buffer, pH 7.3, and 0.02% $NaN_3$. Following buffer exchange by FPLC, the acridinium-labeled MAb IgG was concentrated by ultrafiltration to a volume of 100 µl, 1; 1.0 ml of storage buffer (0.2 M sodium phosphate buffer, pH 7.3, 0.1% bovine serum albumin, 0.02% $NaN_3$) was added and the volume was reduced again to 100 µl. The Relative Light Units (RLU)/µl were determined and the final acridinium-labeled MAb IgG was stored at −70° C.

ErbB1 ECD-Specific Acridinium-Linked Immunosorbent Assay

White XENOBIND® 96 well microtiter plates (Xenopore, Saddle Brook, N.J.) were coated overnight at 4° C. with 25 µg/well of an affinity-purified goat anti-mouse $IgG_{2b}$ specific polyclonal antibody in carbonate buffer (90 mM $NaHCO_3$, 10 mM $N_a2CO_3$, pH 9.4, 0.02% $NaN_3$); the antigen is attached covalently to the plate under these conditions. All incubations were performed on a rocker platform. The plates were washed three times with high salt Tween-20® wash buffer (HST-20WB; 0.05% polyoxyethylene sorbitan monolaurate (Tween-20®, 20 mM Trizma®, pH 7.4, 500 mM NaCl, 0.02% $NaN_3$) blocked with ALISA blocking buffer (ALBB; 2.0% bovine serum albumin (BSA), 10 mM Trizma pH 7.4, 150 mM NaCl, 0.02% $NaN_3$) for 1 hour at room temperature, washed with HST-20WB, incubated with 0.05 µg/well anti-EGFR/ErbB1 ECD-specific MAb R.1 diluted in ALBB for 2 hours at 37° C., washed three times with HST-20WB, incubated with analyte or unknown sample for 2 h at 37° C., washed three times with HST-20WB, incubated with acridinium-labeled anti-EGFR/ErbB1 ECD-specific MAb 528 (500,000 counts/well) for 1 hour at 37° C., washed three times with HST-20WB, and read with a luminometer (model LB 96P; EG&G Berthold Analytical Instruments, Nashua, N.H.). In order to maintain an even temperature across the microtiter plate, all 37° C. incubations were performed in a forced-air environmental shaker (model 3528; Lab-Line Instruments, Melrose Park, Ill.) that was modified to hold microtiter plates. Acridinium decomposition was initiated by sequentially adding a solution containing 0.441% nitric acid and 0.495% $H_2O_2$ followed by a solution containing 0.25 M NaOH and 0.1875% cetyltrimethylammonium chloride. This treatment drives the acridinium ester to form an unstable dioxetanone intermediate, which decomposes to form N-methylacridone in its excited singlet state; relaxation to the ground state results in the emission of photons of light at a wavelength of 430 nm (Weeks et al., 1986).

Positive and negative control analytes were p170 EGFR/ErbB1 (Sigma) and a 60 kD trpEcentrin recombinant fusion protein (Baron et al., 1992), respectively. Analytes were prepared as dilution series in ALBB. Unknown samples included whole cell lysates, conditioned culture media, and human serum samples. All human sera were assayed at a 1:10 dilution in ALBB. Serial dilutions of whole cell lysates and conditioned culture media were made in ALBB. All assays were partially automated with a BIOMEK 1000 laboratory work station (Beckman Instruments, Palo Alto, Calif.).

ALSIA Results

As shown in FIG. 7, the above ALISA is specific for molecules containing subdomain IV of the extracellular domain of ErbB1 (p170 EGFR/ErbB1, A431 mutant p110 sEGFR/sErbB1, recombinant p100 sEGFR/sErbB1), but does not bind to molecules which do not contain subdomain IV (p60 sEGFR/sErbB1 and other unrelated molecules). Also, as demonstrated in this and the following examples, the ALISA is highly sensitive, and can detect sEGFR/sErbB1 in the femtomolar range.

Immunoprecipitation and Characterization of sErbB1 Analogs from Normal Human Sera Blood from healthy men and women was collected by Mayo Medical Laboratories (MML), Department of Laboratory Medicine and Pathology, in accordance with an Institutional Review Board approved Normal Values Study Program. Each healthy donor was required to provide a recent physical history that included a physical exam and the results of the following tests: Hematology Group, Chemistry Group, Lipids, Thyroid Function, and Urinalysis. Chest x-ray and electrocardiogram also were performed on age appropriate subjects. Detailed clinical records from these healthy subjects are available. Blood was allowed to clot at room temperature for 30 min. The serum was separated from the clot and cells by centrifugation at 2000×g for 10 minutes, divided into 1 ml aliquots, and stored at −70° C. All serum samples from MML were collected between 1981 and 1984. Each serum sample was thawed after transfer to our laboratory, aliquoted into smaller volumes, and refrozen at −70° C. to prevent sErbB1 degradation. Each serum sample was, therefore, frozen and thawed only twice before measurement by ALISA.

Normal human sera were cleared of lipids with Seroclear® according to the manufacturer's protocol (Calbiochem-Novabiochem, La Jolla, Calif.), diluted 1:5 (v/v) in Affi-Gel Protein-A MAPs II® binding buffer (Bio-Rad Laboratories, Hercules, Calif.) and clarified of human IgG molecules by passage through a Protein-G Superose® affinity column by FPLC using Affi-Gel Protein-A MAPs II® binding, elution, and regeneration buffers (Bio-Rad Laboratories). The column flow through was collected, concentrated by ultrafiltration, exchanged into TBS containing 0.02% $NaN_3$ by FPLC with a Sephadex® G-25 fast desalting gel filtration column, divided into four aliquots, and immediately incubated with uncoupled (MAb minus) or MAb R.1-, 225-, and 528-coupled affinity resins. Alternatively, human serum samples were simply clarified of human IgG molecules by incubating with Immunopure® Immobilized Protein-G resin (Pierce Chemical) for 30 minutes at room temperature prior to immunoprecipitation. Both methods yielded identical immunoprecipitation results. The MAb R. 1, 225, and 528 affinity resins were prepared with an Immunopure® Immobilized Protein-G IgG Orientation kit according to the manufacturer's instructions (Pierce Chemical); the MAb minus resin was prepared in an identical manner, except that no IgG was bound to Protein-G. Bound proteins were eluted from these resins with MAPs II® elution buffer, adjusted to neutral pH by adding 1.0 M Trizma® buffer (pH 9.0), and analyzed by SDS-PAGE and Western immunoblot.

SDS-PAGE was performed in 1.0 mm thick vertical slab minigels (7×8 cm) with a Mini-PROTEAN II apparatus (Bio-Rad Laboratories). The stacking gel contained 3% acrylamide and the resolving gel contained 10% acrylamide (Laemmli, 1970). All SDS-PAGE samples were prepared with 4× Laemmli sample buffer (250 in M Trizma®, pH 6.8, 8% SDS, 40% glycerol, 20% β-mercaptoethanol, 4 mM ethylenediaminetetraacetic acid, 0.08% bromphenol Blue) and boiled for 1 minute prior to electrophoresis. Gels were processed for Western immunoblot analyses.

Following SDS-PAGE, proteins were transferred to Immobilon® polyvinylidene difluoride (PVDF) membrane (Millipore, Bedford, Mass.) using a Type 1, Milliblot™ Graphite Electroblotter System (Millipore) according to the manufacturer's protocol. The membrane was allowed to air dry completely following protein transfer. The dry membrane was wet again with methanol, washed three times with Tween-20® wash buffer (T-20WB; 10 mM Trizma pH 7.4, 0.05% Tween-20®, 150 mM NaCl), and blocked with Nonfat Dry Milk (NFDM; 5% nonfat dry milk, 10 mM Trizma, pH 7.4, 150 mM NaCl, 0.02% $NaN_3$) at 4° C. overnight. NFDM blocking was followed by a second blocking step with 0.5% Boehringer Blocking Reagent (Boehringer Mannheim) in TBS with 0.02% $NaN_3$ at 37° C. for 1 hour. The membrane was rinsed briefly with T-20WB, incubated with primary antibody reagent (mixture of MAbs 15E11, 2D2, LA22, and C11 or MAbs 10B7, 15E11, 17H3, 2D2, LA22, C11, 111.6, and 199.12 alone) at 37° C. for 1 hour, washed with T-20WB for 1 hour, and incubated at 37° C. for 1 hour with peroxidase-conjugated goat anti-mouse antibody. Primary antibody reagents consisted either of neat conditioned culture media for MAbs 10B7, 15E11, 17H3, and 2D2 or of purified IgGs for MAbs LA22, C11, 111.6, and 199.12; each purified MAb was used at a final concentration of approximately 1 µg/ml. Conditioned culture media containing MAb consisted of RPMI-1640 medium supplemented with 10% or 20% FBS, 20 mM Hepes, pH 7.3, 2 mM L-glutamine, 1 mM sodium pyruvate, and 0.01% thimerosal (mercury [(o-carboxyphenyl)thio]-ethyl sodium) as a preservative. In some experiments, the membrane was washed with T-20WB and clamped into a multichannel Miniblotter™ (Immunetics, Cambridge, Mass.). Different channels were incubated with different primary antibody reagents at 37° C. for 1 hour, washed with T-20WB for 1 hour, and incubated at 37° C. for 1 hour with peroxidase-conjugated secondary antibody. To visualize antibody binding, the membrane was washed with T-20WB for 1 hour and reacted with the enhanced chemiluminescent substrate luminol (Amersham Life Science).

As shown in FIG. 14, a 110 kDa protein was immunoprecipitated from normal human male and female sera with the ECD-specific anti-EGFR/ErbB1 antibodies used in the above ALISA. Microsequence analysis of partially pure p110 sEGFR/sErbB1 from human serum using Matrix Assisted Laser Desorpiton Ionization Time of Flight Mass Spectrometry shows that this protein is derived from the 3.0 kb alternative transcript having SEQ ID NO. 2 of the invention.

Comparison to Commercially Available EGFR/ErbB1 ECD-Specific Enzyme-Linked Immunosorbent Assay (ELISA)

The EGFR ELISA (catalog #QIA3S from Oncogene Research Products) was performed exactly according to the manufacturer's instructions; i.e., standards and serum samples were diluted either into standard or sample diluent, respectively. This ELISA uses two MAbs that are specific for epitopes of the EGFR/ErbB1 receptor ECD in a sandwich configuration; the origin and characterization of these MAbs has not been disclosed by the manufacturer. The second MAb used in the ELISA is biotinylated and binds peroxidase-conjugated streptavidin. Detection of EGFR/ErbB1 is achieved by conversion of the chromogenic substrate tetra-methylbenzidine to a blue product by peroxidase, which is subsequently converted to a yellow product by the addition of stop solution (2.5 N sulfuric acid). The absorbance of the yellow reaction product was quantified with the spectraphotometry tool of a BIOMEK 1000 laboratory work station at 415 nm; a 560 nm reference filter was used for background subtraction.

Results of these experiments are shown in FIG. 15. Although the Oncogene ELISA did react with some substances in the sera of healthy men and women, it did not detect any difference in sEGFR/sErbB1 concentration between the two, nor did the ELISA results correlate with the ALISA results. Thus, the commercially available ELISA test differs substantially from the ALISA described herein.

Example VI

Establishment of Baseline sErbB1 Concentrations in Normal Male and Female Subjects In order to increase the usefulness of the above ALISA for determining abnormal sEGFR/sErbB1 values in patient sera, baseline or normal serum sEGFR/sErbB1 concentration values for men and women over a broad age range were established using the following methods:

Serum Samples

Blood from 88 healthy men and 144 healthy women was collected in accordance with a Institutional Review Board-approved "Normal Values Study." Briefly, all blood samples were processed into serum and stored at −70° C. until they were used. Serum sEGFR/sErbB1 levels were quantified for all the available samples. The gonadotropic and steroid hormone levels were measured in 83 of the 88 healthy men, and 123 of the 144 healthy women.

Menopausal Status Determination

Medical records were reviewed systematically to ascertain menopausal status at the time of the blood draw. Data collected include: date and patient age at the time of blood draw, date of last menstrual period (LMP), self-reported symptoms of menopause, date of surgical menopause (hysterectomy and/or oophorectomy), and FSH and/or LH levels. For patients who underwent surgical hysterectomy but not oophorectomy, the clinical records also were reviewed to determine the approximate date of clinical menopause (patient's self-report). The criteria used to assign menopausal status were one or more of the following: 1) age≧60 years, 2) last reported menstrual period>six months from the date of the blood draw, 3) symptoms of menopause, 4) hysterectomy, 5) oophorectomy, 6) FSH level<30 IU/L (premenopause), or >36 IU/L (postmenopause). Menopausal status for 6 of the 144 women could not be determined in this study, because a) FSH levels were equivocal or there was insufficient serum to measure these levels, or b) the patient's medical record was incomplete; i.e., a long time interval between the patient's last medical visit and the blood draw or the patient transferred health care to another facility.

p110 sEGFR/sErbB1 ALISA

Serum p110 sEGFR/sErbB1 levels were determined by AL1SA as outlined above in Example V. This ALISA specifically detects p110 sEGFR/sErbB1, and does not cross-react with p60 sEGFR/sErbB1, p105 sErbB2, or full-length ErbB2, ErbB3, or ErbB4. Initially, all sera were diluted 1:10 in ALISA blocking buffer (ALBB) and assayed in duplicate in three separate trials. Serum samples yielding relative light units (RLU's) below the linear range of the assay's standard curve were re-assayed either undiluted or diluted 1:5 in ALBB, whereas serum samples yielding RLU's above the linear range of the assay's standard curve were re-assayed either diluted 1:20 or 1:50 in ALBB. For each trial, the mean RLU's for each duplicate was determined and a corresponding sEGFR/sErbB1 concentration in fmol/ml was calculated. The final p110 sErbB1 concentration reported here, for each serum sample, is the median value from all three trials. The inter-assay biological detection limit for the p110 sEGFR/sErbB1 ALISAs performed was 10 fmol/ml.

Serum sErbB1 Levels Differ when Adjusting for Gender, Age, and Menopausal Status When unadjusted for age, serum p110 sEGFR/sErbB1 levels do not differ significantly between healthy men and women ranging in age from 20 to 79 years (See FIG. 8). A median serum p110 sEGFR/sErbB1 level of 6,816 fmol/ml (range: 837-42,533 fmol/ml) and 7,177 finol/ml (range: 114-31,465 fmol/ml) is reported for the men and women in this study, respectively. However, when taking age into consideration, significant negative and positive associations between serum p110 sEGFR/sErbB1 levels and age is observed in these healthy men (Spearman rank correlation coefficient=0.4562, p=0.0001) and women (Spearman rank correlation coefficient=−0.3491, p=0.0001), respectively (See FIGS. 9 A & B). Further analysis of sErbB1 levels with regard to menopausal status show that premenopausal and postmenopausal women have median serum p110 sEGFR/sErbB1 levels of 8,561 fmol/ml (range: 341-24,294 fmol/ml) and 3,400 fmol/ml (range: 114-31,465 fmol/ml), respectively (See FIG. 10). These data show that p110 sEGFR/sErbB1 levels are significantly higher in premenopausal women than postmenopausal women (p<0.0001). To determine if this difference is simply related to age, the men were age matched (±1 year) to the groups of premenopausal and postmenopausal women. Although the younger men were age matched to a subgroup of 71 premenopausal women, enough older men were not age matched to the postmenopausal group of women. A median serum p110 sEGFR/sErbB1 level of 8,740 fmol/ml (range; 747-24,294 fmol/ml) for the subgroup of premenopausal women and 5,883 fmol/ml (range: 837-28,602 fmol/ml) for the age-matched men (see FIG. 11) is reported. Interestingly, the serum p110 sEGFR/sErbB1 levels of the premenopausal women are also significantly higher than that of the younger men (p-0.009). These observations indicate that gender differences in serum sErbB1 levels exist between younger men and women, as well as between men and women 40 years and older. Moreover, these data suggest that the observed differences in sErbB1 levels between premenopausal and postmenopausal women are not simply a function of age, but may be modulated by the milieu of circulating gonadotropic and sex steroid hormones.

Example VII

Ovarian Cancer Patients Exhibit Significantly Reduced Serum sEGFR/sErbB1 Concentrations To explore the diagnostic potential of sEGFR/sErbB1, the ALISA described in Example V was utilized to compare pre-operative serum sErbB1 levels between 149 healthy women, 164 stage I, II, III, or IV ovarian cancer patients, 142 patients with benign ovarian tumors, and 115 patients with other benign gynecologic diseases of the pelvis. The individuals in each of these cohorts are within the same age range, but are not age-matched on a one-to-one basis. The cohort of patients with benign ovarian tumors had the following diagnoses: simple cyst, corpus luteum cyst, follicular cyst, dermoid, fibroma, mucinous cystadenoma, and serous cystadenoma; and the cohort of patients with other benign gynecologic pelvic diseases had the following diagnoses: paratubal cyst, cervical dysplasia, endometriosis, fibroids, and hydrosalpinx. The scattergram in FIG. 12 clearly shows that serum sEGFR/sErbB1 levels in EOC patients are significantly lower than those seen in healthy women (non-surgical patients), in patients with benign ovarian tumors, and in patients with other benign gynecologic pelvic diseases. Moreover, these data indicate that pre-operative serum sEGFR/sErbB1 levels may be useful in making a diagnosis between early as well as late stage EOC versus benign ovarian tumor and other benign gynecologic pelvic disease.

Example VIII

Post-Operative Serum sEGFR/sErbB1 Concentrations of Ovarian Cancer Patients are Altered as Compared to Pre-Operative Concentrations The serum sEGFR/sErbB1 levels of ovarian cancer patients was tracked using the ALISA described in Example V according to the following methods:

Sample Collection and ALISA Methods

Blood from healthy women was collected by the Department of Laboratory Medicine & Pathology, Mayo Medical Laboratories, in accordance with an ongoing institutional review board-approved Normal Values Study program and processed into serum. All serum samples from healthy women used in this study were collected between 1981 and 1984.

Between 1985 and 1994, serum samples from women presenting to the Mayo Clinic for gynecological surgery were collected and stored to study the reproducibility of CA-125 measurements in women with EOC (60-63). Patients with ovarian cancer were classified as having International Federation of Gynecology and Obstetrics stage I, II, III, or IV disease at the time of staging laparotomy and tumor reductive surgery. Serum samples were considered preoperative if they were collected within 30 days prior to surgery. Patients with a prior diagnosis of EOC that had received previous cytoreductive surgery, radiation, or chemotherapy were eliminated from our study. We identified serum samples from 21 patients, ranging in age from 15 to 83 years that fit these criteria.

Postoperative serum samples from patients with stage III or IV EOC were collected in accordance with North Central Cancer Treatment Group and Mayo Clinic Protocol 90-61-54, entitled "Cyclophosphamide plus carboplatin: comparison of conventional dose and double-dose carboplatin in patients with stage III or IV ovarian carcinoma—a Phase III study." All serum samples were collected between 1992 and 1994. Seventy-nine eligible patients were randomized to treatment on this study within 1 month after staging laparotomy and cytoreductive surgery.

Following collection, all blood samples were allowed to clot at room temperature for 30 min. The serum was separated from the clot and cells by centrifugation at 2000~X g for 10 min., divided into 1-ml aliquots, and stored at −70° C. Each serum sample was thawed after transfer into our laboratory, aliquoted into smaller volumes, and refrozen at −70° C. to prevent sEGFR/sErbB1 and EGF degradation. Each serum sample was, therefore, frozen and thawed only twice.

Serum sEGFR/sErbB1 levels were determined with an ALISA specific for epitopes of the ECD of ErbB1 according to Example V with the following ALISA blocking buffer (1.0% BSA, 10 mM Trizma, pH 7.4, 150 mM NaCl, 0.01% normal rabbit serum, 0.01% normal mouse serum, 0.02% $NaN_3$). Human sera were assayed undiluted or at dilutions of either 1:25 or 1:10 in ALISA blocking buffer. Initially, each serum sample was tested in duplicate at a 1:25 dilution in three separate experiments. Each serum sample was then tested in duplicate at a 1:10 dilution in three separate experiments. Finally, those serum samples that yielded undetectable sErbB1 levels at dilutions of 1:25 and 1:10 were tested undiluted in duplicate in three separate experiments. Undiluted serum samples that yielded values in relative light units below the interassay biological detection limit of 24 fmol/ml for this ALISA were considered undetectable. The sErbB1 concentration reported in the scattergrams for each serum sample represents the median of the mean sErbB1 level determined in three separate assays.

Results in Pre-Operative Vs. Post-Operative Samples

Serum samples collected within a period of 30 days prior to staging laparotomy and cytoreductive surgery from 21 stage III or IV EOC patients were identified; none of these patients had received prior chemotherapy, radiation, or debulking surgery. The serum sEGFR/sErbB1 levels in the EOC patients were compared to the serum sEGFR/sErbB1 levels in a group of 21 healthy women of similar ages. The median (range) serum sEGFR/sErbB1 concentration of the 21 age-matched healthy women is 6,395 fmol/ml (1,846-23,708 fmol/ml). In contrast, the median (range) preoperative serum sEGFR/sErbB1 concentration of the 21 patients with stage III or IV EOC is 284 fmol/ml (30-1,350 fmol/ml). These data indicate that preoperative serum sEGFR/sErbB1 levels in patients with stage III or IV EOC are significantly lower than serum sEGFR/sErbB1 levels in healthy women of similar ages (Wilcoxon rank sum test, P<0.0001).

Serum samples collected after staging laparotomy and cytoreductive surgery were also examined from 73 patients with stage III or IV EOC who presented for treatment between 1992 and 1994. These patients had not received prior debulking surgery, radiation, or chemotherapy for EOC, and were enrolled in a phase III randomized clinical trial to study the efficacy of cyclophosphamide plus conventional dose carboplatin versus cyclophosphamide plus an intensive dose of carboplatin in patients with stage III and IV EOC following surgery.

The initial postoperative (0-34 days) serum sEGFR/sErbB1 levels in these 73 EOC patients were compared to serum sErbB1 levels in a group of 73 healthy age-matched women (FIG. 13). The median (range) serum sEGFR/sErbB1 concentration of the 73 healthy women was 6,113 fmol/ml (1,292-51,358 fmol/ml). In contrast, the median (range) initial postoperative serum sEGFR/sErbB1 concentration of the 73 EOC patients was 1,799 fmol/ml (nondetectable to 11,035 fmol/ml). These data indicate that the initial postoperative sEGFR/sErbB1 levels in patients with stage III or IV EOC differ significantly from sEGFR/sErbB1 levels in an age-matched group of healthy women.

Thirty-three patients enrolled in the aforementioned phase III study provided a second serum sample 35-287 days after cytoreductive surgery. The median (range) serum sErbB1 concentration of these 33 serum samples was 6,434 fmol/ml (non-detectable to 29,666 fmol/ml). The median (range) serum sEGFR/sErbB1 concentration of these 33 serum samples appeared similar to that seen in healthy women, with the exception of one patient who had an undetectable level of serum sEGFR/sErbB1 (See FIG. 13). It is noteworthy that the median serum sEGFR/sErbB1 concentrations for both the initial and second postoperative serum samples appear higher than those seen in preoperative serum samples of patients with stage III or IV EOC. Statistical comparisons of the sEGFR/sErbB levels in the serum samples collected 0-34 days after cytoreductive surgery with those in the serum samples collected 35-287 days after cytoreductive surgery in a group of healthy women were not performed, because these 33 serum samples represent a subset of the 73 patients enrolled in the phase III study and they were collected over a protracted time period, i.e., 253 days. Examination of the sEGFR/sErbB1 concentration in the initial versus the second serum sample for each of the 33 patients who underwent cytoreductive surgery shows that sErbB1 levels increased temporally for many, but not for all of these 33 patients during the course of combination chemotherapy. The sEGFR/sErbB1 level of one patient in fact decreased below detectable levels.

These results indicate the ALISA of Example V is an important tool for monitoring the progression or regression of ovarian cancer in patients who are undergoing surgical, radiation, or chemotherapy treatments. The ability to monitor patient progress using sEGFR/sErbB1 as a marker may be especially useful in detecting post-surgical recurrence of the disease.

Example IX

Research Suggests that p110 sEGFR/sErbB1 is a Glycosylphosphatidylinositol-Anchored Protein Research suggests that p110 sEGFR/sErbB1 is localized to the membrane via the addition of a glycosylphosphatidylinositol (GPI) anchor. The core structure common to all GPI anchors consists of a glycan bridge between phosphatidylinositol and phosphoethanolamine with phosphoethanolamine attached to the carboxy-terminus of the protein. GPI anchors are added to proteins containing an appropriate carboxy-terminal signal sequence. This linkage is a post-translational modification that occurs in the lumen of the endoplasmic reticulum within minutes of protein synthesis. The carboxy-terminal signal sequence consists of a cleavage/attachment site, called the omega site (w), a short hinge region that contains charged amino acids, and a carboxy-terminal hydrophobic region of varying length. The carboxy-terminal signal sequences of several known GPI proteins, as well as the predicted signal sequences present in human p110 sEGFR/sErbB1 (and in an analogous mouse p110 sEGFR/sErbB1)

are known. Compared to known GPI signal sequences, both the human (SEQ ID NO: 18; SEQ ID NO:19) and the murine (SEQ ID NO:20) sEGFR/sErbB1 receptors contain potential carboxy-terminal GPI anchor signal sequences. In fact, the human p110 sEGFR/sErbB1 product contains 2 putative signal sequences; the significance of tandem signal sequences is not known, but potentially either could be used.

Example X p110 sEGFR/sErbB1 and CA-125 as a Test for Epithelial Ovarian Cancer

An accurate diagnostic test or cancer probability index would be a particularly valuable aid to clinicians caring for women with ovarian tumors. A tumor with a high probability of malignancy could be promptly referred to a gynecological oncologist for initial surgical management, thereby improving patient survival.

The cutoff value chosen for an individual diagnostic test is well known to set the parameters of specificity, sensitivity, positive predictive value (PPV), and negative predictive value (NPV) for that particular test Hennekens, C. H. and Buring (1987). Screening. Epidemiology in Medicine. S. L. Mayrent. Boston: Little, Brown: 327-47 (Chapter 13). Cutoff thresholds that favor higher sensitivity and NPV yield lower specificity and PPV, and vice versa. Besides the cutoff threshold, the manner in which multiple tests are used also affects the relationship between sensitivity and NPV versus specificity and PPV. Two or more tests can be applied "in parallel" or "in series." Parallel testing involves the administration of more than one test simultaneously. Individuals who receive a positive result for one "or" the other test are considered to have cancer. By identifying more true positives, parallel testing has the effect of increasing the probability of detecting cancer (higher sensitivity), while decreasing specificity. In contrast, serial testing involves administering more than one test sequentially. Individuals who receive a positive test result on the first test are evaluated further with a second test; a second positive test result may then evoke a third test and so forth, until a confirmatory diagnostic procedure is performed. Individuals who receive a positive test result on both the first "and" subsequent tests are considered to have cancer. By identifying more true negatives, serial testing has the effect of increasing the probability of identifying individuals without disease (higher specificity) at the expense of sensitivity. Alternatively, parallel versus serial testing can be evaluated mathematically by applying algorithms that use "or" versus "and" decision rules, which allow all tests to be administered and analyzed simultaneously. The mathematical algorithm applied to multiple tests, therefore, is equal in importance to the cutoff threshold of each component test. Furthermore, both the cutoff threshold and algorithm interact in a complex manner to affect the overall validity (sensitivity and specificity) and feasibility (PPV and NPV) of the overall testing procedure.

Recently, Baron et al, analyzed serological p110 sEGFR and CA125 in women with EOC compared to women with benign ovarian tumors using "in series" and "in parallel" testing algorithms, as well as MLR modeling, which incorporates "and" decision rules, but further allows the statistician to adjust for confounding or effect modification by other covariates and to define nonlinear relationships (Baron, A. T., et al., Cancer Epidemiol Biomarkers Prey, 14: 306-18, 2005). MLR thus is more powerful than simple "in series" and "in parallel" testing algorithms, because it can model complex relationships between multiple biomarkers and other covariates and, therefore, optimizes the ability to classify individuals into dichotomous groups.

Serum CA125 and sEGFR concentrations were found to have a moderate inverse associated among EOC case (Spearman's rank-order correlation coefficient, r=−0.3031, p<0.0001), but not among women with benign ovarian tumors (Baron, A. T., et al., Cancer Epidemiol Biomarkers Prey, 14: 306-18, 2005). As expected, parallel testing with fixed sEGFR ($\leqq$1000 fmol/ml) "or" CA125 ($\geqq$50 Units/ml) cutoff thresholds optimized sensitivity (84.8%) to detect EOC, whereas serial testing with fixed sEGFR ($\leqq$1000 fmol/ml) "and" CA125 ($\geqq$50 Units/ml) cutoff thresholds optimized specificity (100%) to classify women with benign ovarian tumors correctly (Table 2).

TABLE 2

Statistics of test validity for EOC cases compared to patients with benign ovarian tumors.

|  | All stages EOC | Stage I/II EOC | Stage III/IV EOC |
|---|---|---|---|
| $\alpha \leqq$ 1000 fmol/ml sEGFR or $\geqq$50 Units/ml CA125 | | | |
| Sensitivity (%) | 84.8% | 56.8% | 91.7% |
| Specificity (%) | 63.4% | | |
| Accuracy (%) | 73.6% | | |
| $\gamma \leqq$ 1000 fmol/ml sEGFR and $\geqq$50 Units/ml CA125 | | | |
| Sensitivity (%) | 50.9% | 4.8% | 61.6% |
| Specificity (%) | 100.0% | | |
| Accuracy (%) | 76.7% | | |
| θ Multivariate Logistic Regression Model | | | |
| Sensitivity (%) | 66.7% | 13.2% | 79.6% |
| Specificity (%) | 100.0% | | |
| Accuracy (%) | 84.7% | | |
| θ Multivariate Logistic Regression Model | | | |
| Sensitivity (%) | 72.3% | 23.7% | 85.4% |
| Specificity (%) | 97.0% | | |
| Accuracy (%) | 85.7% | | |

α—parallel testing, abnormal sEGFR "or" CA125 give a positive test result for cancer
γ—serial testing, abnormal sEGFR "and" CA125 give a positive test result for cancer
θ—Model included the terms log sEGFR, log CA125, age, (log sEGFR × log CA125), and (log CA125 × age)

Parallel testing detected 56.8% and 91.7% of the stage I/II and stage III/IV EOC cases, respectively, compared to just 4.8% and 61.6% of the of stage I/II and stage III/IV EOC cases detected by serial testing. Importantly, MLR modeling demonstrated that age and serum sEGFR concentrations modify the association between CA125 levels and EOC versus benign ovarian tumors, thus indicating that age- and sEGFR-dependent CA125 cutoff thresholds are appropriate when using serum CA125 to diagnose EOC. An extended MLR model, which included the terms log sEGFR, log CA125, age, (log sEGFR×log CA25), and (log CA125×age) to simultaneously fit age- and sEGFR-dependent CA125 cutoff thresholds discerned women with EOC from women with benign ovarian tumors better than a one-term model that included only log CA125 (−2 log likelihood ratio $\chi^2$ test, p<0.0005). Receiver operating characteristic (ROC) analyses showed that the extended MLR model has 87.2% (95% CI, 83.6-90.7%) probability of correctly discerning EOC cases from women with benign ovarian neoplasms (FIG. 16), across all age- and sEGFR-dependent cutoff thresholds of CA125, respectively. Sensitivity to detect stage I/II, stage III/IV, and all EOC cases is 13.2%, 79.6%, and 66.7% where the extended model converges to 100% specificity and 84.7% accuracy (Table 2); this is an improvement over serial testing with fixed sEGFR (≦1000 fmol/ml) "and" CA125 (≧50 Units/ml) cutoff thresholds. Finally, the extended model has 23.7%, 85.4%, and 72.3% sensitivity to detect stage I/II, stage III/IV, and all EOC cases where the model converges to 97% specificity and 85.7% accuracy (Table 2).

In conclusion, multivariate logistic regression, which can simultaneously model testing with age- and sEGFR-dependent CA125 cutoff thresholds, optimizes the overall ability to discern patients with EOC from women with benign ovarian tumors. Interestingly, Jacobs et al. have reported that a risk of malignancy index (RMI), which incorporates CA125, sonographic imaging, and menopausal status, has 85% sensitivity to correctly classify malignant from benign ovarian tumors at 97% specificity. Likewise, multivariate nonlinear unified maximum separability models that incorporate CA125, apolipoprotein Al, a truncated form of transthyretin, and a fragment of inter-alpha-1 trypsin inhibitor heavy chain 4 demonstrated 78% sensitivity to correctly classify malignant from benign ovarian tumors, but with just 45% specificity. Accordingly, testing with sEGFR, CA125, TVS MI, age, and other biomarkers are useful for making a differential diagnosis of EOC.

p110 sEGFR/sErbB1 and Gonadtropic Hormones as a Test for Epithelial Ovarian Cancer To explore the potential utility of serum p110 sEGFR, FSH, and LH concentrations as biomarkers for EOC, concentrations of each potential biomarker between 124 healthy women and 47 women with EOC were compared. Serum p110 sEGFR concentrations were determined by acridinium-linked immunosorbent assay (ALISA) as described above. Serum FSH concentrations were measured according to manufacturer's instructions using the ACS:180 Immunoassay Analyzer (Bayer Corporation-Diagnostics Division, Tarrytown, N.Y.). The FSH ACS:180 is a chemiluminescent sandwich immunoassay, which uses paramagnetic particles as the solid phase and acridinium-based photochemistry. The minimum detectable concentration of FSH according to the ACS:180 Immunoassay Analyzer manufacturer's instructions is reported to be 0.2 IU/l. Serum LH concentrations were determined following the manufacturer's instructions using the Access Immunoassay System (Beckman-Coulter, Fullerton, Calif.). The Access Immunoassay is an immunoenzymatic sandwich assay that also uses paramagnetic particles as the solid phase, but in contrast to the ACS assay, alkaline phosphatase is used to produce the luminescence signal rather than an acridinium labeled molecule. The minimum detectable concentration of luteinizing hormone according to the manufacturer's instructions is reported to be 0.2 IU/l.

Descriptive statistics were calculated and the Wilcoxon rank-sum test was used to determine if significant differences in p110 sEGFR, FSH, and LH concentrations exist between healthy women and women with EOC. Spearman's rank-order correlation coefficient was used to assess relationships between p110 sEGFR, FSH, and LH concentrations and age in the two groups of women. To reduce departure from the normal distribution, values for p110 sEGFR, FSH, and LH were log-transformed prior to logistic regression analyses. Univariate logistic regression models were used to assess whether log sEGFR, log FSH, and log LH concentrations as well as age and menopausal status are associated with EOC. Multivariate logistic regression modeling was used to examine the diagnostic utility of log sEGFR while simultaneously adjusting for confounding and/or effect modification by log FSH, log LH, age, and menopausal status as well as any potential interactions between the covariates. Receiver Operator Characteristic (ROC) curves were used to assess the ability of the logistic regression models to discern healthy women from women with EOC. Models were compared based on the area under the curve (AUC) values, which estimate the probability of correctly discerning a person with cancer from a person without cancer across all possible cutoff thresholds. AUC values range from 0.5 (no discriminatory ability) to 1.0 (perfect discriminatory ability).

Test sensitivity was calculated at 95, 98, and 100% test specificities to compare the utility of the univariate and multivariate models for screening and diagnosis of EOC. The cancer probability index was constructed based on a seven-term multivariate logistic regression model derived by backward stepwise elimination from a full model containing log sEGFR, log FSH, log LH, age, menopausal status and all possible interactions. The seven term multivariate model was internally validated using a subset of the original data. For this validation, 82 healthy women and 31 women with EOC were used to train the seven-term multivariate logistic regression model containing log sEGFR, log FSH, log LH, age, menopausal status, age×log sEGFR, age×log LH. The model was tested using 42 healthy women and 16 cases of EOC. A two-sided McNemar's test was used to determine if there was a significant difference in accuracy between the two models. The internally validated seven-term model was then used to classify all observations in the original dataset to generate predicted probabilities of disease ranging from 0 (0% probability of EOC) to 1 (100% probability of EOC).

To explore the potential utility of serum p110 sEGFR, FSH, and LH concentrations as biomarkers for EOC, concentrations of each potential biomarker between 124 healthy women and 47 women with EOC were compared. Descriptive statistics show that the 47 EOC cases and 124 healthy women were between 38 to 83 and 20.7 to 74.7 years in age, respectively. Overall, the EOC cases were older than the healthy women (median age: 62 versus 42.2 years); hence, 41 of the 47 EOC cases (87.2%) and 46 of the 124 healthy women (37.1%) were postmenopausal. Among the women with EOC, there were 2 (4.3%), 36 (76.6%), and 9 (19.1%) Stage I, III, and IV cases, respectively.

Overall, healthy women have significantly higher serum p110 sEGFR concentrations (Wilcoxon rank sum, P<0.0001) when compared to women with EOC (Table 3, FIG. 17A), whereas healthy women have significantly lower FSH concentrations (Wilcoxon rank sum, P=0.0435) compared to women with EOC (Table 3, FIG. 17B). LH concentrations were not found to differ significantly (Wilcoxon rank sum, P=0.1880) between healthy women and women with EOC (Table 3, FIG. 17C). Comparison of p110 EGFR concentrations versus age revealed that p110 sEGFR concentrations decrease with age in healthy women (FIG. 18A; rho=-0.36958; P<0.0001) and in women with EOC (FIG. 18B; rho=-0.31512; P=0.0310). FSH concentrations were found to increase with age in healthy women (FIG. 18C; rho=-0.73123; P<0.0001) and trended towards higher concentration with age in women with EOC (FIG. 18D; rho=0.26741, borderline significance, P=0.0692). LH concentrations increased with age in healthy women (FIG. 18E; rho=0.66628, P<0.0001), but were not significantly associated with age in women with EOC (FIG. 18F; rho=0.01916; P=0.8983).

TABLE 3

Descriptive statistics and comparison of serum p110 sEGFR, FSH, and LH concentrations among healthy women and women with EOC

| | Healthy (n = 124) | OVCA (n = 47) | Wilcoxon Rank Sum P-value |
|---|---|---|---|
| Age (Years) | 42.2 (20.7-74.7) | 62 (38.0-83.0) | |
| Menopausal status | | | |
| n(pre):n(post) | 78:46 | 6:41 | |
| Stage | | | |
| I | | 2 | |
| II | | | |
| III | | 36 | |
| IV | | 9 | |
| sEGFR (fmol/ml) median (range) | 7,177 (114-24,294) | 208 (7.5-11,573) | <0.0001 |
| FSH (Units/ml) median (range) | 7.01 (0.27-140.11) | 30.3 (0.6-94.4) | 0.0435 |
| LH (Units/ml) median (range) | 8.59 (0.2-74.97) | 17.2 (0.001-58.1) | 0.1880 |

Univariate and multivariate logistic regression models were constructed to assess the effects of log sEGFR, log FSH, and log LH concentrations as well as menopausal status and age on disease status. Univariate logistic regression analyses revealed that low serum p110 sEGFR concentrations ($P<0.0001$), low serum FSH concentrations ($P=0.0052$), postmenopausal status ($P<0.0001$), and older age ($P<0.0001$), but not LH concentrations ($P=0.2038$), are associated significantly with a positive classification of EOC (Table 3). Multivariate logistic regression modeling shows that log sEGFR ($P<0.0001$), age ($P=0.0355$), and menopausal status ($P=0.0109$), as well as log FSH ($P=0.0026$) and log LH ($P=0.0132$) concentrations all are associated significantly with EOC when these covariates are mutually adjusted for confounding (Table 4).

TABLE 4

Univariate and multivariate logistic regression analysis: p-values and AUC values for prognostic factors.

| | Univariate Analysis | | Multivariate Analyses | | | |
|---|---|---|---|---|---|---|
| Variable | Wald $\chi^2$ P-value | AUC | Variable | Wald $\chi^2$ P-value | AUC | Wald $\chi^2$ P-value | AUC |
| Age | <0.0001 | .852 | Age | 0.0355 | | 0.5638 | |
| log sEGFR | <0.0001 | .937 | log sEGFR | <0.0001 | | 0.0116 | |
| log FSH | 0.0052 | .601 | log FSH | 0.0026 | | 0.0031 | |
| log LH | 0.2038 | .565 | log LH | 0.0132 | | 0.0071 | |
| Menopausal status | <0.0001 | .751 | Menopausal status | 0.0109 | .964 | 0.0536 | |
| | | | Age × log sEGFR | | | 0.0598 | |
| | | | Age × log LH | | | 0.0272 | .973 |

An extended multivariate logistic regression model (Table 4), which included the terms log sEGFR, log FSH, log LH, age, menopausal status, and all possible pairwise interactions revealed significant interactions between age and log sEGFR (borderline significance; $P=0.0598$), as well as between age and log LH ($P=0.0272$). This model, which was able to fit simultaneously age- and LH-dependent cutoff thresholds and to adjust for confounding by FSH and menopausal status, discerns patients with EOC from healthy women better than the one term model that included only log sEGFR ($-2$ log likelihood ratio $\chi^2$ test, $P<0.0005$).

Receiver Operating Characteristic (ROC) curves show that the one-term model, which incorporates only log sEGFR, correctly distinguishes the patients with EOC from healthy women with 93.7% (95% CI, 88.7-98.7%) probability across all cutoff thresholds of p110 sEGFR (FIG. 19A). For the one term model, sensitivity for detecting stage I/II, stage III/IV, and all EOC cases is 50.0%, 42.2%, and 40.4% where the model converges to 100% specificity, respectively (FIG. 19A, arrow; Table 5). The five-term multivariate model, which included log sEGFR, log FSH, log LH, age, and menopausal status, was able with 96.4% (95% CI, 92.6%-100%) probability to discern between healthy women and women with EOC (FIG. 19B). In contrast, the extended seven-term multivariate model has 97.3% (95% CI, 94.0-101%) probability of correctly discerning EOC cases from healthy women across all FSH- and menopause-adjusted, and age- and LH-dependent cutoff thresholds of sEGFR (FIG. 19C). Finally, the extended model has 100%, 51.1%, and 53.2% sensitivity to detect stage I/II, stage III/IV, and all EOC cases, respectively, where the model converges to 100% specificity (FIG. 19C, arrow; Table 5).

TABLE 5

Comparison of sensitivities at 95, 98, and 100% specificities for a logistic regression model containing only log p110 sEGFR versus a MLR containing log p110 sEGFR, log FSH, log LH, age, menopausal status, (age × log sEGFR), and (age × log LH)

| | Model | All Stages (n = 47) | Stage I/II (n = 2) | Stage III/IV (n = 45) |
|---|---|---|---|---|
| 95% Specificity | log sEGFR only | 72.3% | 100% | 71.1% |
| | MLR | 76.6% | 100% | 77.8% |
| 98% Specificity | log sEGFR only | 57.4% | 100% | 55.6% |
| | MLR | 63.8% | 100% | 64.4% |
| 100% Specificity | log sEGFR only | 40.4% | 50.0% | 42.2% |
| | MLR | 53.2% | 100% | 51.1% |

To assess the validity of the seven-term multivariate logistic regression model, we performed an internal validation using training and test sets randomly derived from the original data and compared the classification results of the internal validation model to the seven-term model. Comparison of the two models revealed concordance in their classification of healthy women and women with EOC with the exception of 2 discordant results (data not shown, kappa=0.9684) proving that both models have a substantially equivalent ability to discern between healthy women and women with EOC (McNemar's test, P=1.00).

Construction of a cancer probability index using the extended seven term logistic regression model reveals that healthy women have probability values ranging between 0 and 88.2%, whereas women with EOC have overlapping probability values ranging between 9.5-100% (FIG. 20). Using a 0.5 probability cut-off, this model would misclassify 5 of the 124 healthy women as having EOC and misclassify 10 women of the 47 women with EOC as being healthy.

At 95%, 98%, and 100% specificities, the extended multivariate logistic regression model is better able to correctly identify women with EOC compared to the one term model containing only log sEGFR across all stages and in early (I/II) and late (III/IV) stage disease (Table 4). For early stage disease, both models were able to correctly identify 100% of the women at 95% and 98% specificity, but the log sEGFR model was only able to correctly identify 50% of the women with EOC at 100% specificity compared to 100% for the seven-term multivariate model.

These data show that serum sEGFR concentrations are significantly higher in healthy women compared to women with EOC. The data also show that FSH concentrations are significantly lower in healthy women compared to women with EOC. Serum sEGFR concentrations were found to decrease with age in healthy women and in women with EOC. Further, we find that low serum sEGFR concentrations (P<0.0001), low serum FSH concentrations (P=0.0052), postmenopausal status (P<0.0001), and older age (P<0.0001), but not LH concentrations (P=0.2038), are associated significantly with a positive classification of EOC (Table 3). The association of age and menopausal status with EOC clearly reflects the age difference between the healthy women and EOC cases used in this study and the higher incidence of EOC among older postmenopausal women in the population. Therefore, these covariates are likely to be confounders of the association between serological sEGFR and a classification of EOC.

With a prevalence of 1 in 2500 among postmenopausal women in the United States, this equates to requiring a test to have a sensitivity of 75% and a specificity above 99.7%. Using ROC analyses, the data show that serum p110 sEGFR alone has a 93.7% probability of correctly discerning between a healthy woman and a woman with EOC. The data further show that diagnostic accuracy can be improved by accounting for FSH, LH, age and menopausal status. The analysis shows that accounting for effect modification and/or confounding of p110 sEGFR by FSH, LH, menopausal status and age improves the sensitivity and specificity for detection of EOC compared to that p110 sEGFR only. Construction of a cancer probability index derived from a logistic regression model incorporating serum p110 sEGFR, FSH, LH, menopausal status, and age is a reliable, cost effective method for the risk assessment, screening, and diagnosis of EOC.

Artificial neural networks (ANN) have been proven to be useful multivariate classification tools in several diverse disciplines of science, business, engineering, and most recently, medicine. ANN models are particularly suitable analytical tools when the relationships between the input variables and the study groups (output variables) are unknown and/or highly nonlinear. Defining an appropriate nonlinear relationship is often the most difficult, and at times an almost impossible step, in traditional MLR analysis. Unlike traditional MLR analyses, which require the statistician to assess and specify explicitly the mathematical relationships between each of the input variables and the output variable, ANN models are capable of efficiently and effectively learning complex relationships by a training process called error back-propagation that involves repetitive rudimentary arithmetic calculations and certain simple, well-defined transformation functions. FIG. 21A shows one of the most commonly used artificial neural networks referred to as a layered, feed-forward 3:4:1-architecture. The layers in the 3:4:1-architecture contain three neuronal nodes where information is supplied to the ANN (input layer), four nodes where information is assimilated and transformed within the ANN (hidden layers), and one node where results are extracted from the ANN (output layer). An ANN typically contains one input layer, one output layer, and one or more hidden layers. The lines connecting different layers are referred to as neural network connections. Each connection in an ANN has an associated weight that modifies information passing through the connection and is analogous to regression constants of traditional regression tools. The information accumulated at a neuronal node might undergo a certain transformation (linear or nonlinear) before being transferred to a node in the adjacent layer. Equation 1 represents one such function referred to as a sigmoid transformation function:

$$O = \frac{1}{1 + \exp(-I)} \text{ where,} \quad (1)$$

I=weighed sum of all the inputs to a node, and O transformed output from a neuronal node.

Another nonlinear activation function called a hyperbolic function also is used successfully in many research studies. This function is defined as:

$$O = \frac{\exp(I) - \exp(-I)}{\exp(I) + \exp(-I)} \quad (2)$$

The repeated use of transformation functions, such as the ones shown in Equation 1 and 2, coupled with the rudimentary computations associated with connection weights enable ANN models to learn complex relationships between the input variables and to discern the study groups (output variables) under investigation.

To assess the ability of an ANN model to classify correctly the 127 healthy women and 51 EOC patients, a 5:7:1-architecture was used with serological sEGFR, FSH, and LH concentrations, age, and menopausal status as the input variables (FIG. 21B). The model contained a hyperbolic function in the hidden layer and sigmoid function in the output layer. In addition to using the complete database of 178 patients to develop a prime sEGFR-based ANN model, the database was split into a training set and testing set to assess internal validity. Briefly, the complete database was randomly shuffled and split to provide 138 patients for training and 40 patients for testing. Remarkably, these analyses demonstrate that the input variables: p110 sEGFR, FSH, LH, age, and menopausal status can detect 49 of the 51 (96.1%) EOC cases and classify 100% of the 127 healthy women correctly, thus achieving 98.9% (95% CI, 93.0-99.99%) accuracy to discern correctly the EOC cases from healthy women (Table 6). Notably, 2 of 3 stage I/II EOC cases were classified correctly using the prime ANN model yielding 66.7% sensitivity, equal in performance to the seven-term MLR model. Random splitting of the database into training and testing data sets for ANN model building and internal validation yielded comparable results. The trained model demonstrated 97.5% sensitivity, 100% specificity, and 99.3% accuracy with the training data set and 90.9% sensitivity, 93.1% specificity, and 92.5% accuracy with the testing data set.

TABLE 6

Statistics of test sensitivity, specificity, and accuracy to discern healthy women (n = 127) from women with epithelial ovarian cancer (n = 51) with artificial neural network models that incorporate the parameters sEGFR, FSH, LH, Menopausal Status, and Age.

| Model (n) | Sensitivity | Specificity | Accuracy |
|---|---|---|---|
| Complete (178) | 49/51 (96.1%) | 127/127 (100.0%) | 176/178 (98.9%) |
| Training (138) | 39/40 (97.5%) | 98/98 (100.0%) | 137/138 (99.3%) |
| Validation (40) | 10/11 (90.9%) | 27/29 (93.1%) | 37/40 (92.5%) |

Constructing a cancer probability index from the prime p110 sEGFR-based ANN model reveals that healthy women have extraordinarily low probability values ranging between 0-12.4%, whereas women with EOC have overlapping probability values ranging between 0-100% (FIG. 22). However, further inspection reveals that these healthy women and EOC cases have predicted probability values closely clustered near the expected values of 0 (zero) and 1 (one), respectively, indicating a very strong relationship between the input parameters (p110 sEGFR, FSH, LH, age, and menopausal status) and the expected diagnostic group (healthy vs. EOC). Indeed, only 2 of the 51 patients with EOC have a probability value <50%; the remaining 49 EOC cases have probability values ranging between 67.6-100%. As such, this p110 sEGFR-based ANN model could be used to classify women with probability values ranging between 0-12.4% and 12.5-100% into groups having a low and high likelihood of malignancy in a screening venue, respectively. The ANN model, hence, does not define a zone indicating a moderate likelihood of malignancy. Remarkably, this ANN model would stratify 100% of the 127 health women into the low risk zone, and 96.1% of the 51 women with EOC into the high risk zone. Only 2 women with EOC having probability values of 0% are misclassified. Notably, the cancer probability index of this p110 sEGFR-based ANN is substantially more pronounced in separating the controls from the EOC cases compared to the p110 sEGFR-based MLR model (compare FIG. 20 vs. FIG. 22).

Taken together, these analyses indicate that MLR or ANN models incorporating p110 sEGFR, FSH, LH, age, and menopausal status have utility as screening and diagnostic algorithms of EOC. Moreover, if analogous MLR and/or ANN models incorporating p110 sEGFR, FSH, LH, age, and menopausal status, plus MI and other complementary biomarkers are developed to discern patients with malignant versus benign ovarian tumors, women with a high likelihood of having epithelial ovarian cancer might be recommended for immediate surgery, whereas women with a moderate likelihood of malignancy might be recommended for repeat testing or other biomarker tests, and women with a low likelihood of malignancy might choose to be followed expectantly, thus avoiding surgery altogether.

There will be various modifications, improvements, and applications of the disclosed invention that will be apparent to those of skill in the art, and the present application encompasses such embodiments to the extent allowed by law. Although the present invention has been described in the context of certain preferred embodiments, the full scope of the invention is not so limited, but is in accord with the scope of the following claims.

We claim:

1. An isolated antibody that specifically recognizes a p110 soluble epidermal growth factor receptor (sEGFR) polypeptide, wherein said antibody binds a carboxy terminus specific to said p110 sEGFR polypeptide comprising amino acids 628 to 705 of SEQ ID NO: 1.

2. The antibody of claim 1 wherein said antibody binds amino acids 644 to 658 of SEQ ID NO: 1 or amino acids 628 to 658 of SEQ ID NO: 1.

3. The antibody of claim 1, wherein said antibody is a monoclonal antibody.

4. The antibody of claim 1, wherein said antibody is a polyclonal antibody.

5. The antibody of claim 1, wherein said antibody is a humanized or chimeric antibody.

6. The antibody of claim 1, wherein said antibody is a human antibody.

7. The antibody of claim 1, wherein said antibody is conjugated to a quantifiable or therapeutic moiety.

8. The antibody of claim 1, wherein said antibody is a therapeutic agent.

9. A kit comprising a p110 soluble epidermal growth factor receptor (sEGFR) antibody wherein said p110 sEGFR antibody binds a carboxy terminal region of p110 sEGFR comprising amino acid residues 628 to 705 of SEQ ID NO: 1.

10. A pharmaceutical composition comprising a p110 soluble epidermal growth factor receptor (sEGFR) antibody and a pharmaceutically acceptable carrier, wherein the p110 sEGFR antibody binds a carboxy terminal region of p110 sEGFR comprising amino acid residues 628 to 705 of SEQ ID NO: 1.

* * * * *